(12) United States Patent
Poncelet et al.

(10) Patent No.: US 11,583,524 B2
(45) Date of Patent: Feb. 21, 2023

(54) INHIBITORS OF THE INTERACTION BETWEEN MDM2 AND P53

(71) Applicant: Janssen Pharmaceutica NV, Beerse (BE)

(72) Inventors: Virginie Sophie Poncelet, Le Manoir sur Seine (FR); Sophie Coupa, Belbeuf (FR); Pierre-Henri Storck, Kent (GB); Bruno Schoentjes, Bois-Guillaume (FR)

(73) Assignee: Janssen Pharmaceutica NV, Beerse (BE)

( * ) Notice: Subject to any disclaimer, the term of this patent is extended or adjusted under 35 U.S.C. 154(b) by 0 days.

(21) Appl. No.: 16/718,955

(22) Filed: Dec. 18, 2019

(65) Prior Publication Data

US 2020/0121667 A1    Apr. 23, 2020

Related U.S. Application Data

(60) Continuation of application No. 15/983,043, filed on May 17, 2018, now Pat. No. 10,635,740, which is a division of application No. 15/398,291, filed on Jan. 4, 2017, now abandoned, which is a division of application No. 12/678,961, filed as application No. PCT/EP2008/062433 on Sep. 18, 2008, now Pat. No. 9,573,933.

(30) Foreign Application Priority Data

Sep. 21, 2007 (EP) .................. 07116889

(51) Int. Cl.
| | |
|---|---|
| A61K 31/438 | (2006.01) |
| A61K 31/55 | (2006.01) |
| A61K 9/28 | (2006.01) |
| A61K 45/06 | (2006.01) |
| C07D 401/12 | (2006.01) |
| C07D 487/04 | (2006.01) |
| A61K 31/4439 | (2006.01) |
| A61K 31/4709 | (2006.01) |
| A61K 31/5377 | (2006.01) |

(52) U.S. Cl.
CPC .......... *A61K 31/4439* (2013.01); *A61K 9/28* (2013.01); *A61K 31/438* (2013.01); *A61K 31/4709* (2013.01); *A61K 31/5377* (2013.01); *A61K 31/55* (2013.01); *A61K 45/06* (2013.01); *C07D 401/12* (2013.01); *C07D 487/04* (2013.01)

(58) Field of Classification Search
CPC .............. C07D 401/12; C07D 487/04; A61K 31/4439; A61K 9/28; A61K 31/438; A61K 31/4709; A61K 31/5377; A61K 31/55; A61K 45/06
USPC ...................................................... 549/406
See application file for complete search history.

(56) References Cited

U.S. PATENT DOCUMENTS

| | | |
|---|---|---|
| 9,573,933 B2 | 2/2017 | Poncelet et al. |
| 2004/0132800 A1 | 7/2004 | Chen et al. |
| 2008/0153799 A1 | 6/2008 | Laurent et al. |
| 2009/0149493 A1 | 6/2009 | Lacrampe et al. |

FOREIGN PATENT DOCUMENTS

| | | | |
|---|---|---|---|
| JP | 2004-532209 | 10/2004 | |
| JP | 2007-522210 | 8/2007 | |
| JP | 2009-531321 | 9/2009 | |
| WO | 01/42224 A1 | 6/2001 | |
| WO | 2006/032631 A1 | 3/2006 | |
| WO | WO 2006/032631 * | 3/2006 | .......... C07D 401/12 |
| WO | 2006/089286 A2 | 8/2006 | |
| WO | 2006/136606 A2 | 12/2006 | |
| WO | 2007/107543 A1 | 9/2007 | |
| WO | 2009/019274 A1 | 2/2009 | |

OTHER PUBLICATIONS

Park et al. in Annu. Rev. Pharmacol. Toxicol. 2001, 41:443-470 (Year: 2001).*
See MedicineNet ("Cancer" at http://www.medterms.com) (Year: 2011).*
Park, et al., "Metabolism of fluorine-containing drugs," Annu. Rev. of Pharmacol. and Toxicol., 41:443-470, 2001.
Blattner et al., "Hypophosphorylation of Mdm2 Augments p52 Stability", Mol. Cell. Biol. 22: 6170-6182, 2002.
International Preliminary Report relating to International Patent Application No. PCT/EP2008/062433, dated Mar. 24, 2010.
International Search Report and the Written Opinion of the International Searching Authority relating to International Patent Application No. PCT/EP2008/062433, filed Sep. 18, 2008. dated Jan. 26, 2009.

(Continued)

*Primary Examiner* — Yevgeny Valenrod
(74) *Attorney, Agent, or Firm* — BakerHostetler

(57) ABSTRACT

The present invention provides compounds of formula (I), their use as an inhibitor of a p53-MDM2 interaction as well as pharmaceutical compositions comprising said compounds:

(I)

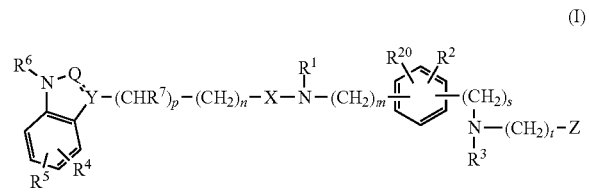

wherein n, m, p, s, t, $R^1$, $R^2$, $R^3$, $R^4$, $R^5$, $R^6$, $R^7$, $R^{20}$, X, Y, Q and Z have defined meanings.

21 Claims, No Drawings

(56) References Cited

OTHER PUBLICATIONS

Morissette et al., "High-throughput crystallization: polymorphs, salts, co-crystals and solvates of pharmaceutical solids," Advanced Drug Delivery Reviews, 56: 275-300, 2004.
Patani, George A. and Lavoie, Edmond J, "Bioisosterism: A Rational Approach in Drug Design," Chem. Rev., 96: 3147-3176, 1996.
Vippagunta et al., Crystalline solids, Advanced Drug Delivery Reviews, 48: 3-26, 2001.
Vousden, K.H., "p53: Death Star", Cell 103(5): 691-694, 2000.

* cited by examiner

INHIBITORS OF THE INTERACTION BETWEEN MDM2 AND P53

CROSS-REFERENCE TO RELATED APPLICATIONS

This application is a continuation of U.S. patent application Ser. No. 15/982,043, filed May 17, 2018, which is a divisional of U.S. patent application Ser. No. 15/398,291, filed Jan. 4, 2017, which is a divisional of U.S. patent application Ser. No. 12/678,961, filed Mar. 18, 2010, now U.S. Pat. No. 9,573,933, which is a U.S. national stage of International Patent Application No. PCT/EP2008/062433, filed Sep. 18, 2008, which claims priority to European Patent Application No. 07116889.2, filed Sep. 21, 2007, the entire disclosures of which are hereby incorporated by reference in their entireties.

FIELD OF THE INVENTION

The present invention relates to compounds and compositions containing said compounds acting as inhibitors of the interaction between MDM2 and p53, in particular modulators of the MDM2-proteasome interaction. The invention also provides processes for the preparation of the disclosed compounds and compositions and methods of using them, for instance as a medicine.

p53 is a tumour suppressor protein which plays a pivotal role in the regulation of the balance between cell proliferation and cell growth arrest/apoptosis. Under normal conditions the half life of p53 is very short and consequently the level of p53 in cells is low. However, in response to cellular DNA damage or cellular stress (e.g. oncogene activation, telomere erosion, hypoxia), levels of p53 increase. This increase in p53 levels leads to the activation of the transcription of a number of genes which drives the cell into either growth arrest or into the processes of apoptosis. Thus, an important function of p53 is to prevent the uncontrolled proliferation of damaged cells and thus protect the organism from the development of cancer.

MDM2 is a key negative regulator of p53 function. It forms a negative autoregulatory loop by binding to the amino terminal transactivation domain of p53 and thus MDM2 both inhibits the ability of p53 to activate transcription and targets p53 for proteolytic degradation. Under normal conditions this regulatory loop is responsible for maintaining the low levels of p53. However, in tumours with wild-type p53, the equilibrium concentration of active p53 can be increased by antagonising the interaction between MDM2 and p53. Other activities of MDM2 are also required for p53 degradation, as evidenced by the accumulation of ubiquitylated p53 when phosphorylation in the central domain of HDM2 is abrogated (Blattner et al., Hypophosphorylation of Mdm2 augments p53 stability. (2002) *Mol. Cell. Biol.*, 22, 6170-6182). The association of HDM2 with different subunits of the 26S proteasome such as S4, S5a, S6a and S6b (3$^{rd}$ Mdm2 workshop, September 2005 in Constance, Germany) might play a key role in this process. Thus, p53 concentrations can also be increased by modulating the MDM2-proteasome interaction. This will result in restoration of the p53-mediated pro-apoptotic and anti-proliferative effects in such tumour cells. MDM2 antagonists might even exhibit anti-proliferative effects in tumour cells that are devoid of functional p53.

This positions the HDM2 protein as an attractive target for the development of anti-cancer therapy.

MDM2 is a cellular proto-oncogene. Over-expression of MDM2 has been observed in a range of cancers. MDM2 is over-expressed in a variety of tumours due to gene amplification or increased transcription or translation. The mechanism by which MDM2 amplification promotes tumourigenesis is at least in part related to its interaction with p53. In cells over-expressing MDM2 the protective function of p53 is blocked and thus cells are unable to respond to DNA damage or cellular stress by increasing p53 levels, leading to cell growth arrest and/or apoptosis. Thus after DNA damage and/or cellular stress, cells over-expressing MDM2 are free to continue to proliferate and assume a tumorigenic phenotype. Under these conditions disruption of the interaction of p53 and MDM2 would release the p53 and thus allow normal signals of growth arrest and/or apoptosis to function.

MDM2 may also have separate functions in addition to inhibition of p53. The number of MDM2 substrates is rapidly expanding. For example, it has been shown that MDM2 interacts directly with the pRb-regulated transcription factor E2F1/DP1. This interaction could be crucial for the p53-independent oncogenic activities of MDM2. A domain of E2F1 shows striking similarity to the MDM2-binding domain of p53. Since the interactions of MDM2 with both p53 and E2F1 locate to the same binding site on MDM2, it can be expected that MDM2/p53 antagonists will not only activate cellular p53 but also modulate E2F1 activities, which are commonly deregulated in tumour cells. Other key examples of MDM2 substrates include p63, p73, p21$^{waf1,cip1}$.

Also the therapeutic effectiveness of DNA damaging agents currently used (chemotherapy and radiotherapy), may be limited through the negative regulation of p53 by MDM2. Thus if the MDM2 feed-back inhibition of p53 is interrupted, an increase in functional p53 levels will increase the therapeutic effectiveness of such agents by restoring the wild-type p53 function that leads to apoptosis and/or reversing of p53-associated drug resistance. It was demonstrated that combining MDM2 inhibition and DNA-damaging treatments in vivo led to synergistic anti-tumour effects (Vousden K. H., Cell, Vol. 103, 691-694, 2000).

Thus disruption of the interaction of MDM2 and p53 offers an approach for therapeutic intervention in tumours with wild-type or mutant p53, might even exhibit anti-proliferative effects in tumour cells that are devoid of functional p53 and furthermore can sensitise tumorigenic cells for chemotherapy and radiotherapy.

BACKGROUND OF THE INVENTION

WO 2006/032631 discloses inhibitors of the interaction between MDM2 and p53, useful inter alia in treating tumours and enhancing the effectiveness of chemotherapy and radiotherapy.

The compounds of the instant invention differ structurally from the compounds of WO 2006/032631 by comprising an additional substituent R$^{20}$ on the central phenyl ring.

WO 2007/107543 also discloses inhibitors of the interaction between MDM2 and p53, useful inter alia in treating tumours and enhancing the effectiveness of chemotherapy and radiotherapy.

Unexpectedly, the substantial structural modifications in the present compounds do not impair the activity of the present compounds. Hence, the invention provides a further useful series of effective and potent small molecules that inhibit the interactions between MDM2 and p53 and that are drugable.

DESCRIPTION OF THE INVENTION

The present invention provides compounds and compositions for, and methods of, inhibiting the interactions between MDM2 and p53 for treating proliferative disease, including tumours and cancer. Furthermore, the compounds and compositions of the invention are useful in enhancing the effectiveness of chemotherapy and radiotherapy.

Accordingly, in an aspect the invention provides a compound of formula (I):

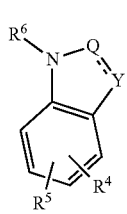

(I)

including any stereochemically isomeric form thereof, wherein m is 0, 1 or 2 and when m is 0 then a direct bond is intended;

n is 0, 1, 2 or 3 and when n is 0 then a direct bond is intended;

p is 0 or 1 and when p is 0 then a direct bond is intended;

s is 0 or 1 and when s is 0 then a direct bond is intended;

t is 0 or 1 and when t is 0 then a direct bond is intended;

X is C(=O) or $CHR^8$, wherein $R^8$ is selected from hydrogen; $C_{1-6}$alkyl; $C_{3-7}$cycloalkyl; —C(=O)—$NR^{17}R^{18}$; carboxyl; aryl$C_{1-6}$alkyloxycarbonyl; heteroaryl; heteroarylcarbonyl; heteroaryl$C_{1-6}$alkyloxycarbonyl; piperazinylcarbonyl; pyrrolidinyl; piperidinylcarbonyl; $C_{1-6}$alkyloxycarbonyl; $C_{1-6}$alkyl substituted with a substituent selected from hydroxy, amino, aryl and heteroaryl; $C_{3-7}$ cycloalkyl substituted with a substituent selected from hydroxy, amino, aryl and heteroaryl; piperazinylcarbonyl substituted with a substituent selected from hydroxy, hydroxy$C_{1-6}$alkyl and hydroxy$C_{1-6}$alkyloxy$C_{1-6}$alkyl; pyrrolidinyl substituted with hydroxy$C_{1-6}$alkyl; and piperidinylcarbonyl substituted with one or two substituents selected from hydroxy, $C_{1-6}$alkyl, hydroxy$C_{1-6}$alkyl, $C_{1-6}$alkyloxy$C_{1-6}$alkyl, $C_{1-6}$alkyl(dihydroxy)$C_{1-6}$alkyl and $C_{1-6}$alkyloxy(hydroxy)$C_{1-6}$alkyl;

$R^{17}$ and $R^{18}$ are each independently selected from hydrogen, $C_{1-6}$alkyl, di($C_{1-6}$alkyl)amino$C_{1-6}$alkyl, aryl$C_{1-6}$alkyl, $C_{1-6}$alkyloxy$C_{1-6}$alkyl, hydroxy$C_{1-6}$alkyl, hydroxy$C_{1-6}$alkyl($C_{1-6}$alkyl), or hydroxy$C_{1-6}$alkyl(aryl$C_{1-6}$alkyl);

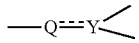

is —$CR^9$=C< and then the dotted line is a bond, —C(=O)—CH<, —C(=O)—N<, —$CHR^9$—CH<, or —$CHR^9$—N<, wherein each $R^9$ is independently hydrogen or $C_{1-6}$alkyl, or wherein $R^9$ together with one of $R^2$ or $R^{20}$ form a direct bond;

$R^1$ is hydrogen; aryl; heteroaryl; $C_{1-6}$alkyloxycarbonyl; $C_{1-12}$alkyl; or $C_{1-12}$alkyl substituted with one or two substituents independently selected from hydroxy, aryl, heteroaryl, amino, $C_{1-6}$alkyloxy, mono- or di($C_{1-6}$alkyl)amino, morpholinyl, piperidinyl, pyrrolidinyl, piperazinyl, $C_{1-6}$alkylpiperazinyl, aryl$C_{1-6}$alkylpiperazinyl, heteroaryl$C_{1-6}$alkylpiperazinyl, $C_{3-7}$cycloalkyl-piperazinyl and $C_{3-7}$cycloalkyl$C_{1-6}$alkylpiperazinyl;

$R^2$ and $R^{20}$ are each independently selected from halo, hydroxy, cyano, nitro, carboxyl; polyhalo$C_{1-6}$alkyl, polyhalo$C_{1-6}$alkyloxy; $C_{1-6}$alkyl, $C_{3-7}$cycloalkyl, $C_{2-6}$alkenyl, aryl, heteroaryl, aryl$C_{1-6}$alkyl, heteroaryl-$C_{1-6}$alkyl, $C_{3-7}$cycloalkyl $C_{1-6}$alkyl, morpholinyl, piperidinyl, pyrrolidinyl, piperazinyl, $C_{1-6}$alkyloxy, aryloxy, heteroaryloxy, $C_{1-6}$alkylthio, arylthio, heteroarylthio, $C_{1-6}$alkylcarbonyl, $C_{3-7}$cycloalkylcarbonyl, arylcarbonyl, heteroarylcarbonyl, $C_{1-6}$alkyloxycarbonyl, $C_{3-7}$cycloalkyloxycarbonyl, aryloxycarbonyl, heteroaryloxycarbonyl, $C_{1-6}$alkylcarbonyloxy, $C_{3-7}$cycloalkylcarbonyloxy, arylcarbonyloxy or heteroarylcarbonyloxy, any of said groups being optionally and independently substituted with one or more, preferably one or two, substituents selected from halo, hydroxy, cyano, nitro, carboxyl, amino, mono- or di($C_{1-6}$alkyl)amino, $C_{1-6}$alkyl, polyhalo$C_{1-6}$alkyl, aryl, heteroaryl, $C_{1-6}$alkyloxy, $C_{1-6}$alkylcarbonyl, $C_{1-6}$alkyloxycarbonyl and $C_{1-6}$alkylcarbonyloxy; and —$(CH_2)_w$—$(C(=O))_y NR^{21}R^{22}$ wherein w is 0, 1, 2, 3, 4, 5 or 6 and when w is 0 then a direct bond is intended;

y is 0 or 1 and when y is 0 then a direct bond is intended;

$R^{21}$ and $R^{22}$ are each independently selected from hydrogen, $C_{1-6}$alkyl, $C_{3-7}$cycloalkyl, $C_{1-6}$alkylcarbonyl and aryl$C_{1-6}$alkylcarbonyl, any of said groups being optionally and independently substituted with one or more, preferably one or two, substituents selected from halo, hydroxy, amino, mono- or di($C_{1-6}$alkyl)amino, $C_{1-6}$alkyl, polyhalo$C_{1-6}$alkyl, $C_{1-6}$alkyloxy, aryl and heteroaryl;

or $R^{21}$ and $R^{22}$ together with the nitrogen to which they are attached form morpholinyl, piperidinyl, pyrrolidinyl or piperazinyl, any of said groups being optionally and independently substituted with one or more, preferably one or two, substituents selected from $C_{1-6}$alkyl, polyhalo$C_{1-6}$alkyl, $C_{1-6}$alkyloxy, $C_{3-7}$cycloalkyl, $C_{3-7}$cycloalkyl$C_{1-6}$alkyl, aryl$C_{1-6}$alkyl and heteroaryl$C_{1-6}$alkyl;

or $R^2$ and $R^{20}$ together with the phenyl ring to which they are attached form a naphthalenyl group, optionally substituted with one or more, preferably one or two, substituents each independently selected from halo, hydroxy, amino, mono- or di($C_{1-6}$alkyl)amino, $C_{1-6}$alkyl, polyhalo$C_{1-6}$alkyl, $C_{1-6}$alkyloxy, aryl and heteroaryl;

or $R^2$ and $R^{20}$ together form a bivalent radical of the formula —$(CH_2)_b$— wherein b is 3, 4 or 5, optionally substituted with one or more, preferably one or two, substituents selected from halo, hydroxy, amino, mono- or di($C_{1-6}$alkyl)amino, $C_{1-6}$alkyl, polyhalo$C_{1-6}$alkyl, $C_{1-6}$alkyloxy, aryl and heteroaryl;

or one of $R^2$ or $R^{20}$ is as defined above and the other one of $R^2$ or $R^{20}$ together with $R^9$ form a direct bond;

$R^3$ is hydrogen; $C_{1-6}$alkyl; heteroaryl; $C_{3-7}$cycloalkyl; $C_{1-6}$alkyl substituted with a substituent selected from hydroxy, amino, aryl and heteroaryl; or $C_{3-7}$cycloalkyl substituted with a substituent selected from hydroxy, amino, aryl and heteroaryl;

$R^4$ and $R^5$ are each independently hydrogen, halo, $C_{1-6}$alkyl, hydroxy$C_{1-6}$alkyl, polyhalo-$C_{1-6}$alkyl, cyano, cyano $C_{1-6}$alkyl, hydroxy, amino, $C_{2-6}$alkenyl or $C_{1-6}$alkyloxy; or $R^4$ and $R^5$ together form a bivalent radical selected from methylenedioxy or ethylenedioxy;

$R^6$ is hydrogen, $C_{1-6}$alkyloxycarbonyl, or $C_{1-6}$alkyl;

when p is 1 then $R^7$ is hydrogen, aryl$C_{1-6}$alkyl, hydroxy, or heteroaryl$C_{1-6}$alkyl;

Z is a radical selected from (a-1)

(a-2)

(a-3)

(a-4)

(a-5)

(a-6)

(a-7)

(a-8)

(a-9)

wherein $R^{10}$ or $R^{11}$ are each independently selected from hydrogen, halo, hydroxy, amino, $C_{1-6}$alkyl, nitro, polyhalo$C_{1-6}$alkyl, cyano, cyano$C_{1-6}$alkyl, tetrazolo$C_{1-6}$alkyl, aryl, heteroaryl, aryl$C_{1-6}$alkyl, heteroaryl$C_{1-6}$alkyl, aryl(hydroxy)$C_{1-6}$alkyl, heteroaryl(hydroxy)$C_{1-6}$alkyl, arylcarbonyl, heteroarylcarbonyl, $C_{1-6}$alkylcarbonyl, aryl$C_{1-6}$alkylcarbonyl, heteroaryl$C_{1-6}$alkylcarbonyl, $C_{1-6}$alkyloxy, $C_{3-7}$cycloalkylcarbonyl, $C_{3-7}$cycloalkyl(hydroxy)$C_{1-6}$alkyl, aryl$C_{1-6}$alkyloxy$C_{1-6}$alkyl, $C_{1-6}$alkyloxy$C_{1-6}$alkyloxy$C_{1-6}$alkyl, $C_{1-6}$alkylcarbonyloxy$C_{1-6}$alkyl, $C_{1-6}$alkyloxycarbonyl$C_{1-6}$alkyloxy $C_{1-6}$alkyl, hydroxy$C_{1-6}$alkyloxy$C_{1-6}$alkyl, $C_{1-6}$alkyloxycarbonyl$C_{2-6}$alkenyl, $C_{1-6}$alkyloxy$C_{1-6}$alkyl, $C_{1-6}$alkyloxycarbonyl, $C_{1-6}$alkylcarbonyloxy, aminocarbonyl, hydroxy$C_{1-6}$alkyl, amino$C_{1-6}$alkyl, hydroxycarbonyl, hydroxycarbonyl$C_{1-6}$alkyl and —$(CH_2)_v$—$(C(=O))_r$—$(CHR^{19})_u$—$NR^{13}R^{14}$, wherein v is 0, 1, 2, 3, 4, 5, or 6 and when v is 0 then a direct bond is intended;

r is 0 or 1 and when r is 0 then a direct bond is intended;

u is 0, 1, 2, 3, 4, 5, or 6 and when u is 0 then a direct bond is intended;

$R^{19}$ is hydrogen or $C_{1-6}$alkyl;

$R^{13}$ and $R^{14}$ are each independently selected from hydrogen; $C_{1-12}$alkyl; $C_{1-6}$alkylcarbonyl; $C_{1-6}$alkylsulfonyl; aryl$C_{1-6}$alkylcarbonyl; $C_{3-7}$cycloalkyl; $C_{3-7}$cycloalkylcarbonyl; —$(CH_2)_k$—$NR^{15}R^{18}$; $C_{1-12}$alkyl substituted with a substituent selected from hydroxy, hydroxycarbonyl, cyano, $C_{1-6}$alkyloxycarbonyl, $C_{1-6}$alkyloxy, aryl or heteroaryl; or $C_{3-7}$cycloalkyl substituted with a substituent selected from hydroxy, $C_{1-6}$alkyloxy, aryl, amino, aryl$C_{1-6}$alkyl, heteroaryl or heteroaryl$C_{1-6}$alkyl; or $R^{13}$ and $R^{14}$ together with the nitrogen to which they are attached form morpholinyl, piperidinyl, pyrrolidinyl, piperazinyl, or piperazinyl substituted with a substituent selected from $C_{1-6}$alkyl, aryl$C_{1-6}$alkyl, aryl$C_{1-6}$alkyloxycarbonyl, heteroaryl$C_{1-6}$alkyl, $C_{3-7}$cycloalkyl and $C_{3-7}$cycloalkyl$C_{1-6}$alkyl; wherein k is 0, 1, 2, 3, 4, 5, or 6 and when k is 0 then a direct bond is intended;

$R^{15}$ and $R^{16}$ are each independently selected from hydrogen; $C_{1-12}$alkyl; aryl$C_{1-6}$alkyloxycarbonyl; $C_{3-7}$cycloalkyl; $C_{1-12}$alkyl substituted with a substituent selected from hydroxy, $C_{1-6}$alkyloxy, aryl, and heteroaryl; and $C_{3-7}$cycloalkyl substituted with a substituent selected from hydroxy, $C_{1-6}$alkyloxy, aryl, aryl$C_{1-6}$alkyl, heteroaryl, and heteroaryl$C_{1-6}$alkyl; or $R^{15}$ and $R^{18}$ together with the nitrogen to which they are attached form morpholinyl, piperazinyl, or piperazinyl substituted with $C_{1-6}$alkyloxycarbonyl;

$R^{12}$ is hydrogen; $C_{1-6}$alkyl; $C_{3-7}$cycloalkyl; $C_{1-6}$alkyl substituted with a substituent selected from hydroxy, amino, $C_{1-6}$alkyloxy and aryl; or $C_{3-7}$cycloalkyl substituted with a substituent selected from hydroxy, amino, aryl and $C_{1-6}$alkyloxy;

aryl is phenyl or naphthalenyl;

each phenyl or naphthalenyl can optionally be substituted with one, two or three substituents each independently selected from halo, hydroxy, $C_{1-6}$alkyl, amino, polyhalo$C_{1-6}$alkyl and $C_{1-6}$alkyloxy; and each phenyl or naphthalenyl can optionally be substituted with a bivalent radical selected from methylenedioxy and ethylenedioxy;

heteroaryl is pyridinyl, indolyl, quinolinyl, imidazolyl, furanyl, thienyl, oxadiazolyl, tetrazolyl, benzofuranyl or tetrahydrofuranyl;

each pyridinyl, indolyl, quinolinyl, imidazolyl, furanyl, thienyl, oxadiazolyl, tetrazolyl, benzofuranyl, or tetrahydrofuranyl can optionally be substituted with one, two or three substituents each independently selected from halo, hydroxy, $C_{1-6}$alkyl, amino, polyhalo$C_{1-6}$alkyl, aryl, aryl$C_{1-6}$alkyl or $C_{1-6}$alkyloxy; or each pyridinyl, indolyl, quinolinyl, imidazolyl, furanyl, thienyl, benzofuranyl, or tetrahydrofuranyl can optionally be substituted with a bivalent radical selected from methylenedioxy or ethylenedioxy;

an N-oxide form thereof, an addition salt thereof or a solvate thereof.

The compounds of formula (I) may also exist in their tautomeric forms. Such forms although not explicitly indicated in the above formula are intended to be included within the scope of the present invention.

A number of terms used in the foregoing definitions and hereinafter are explained hereunder. These terms may be used as such or in composite terms.

As used herein, halo is generic to fluoro, chloro, bromo and iodo. $C_{1-6}$alkyl defines straight- and branched-chain saturated hydrocarbon radicals having from 1 to 6 carbon atoms such as, e.g., methyl, ethyl, propyl, butyl, pentyl, hexyl, 1-methylethyl, 2-methylpropyl, 2-methyl-butyl, 2-methylpentyl and the like. $C_{1-12}$ alkyl includes $C_{1-6}$alkyl and the higher straight- and branched-chain homologues thereof having 7 to 12 carbon atoms such as, for example, heptyl, octyl, nonyl, decyl, undecyl, dodecyl and the like. Hydroxy$C_{1-6}$alkyl refers to a $C_{1-6}$alkyl as defined herein, wherein one or more (e.g., one, two, three or more) hydrogens of said $C_{1-6}$alkyl are replaced with a hydroxyl substituent. Polyhalo$C_{1-6}$alkyl and polyhalo-$C_{1-6}$alkyloxy refers respectively to a $C_{1-6}$alkyl or a $C_{1-6}$alkyloxy as defined herein, wherein one, two or more hydrogens of said $C_{1-6}$alkyl or $C_{1-6}$alkyloxy are replaced with identical or different halo substituents; the respective terms polyhalo$C_{1-6}$alkyl and polyhalo$C_{1-6}$alkyloxy also encompass perhalo$C_{1-6}$alkyl and perhalo$C_{1-6}$alkyloxy, i.e., $C_{1-6}$alkyl and $C_{1-6}$alkyloxy as defined herein, wherein all hydrogens of said $C_{1-6}$alkyl or $C_{1-6}$alkyloxy are replaced with identical or different halogen substituents—for example, trihalomethyl defines methyl containing three identical or different halo substituents, such as, e.g., trifluoromethyl, or for example, trihalomethyloxy defines methyloxy containing three identical or different halo substituents, such as, e.g., trifluoromethyloxy. $C_{2-6}$alkenyl defines straight- and branched-chain hydrocarbon radicals containing one or more double bonds, preferably one double bond, and having from 2 to 6 carbon atoms such as, for example, ethenyl, 2-propenyl, 3-butenyl, 2-pentenyl, 3-pentenyl, 3-methyl-2-butenyl, and the like. $C_{3-7}$cycloalkyl includes alicyclic saturated and unsaturated hydrocarbon groups having from 3 to 7 carbon atoms, such as cyclopropyl, cyclobutyl, cyclopentyl, cyclopentenyl, cyclohexyl, cyclohexenyl, cycloheptyl, and the like. Preferably $C_{3-7}$cycloalkyl includes alicyclic saturated hydrocarbon groups having from 3 to 7 carbon atoms, such as cyclopropyl, cyclobutyl, cyclopentyl, cyclohexyl, cycloheptyl, and the like.

The term "addition salt" comprises the salts which the compounds of formula (I) are able to form with organic or inorganic bases such as amines, alkali metal bases and earth alkaline metal bases, or quaternary ammonium bases, or with organic or inorganic acids, such as mineral acids, sulfonic acids, carboxylic acids or phosphorus containing acids.

The term "addition salt" further comprises pharmaceutically acceptable salts, metal complexes and the salts thereof, that the compounds of formula (I) are able to form.

The term "pharmaceutically acceptable salts" means pharmaceutically acceptable acid or base addition salts. The pharmaceutically acceptable acid or base addition salts as mentioned hereinabove are meant to comprise the therapeutically active non-toxic acid and non-toxic base addition salt forms which the compounds of formula (I) are able to form. The compounds of formula (I) which have basic properties can be converted in their pharmaceutically acceptable acid addition salts by treating said base form with an appropriate acid. Appropriate acids comprise, for example, inorganic acids such as hydrohalic acids, e.g., hydrochloric or hydrobromic acid, sulphuric, nitric, phosphoric and the like acids; or organic acids such as, for example, acetic, propanoic, hydroxyacetic, lactic, pyruvic, oxalic, malonic, succinic (i.e., butanedioic acid), maleic, fumaric, malic, tartaric, citric, methanesulfonic, ethanesulfonic, benzenesulfonic, p-toluenesulfonic, cyclamic, salicylic, p-aminosalicylic, pamoic and the like acids.

The compounds of formula (I) which have acidic properties may be converted in their pharmaceutically acceptable base addition salts by treating said acid form with a suitable organic or inorganic base. Appropriate base salt forms comprise, for example, the ammonium salts, the alkali and earth alkaline metal salts, e.g., the lithium, sodium, potassium, magnesium, calcium salts and the like, salts with organic bases, e.g., the benzathine, N-methyl-D-glucamine, hydrabamine salts, and salts with amino acids such as, for example, arginine, lysine and the like.

Preferably, the term addition salt means a pharmaceutically acceptable acid or base addition salt.

The term "metal complexes" means a complex formed between a compound of formula (I) and one or more organic or inorganic metal salt or salts. Examples of said organic or inorganic salts comprise the halogenides, nitrates, sulfates, phosphates, acetates, trifluoroacetates, trichloroacetates, propionates, tartrates, sulfonates, e.g., methylsulfonates, 4-methylphenylsulfonates, salicylates, benzoates and the like of the metals of the second main group of the periodical system, e.g., the magnesium or calcium salts, of the third or fourth main group, e.g., aluminium, tin, lead, as well as the first to the eighth transition groups of the periodical system such as, for example, chromium, manganese, iron, cobalt, nickel, copper, zinc and the like.

The term "stereochemically isomeric forms of compounds of formula (I)", as used herein, defines all possible compounds made up of the same atoms bonded by the same sequence of bonds but having different three-dimensional structures which are not interchangeable, which the compounds of formula (I) may possess. Unless otherwise mentioned or indicated, the chemical designation of a compound encompasses the mixture of all possible stereochemically isomeric forms which said compound may possess. Said mixture may contain all diastereomers and/or enantiomers of the basic molecular structure of said compound. All stereochemically isomeric forms of the compounds of formula (I) both in pure form or in admixture with each other are intended to be embraced within the scope of the present invention.

Of special interest are those compounds of formula (I) which are stereochemically pure. Pure stereoisomeric forms of the compounds and intermediates as mentioned herein are defined as isomers substantially free of other enantiomeric or diastereomeric forms of the same basic molecular structure of said compounds or intermediates. In particular, the term "stereoisomerically pure" concerns compounds or intermediates having a stereoisomeric excess of at least 80% (i.e., minimum 90% of one isomer and maximum 10% of the other possible isomers) up to a stereoisomeric excess of 100% (i.e., 100% of one isomer and none of the other), more preferably, compounds or intermediates having a stereoisomeric excess of 90% up to 100%, even more preferably having a stereoisomeric excess of 94% up to 100% and most preferably having a stereoisomeric excess of 97% up to 100%. The terms "enantiomerically pure" and "diastereomerically pure" should be understood in a similar way, but then having regard to the enantiomeric excess respectively diastereomeric excess of the mixture in question.

The N-oxide forms of the compounds of formula (I) are meant to comprise those compounds of formula (I) wherein one or several tertiary nitrogen atoms are oxidized to the so-called N-oxide, particularly those N-oxides wherein one or more of the piperidine-, piperazine- or pyridazinyl-nitrogens are N-oxidized.

The compounds of formula (I) may be converted to the corresponding N-oxide forms following art-known procedures for converting a trivalent nitrogen into its N-oxide form. Said N-oxidation reaction may generally be carried out by reacting the starting material of formula (I) with an appropriate organic or inorganic peroxide. Appropriate inorganic peroxides comprise, for example, hydrogen peroxide, alkali metal or earth alkaline metal peroxides, e.g., sodium peroxide, potassium peroxide; appropriate organic peroxides may comprise inter alia peroxy acids such as, for example, benzenecarboperoxoic acid or halo substituted benzenecarboperoxoic acid, e.g., 3-chlorobenzenecarboperoxoic acid, peroxoalkanoic acids, e.g., peroxoacetic acid, alkylhydroperoxides, e.g., t-butyl hydro-peroxide. Suitable solvents are, for example, water, lower alcohols, e.g. ethanol and the like, hydrocarbons, e.g. toluene, ketones, e.g. 2-butanone, halogenated hydrocarbons, e.g. dichloromethane, and mixtures of such solvents.

The compounds of formula (I) may form solvates, for example, with water (i.e., hydrates) or common organic solvents e.g. alcohols. As used herein, the term "solvate" means a physical association of the compounds of formula (I) with one or more solvent molecules, as well as the salts thereof. This physical association involves varying degrees of ionic and other bonding, including hydrogen bonding. In certain instances the solvate will be capable of isolation, for example, when one or more solvent molecules are incorporated in the crystal lattice of the crystalline solid. The term "solvate" is intended to encompass both solution-phase and isolatable solvates. Non-limiting examples of suitable solvates include hydrates, ethanolates, methanolates, and the like.

Furthermore, the compounds of the present invention may be amorphous or may have one or more crystalline polymorph forms, as such forms are intended to be included in the scope of the invention.

The invention encompasses any isotopes of atoms present in the compounds of the invention. For example, isotopes of hydrogen include tritium and deuterium and isotopes of carbon include $^{13}C$ and $^{14}C$.

Whenever used hereinafter, the term "compounds of formula (I)" is meant to include also the N-oxide forms, the acid or base addition salts particularly the pharmaceutically acceptable acid or base addition salts, the solvates and all stereoisomeric forms of said compounds of formula (I).

A first group of interesting compounds (herein referred to as group "G1") consists of those compounds of formula (I) wherein any one or more or all of the following restrictions apply:
  a) X is C(=O) or CHR$^8$, wherein
     R$^8$ is selected from hydrogen; $C_{1-6}$alkyl; $C_{3-7}$cycloalkyl; aminocarbonyl; mono- or di($C_{1-6}$alkyl)aminocarbonyl; carboxyl; aryl$C_{1-6}$alkyloxycarbonyl; heteroaryl$C_{1-6}$alkyloxycarbonyl; $C_{1-6}$alkyloxycarbonyl; $C_{1-6}$alkyl substituted with a substituent selected from hydroxy, amino, aryl, and heteroaryl; or $C_{3-7}$cycloalkyl substituted with a substituent selected from hydroxy, amino, aryl and heteroaryl;
  b) R$^1$ is hydrogen; aryl; heteroaryl; $C_{1-12}$alkyl; or $C_{1-12}$alkyl substituted with one or two substituents independently selected from hydroxy, aryl, heteroaryl, amino, $C_{1-6}$alkyloxy, mono- or di($C_{1-6}$alkyl)amino, morpholinyl, piperidinyl, pyrrolidinyl, piperazinyl, $C_{1-6}$alkylpiperazinyl, aryl$C_{1-6}$alkylpiperazinyl, heteroaryl$C_{1-6}$alkylpiperazinyl, $C_{3-7}$cycloalkylpiperazinyl and $C_{3-7}$cycloalkyl$C_{1-6}$alkylpiperazinyl;
  c) R$^3$ is hydrogen; $C_{1-6}$alkyl; $C_{3-7}$cycloalkyl; $C_{1-6}$alkyl substituted with a substituent selected from hydroxy, amino, aryl, and heteroaryl; or $C_{3-7}$cycloalkyl substituted with a substituent selected from hydroxy, amino, aryl and heteroaryl;
  d) R$^4$ and R$^5$ are each independently hydrogen, halo, $C_{1-6}$alkyl, hydroxy$C_{1-6}$alkyl, polyhalo$C_{1-6}$alkyl, hydroxy, amino, $C_{2-6}$alkenyl or $C_{1-6}$alkyloxy; in particular R$^4$ and R$^5$ are each independently hydrogen, halo, $C_{1-6}$alkyl, polyhalo$C_{1-6}$alkyl, hydroxy, amino or $C_{1-6}$alkyloxy;
  e) R$^4$ and R$^5$ together form a bivalent radical selected from methylenedioxy or ethylenedioxy;
  f) R$^6$ is hydrogen or $C_{1-6}$alkyl;
  g) when p is 1 then R$^7$ is hydrogen, aryl$C_{1-6}$alkyl or heteroaryl$C_{1-6}$alkyl;
  h) Z is a radical selected from (a-1), (a-2), (a-3), (a-4) and (a-5);
  i) R$^{10}$ or R$^{11}$ are each independently selected from hydrogen; hydroxyl; amino; $C_{1-6}$alkyl; nitro; polyhalo$C_{1-6}$alkyl; cyano; cyano$C_{1-6}$alkyl; tetrazolo$C_{1-6}$alkyl; aryl; heteroaryl; aryl$C_{1-6}$alkyl; heteroaryl$C_{1-6}$alkyl; aryl(hydroxy)$C_{1-6}$alkyl; heteroaryl(hydroxy)$C_{1-6}$alkyl; arylcarbonyl; heteroarylcarbonyl; aryl$C_{1-6}$alkylcarbonyl; heteroaryl$C_{1-6}$alkylcarbonyl; $C_{1-6}$alkyloxy; $C_{1-6}$alkyloxy$C_{1-6}$alkyl; $C_{1-6}$alkyloxycarbonyl; $C_{1-6}$alkylcarbonyloxy; aminocarbonyl; hydroxy$C_{1-6}$alkyl; amino$C_{1-6}$alkyl; hydroxycarbonyl; hydroxycarbonyl$C_{1-6}$alkyl and —(CH$_2$)$_v$—(C(=O))$_r$—(CH$_2$)$_u$—NR$^{13}$R$^{14}$;

j) $R^{13}$ and $R^{14}$ are each independently selected from hydrogen; $C_{1-12}$alkyl; $C_{3-7}$cycloalkyl; —$(CH_2)_k$—$NR^{15}R^{16}$; $C_{1-12}$alkyl substituted with a substituent selected from hydroxy, $C_{1-6}$alkyloxy, aryl, and heteroaryl; or $C_{3-7}$cycloalkyl substituted with a substituent selected from hydroxy, $C_{1-6}$alkyloxy, aryl, aryl$C_{1-6}$alkyl, heteroaryl and heteroaryl$C_{1-6}$alkyl;

k) $R^{13}$ and $R^{14}$ together with the nitrogen to which they are attached form morpholinyl, piperidinyl, pyrrolidinyl, piperazinyl, or piperazinyl substituted with a substituent selected from $C_{1-6}$alkyl, aryl$C_{1-6}$alkyl, heteroaryl$C_{1-6}$alkyl, $C_{3-7}$cycloalkyl, and $C_{3-7}$cycloalkyl$C_{1-6}$alkyl;

l) $R^{15}$ and $R^{16}$ are each independently selected from hydrogen; $C_{1-12}$alkyl; $C_{3-7}$cycloalkyl; $C_{1-12}$alkyl substituted with a substituent selected from hydroxy, $C_{1-6}$alkyloxy, aryl, and heteroaryl; and $C_{3-7}$cycloalkyl substituted with a substituent selected from hydroxy, $C_{1-6}$alkyloxy, aryl, aryl$C_{1-6}$alkyl, heteroaryl and heteroaryl$C_{1-6}$alkyl; in particular $R^{15}$ and $R^{16}$ are each independently selected from hydrogen; $C_{1-6}$alkyl; $C_{3-7}$cycloalkyl; $C_{1-12}$ alkyl substituted with a substituent selected from hydroxy, $C_{1-6}$alkyloxy, aryl, and heteroaryl; and $C_{3-7}$cycloalkyl substituted with a substituent selected from hydroxy, $C_{1-6}$alkyloxy, aryl, aryl$C_{1-6}$alkyl, heteroaryl and heteroaryl$C_{1-6}$alkyl;

m) heteroaryl is pyridinyl, indolyl, quinolinyl, imidazolyl, furanyl, thienyl, benzofuranyl, or tetrahydrofuranyl; and each pyridinyl, indolyl, quinolinyl, imidazolyl, furanyl, thienyl, benzofuranyl, or tetrahydrofuranyl can optionally be substituted with one, two or three substituents each independently selected from halo, hydroxy, $C_{1-6}$alkyl, amino, polyhalo$C_{1-6}$alkyl and $C_{1-6}$alkyloxy; and n) each pyridinyl, indolyl, quinolinyl, imidazolyl, furanyl, thienyl, benzofuranyl, or tetrahydrofuranyl can optionally be substituted with a bivalent radical selected from methylenedioxy or ethylenedioxy.

A second group of interesting compounds (herein referred to as group "G2") consists of those compounds of formula (I) wherein any one or more or all of the following restrictions apply:
a) n is 0, 1 or 2;
b) p is 0;
c) X is C(=O) or CHR$^8$, preferably CHR$^8$, wherein R$^8$ is hydrogen, aminocarbonyl, aryl$C_{1-6}$alkyloxycarbonyl or $C_{1-6}$alkyl substituted with hydroxy;

d)
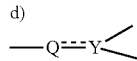

e) $R^1$ is hydrogen, $C_{1-12}$alkyl, or $C_{1-12}$alkyl substituted with heteroaryl;
f) $R^3$ is hydrogen or $C_{1-6}$alkyl;
g) $R^4$ and $R^5$ are each independently hydrogen, halo or $C_{1-6}$alkyloxy;
h) Z is a radical selected from (a-1), (a-2), (a-3) and (a-4);
i) $R^{10}$ or $R^{11}$ are each independently selected from hydrogen, hydroxy, amino, $C_{1-6}$alkyl, nitro, polyhalo$C_{1-6}$alkyl, cyano, aryl, aryl$C_{1-6}$alkyl, aryl(hydroxy)$C_{1-6}$alkyl, arylcarbonyl, $C_{1-6}$alkyloxy, $C_{1-6}$alkyloxy$C_{1-6}$alkyl, $C_{1-6}$alkyloxycarbonyl, aminocarbonyl, hydroxy$C_{1-6}$alkyl, amino$C_{1-6}$alkyl, hydroxycarbonyl and —$(CH_2)_v$—$(C(=O))_r$—$(CH_2)_u$—$NR^{13}R^{14}$;

j) v is 0 or 1;
k) r is 0 or 1;
l) u is 0;
m) $R^{13}$ and $R^{14}$ are each independently selected from hydrogen, $C_{1-6}$alkyl, —$(CH_2)_k$—$NR^{15}R^{16}$ and $C_{1-12}$alkyl substituted with hydroxy;
n) $R^{13}$ and $R^{14}$ together with the nitrogen to which they are attached can form a pyrrolidinyl;
o) k is 2;
p) $R^{15}$ and $R^{16}$ are each independently $C_{1-6}$alkyl;
q) aryl is phenyl or phenyl substituted with halo; and
r) heteroaryl is pyridinyl or indolyl.

A third group of interesting compounds (herein referred to as group "G3") consists of those compounds of formula (I) wherein any one or more or all of the following restrictions apply:
a) m is 0 or 2;
b) n is 0, 2 or 3;
c) p is 1;
d) s is 1;
e) t is 1;
f) X is C(=O);

g)
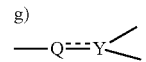

is —C(=O)—CH<, —C(=O)—N<, —CHR$^9$—CH<, or —CHR$^8$—N<;

h) $R^1$ is aryl; heteroaryl; $C_{1-6}$alkyloxycarbonyl; $C_{1-12}$alkyl; or $C_{1-12}$alkyl substituted with one or two substituents independently selected from hydroxy, aryl, heteroaryl, amino, $C_{1-6}$alkyloxy, mono- or di($C_{1-6}$alkyl)amino, morpholinyl, piperidinyl, pyrrolidinyl, piperazinyl, $C_{1-6}$alkylpiperazinyl, aryl$C_{1-6}$alkylpiperazinyl, heteroaryl$C_{1-6}$alkylpiperazinyl, $C_{3-7}$cycloalkylpiperazinyl and $C_{3-7}$cycloalkyl$C_{1-6}$alkylpiperazinyl;

i) $R^3$ is $C_{1-6}$alkyl; $C_{3-7}$cycloalkyl; $C_{1-6}$alkyl substituted with a substituent selected from hydroxy, amino, aryl, and heteroaryl; or $C_{3-7}$cycloalkyl substituted with a substituent selected from hydroxy, amino, aryl and heteroaryl;

j) $R^4$ and $R^5$ are each independently $C_{1-6}$alkyl, polyhalo$C_{1-6}$alkyl, hydroxy$C_{1-6}$alkyl, cyano, cyano$C_{1-6}$alkyl, hydroxyl, amino or $C_{2-6}$alkenyl; in particular $C_{1-6}$alkyl, polyhalo-$C_{1-6}$alkyl, cyano, cyano$C_{1-6}$alkyl, hydroxy or amino;

k) $R^4$ and $R^5$ together form a bivalent radical selected from methylenedioxy or ethylenedioxy;

l) $R^6$ is $C_{1-6}$alkyloxycarbonyl or $C_{1-6}$alkyl;
m) $R^7$ is hydrogen, aryl$C_{1-6}$alkyl, hydroxy or heteroaryl$C_{1-6}$alkyl; and
n) Z is a radical selected from (a-1), (a-3), (a-4), (a-5), (a-6), (a-7) and (a-8).

A fourth group of interesting compounds (herein referred to as group "G4") consists of those compounds of formula (I) wherein any one or more or all of the following restrictions apply:
a) X is C(=O) or CHR$^8$, preferably CHR$^8$, wherein R$^8$ is hydrogen, —C(=O)—NR$^{17}$R$^{18}$, aryl$C_{1-6}$alkyloxycarbonyl, $C_{1-6}$alkyl substituted with hydroxy, piperazinylcarbonyl substituted with hydroxy, hydroxy$C_{1-6}$alkyl, hydroxy$C_{1-6}$alkyloxy$C_{1-6}$alkyl, pyrrolidinyl substituted with hydroxy$C_{1-6}$alkyl or piperidinylcarbonyl substituted with one or two substituents selected from hydroxy, $C_{1-6}$alkyl, hydroxyC$_{1-6}$alkyl, C$_{1-6}$alkyloxyC$_{1-6}$alkyl, C$_{1-6}$alkyl(dihydroxy)C$_{1-6}$alkyl or C$_{1-6}$alkyloxy(hydroxy)C$_{1-6}$alkyl;

b) R$^{17}$ and R$^{18}$ are each independently selected from hydrogen, C$_{1-6}$alkyl, di(C$_{1-6}$alkyl)aminoC$_{1-6}$alkyl, arylC$_{1-6}$alkyl, C$_{1-6}$alkyloxyC$_{1-6}$alkyl and hydroxyC$_{1-6}$alkyl;

c) 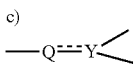

is —CR$^9$=C<, —CHR$^9$—CH< or —CHR$^9$—N<;

d) R$^1$ is hydrogen, heteroaryl, C$_{1-6}$alkyloxycarbonyl, C$_{1-12}$alkyl or C$_{1-12}$alkyl substituted with heteroaryl;

e) R$^3$ is hydrogen, C$_{1-6}$alkyl or heteroaryl;

f) R$^4$ and R$^5$ are each independently hydrogen, halo, C$_{1-6}$alkyl, hydroxyC$_{1-6}$alkyl, cyano, cyanoC$_{1-6}$alkyl, hydroxyl, C$_{2-6}$alkenyl or C$_{1-6}$alkyloxy; in particular hydrogen, halo, C$_{1-6}$alkyl, cyano, cyanoC$_{1-6}$alkyl, hydroxy or C$_{1-6}$alkyloxy;

g) when p is 1 then R$^7$ is arylC$_{1-6}$alkyl or hydroxy;

h) Z is a radical selected from (a-1), (a-2), (a-3), (a-4), (a-5), (a-7), (a-8) and (a-9);

i) R$^{10}$ or R$^{11}$ are each independently selected from hydrogen, halo, hydroxy, amino, C$_{1-6}$alkyl, nitro, polyhaloC$_{1-6}$alkyl, cyano, cyanoC$_{1-6}$alkyl, tetrazoloC$_{1-6}$alkyl, aryl, heteroaryl, heteroarylC$_{1-6}$alkyl, aryl(hydroxy)C$_{1-6}$alkyl, arylcarbonyl, C$_{1-6}$alkylcarbonyl, C$_{3-7}$cycloalkylcarbonyl, C$_{3-7}$cycloalkyl(hydroxy)C$_{1-6}$alkyl, arylC$_{1-6}$alkyloxyC$_{1-6}$alkyl, C$_{1-6}$alkyloxyC$_{1-6}$alkyloxyC$_{1-6}$alkyl, C$_{1-6}$alkylcarbonyloxyC$_{1-6}$alkyl, C$_{1-6}$alkyloxycarbonylC$_{1-6}$alkyloxyC$_{1-6}$alkyl, hydroxyC$_{1-6}$alkyloxyC$_{1-6}$alkyl, C$_{1-6}$alkyloxycarbonylC$_{2-6}$alkenyl, C$_{1-6}$alkyloxyC$_{1-6}$alkyl, C$_{1-6}$alkyloxycarbonyl, aminocarbonyl, hydroxyC$_{1-6}$alkyl, aminoC$_{1-6}$alkyl, hydroxycarbonyl, hydroxycarbonyl-C$_{1-6}$alkyl and —(CH$_2$)$_v$—(C(=O))$_r$—(CHR$^{19}$)$_u$—NR$^{13}$R$^{14}$;

j) v is 0 or 1;

k) u is 0 or 1;

l) R$^{12}$ is hydrogen or C$_{1-6}$alkyl;

m) R$^{13}$ and R$^{14}$ are each independently selected from hydrogen; C$_{1-12}$alkyl; C$_{1-6}$alkylcarbonyl; C$_{1-6}$alkylsulfonyl; arylC$_{1-6}$alkylcarbonyl; C$_{3-7}$cycloalkylcarbonyl; —(CH$_2$)$_k$—NR$^{15}$R$^{16}$; C$_{1-12}$alkyl substituted with a substituent selected from hydroxy, hydroxycarbonyl, cyano, C$_{1-6}$alkyloxycarbonyl or aryl;

n) R$^{13}$ and R$^{14}$ together with the nitrogen to which they are attached form morpholinyl, pyrrolidinyl, piperazinyl, or piperazinyl substituted with a substituent selected from C$_{1-6}$alkyl or arylC$_{1-6}$alkyloxycarbonyl;

o) k is 2;

p) R$^{15}$ and R$^{16}$ are each independently selected from hydrogen, C$_{1-12}$alkyl or arylC$_{1-6}$alkyloxycarbonyl; in particular hydrogen, C$_{1-6}$alkyl or arylC$_{1-6}$alkyloxycarbonyl;

q) R$^{15}$ and R$^{18}$ together with the nitrogen to which they are attached form morpholinyl, a piperazinyl or a piperazinyl substituted with C$_{1-6}$alkyloxycarbonyl;

r) aryl is phenyl or phenyl substituted with halo;

s) heteroaryl is pyridinyl, indolyl, oxadiazolyl or tetrazolyl; and t) each pyridinyl, indolyl, oxadiazolyl or tetrazolyl can optionally be substituted with one substituents selected from C$_{1-6}$alkyl, aryl or arylC$_{1-6}$alkyl.

A fifth group of interesting compounds (herein referred to as group "G5") consists of those compounds of formula (I) wherein any one or more or all, preferably all, of the following restrictions apply:

a) m is 0;
b) n is 1 or 2;
c) p is 0;
d) s is 0;
e) t is 0;
f) X is CHR$^8$;
g) R$^8$ is hydrogen;

h) 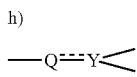

is —CR$^9$=C<;

i) R$^9$ is hydrogen or C$_{1-6}$alkyl;

j) R$^1$ is hydrogen;

k) R$^3$ is hydrogen;

l) R$^4$ and R$^5$ are each independently hydrogen, C$_{1-6}$alkyl, hydroxyC$_{1-6}$alkyl, C$_{2-6}$alkenyl or C$_{1-6}$alkyloxy;

m) R$^6$ is hydrogen;

n) Z is a radical selected from (a-1), (a-2) and (a-4);

o) R$^{10}$ and R$^{11}$ are each independently selected from hydrogen, hydroxy or hydroxyC$_{1-6}$alkyl;

p) R$^2$ and R$^{20}$ are each independently selected from halo, cyano, polyhaloC$_{1-6}$alkyl, C$_{1-6}$alkyl, morpholinyl, C$_{1-6}$alkyloxy, hydroxyC$_{1-6}$alkyl, —NR$^{21}$R$^{22}$ wherein R$^{21}$ is hydrogen and R$^{22}$ is C$_{1-6}$alkylcarbonyl; or R$^2$ and R$^{20}$ together with the phenyl ring to which they are attached form a naphthalenyl group, or one of R$^2$ or R$^{20}$ is as defined above and the other one of R$^2$ or R$^{20}$ together with R$^9$ form a direct bond.

A sixth group of interesting compounds (herein referred to as group "G6") consists of those compounds of formula (I) or any subgroup thereof, wherein:

X is C(=O) or CHR$^8$, preferably CHR$^8$, and R$^8$ is hydrogen; —C(=O)—NR$^{17}$R$^{18}$; arylC$_{1-6}$alkyloxycarbonyl; C$_{1-6}$alkyl substituted with hydroxyl; piperazinylcarbonyl substituted with hydroxyl; hydroxyC$_{1-6}$alkyl; hydroxyC$_{1-6}$alkyloxyC$_{1-6}$alkyl; pyrrolidinyl substituted with hydroxyC$_{1-6}$alkyl; or piperidinylcarbonyl substituted with one or two substituents selected from hydroxy, C$_{1-6}$alkyl, hydroxyC$_{1-6}$alkyl, C$_{1-6}$alkyloxyC$_{1-6}$alkyl, C$_{1-6}$alkyl(dihydroxy)C$_{1-6}$alkyl or C$_{1-6}$alkyloxy(hydroxy)C$_{1-6}$alkyl;

R$^{17}$ and R$^{18}$ are each independently selected from hydrogen, C$_{1-6}$alkyl, di(C$_{1-6}$alkyl)aminoC$_{1-6}$alkyl, arylC$_{1-6}$alkyl, C$_{1-6}$alkyloxyC$_{1-6}$alkyl or hydroxyC$_{1-6}$alkyl;

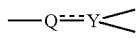

is —CR$^9$=C<, —CHR$^9$—CH< or —CHR$^9$—N<;

R$^1$ is hydrogen, heteroaryl, C$_{1-6}$alkyloxycarbonyl, C$_{1-12}$alkyl or C$_{1-12}$alkyl substituted with heteroaryl;

R$^3$ is hydrogen, C$_{1-6}$alkyl or heteroaryl;

R$^4$ and R$^5$ are each independently hydrogen, halo, C$_{1-6}$alkyl, hydroxyC$_{1-6}$alkyl, cyano, cyano-C$_{1-6}$alkyl, hydroxyl, C$_{2-6}$alkenyl or C$_{1-6}$alkyloxy; in particular hydrogen, halo, C$_{1-6}$alkyl, cyano, cyanoC$_{1-6}$alkyl, hydroxy or C$_{1-6}$alkyloxy;

when p is 1 then $R^7$ is aryl$C_{1-6}$alkyl or hydroxy;

Z is a radical selected from (a-1), (a-2), (a-3), (a-4), (a-5), (a-7), (a-8) and (a-9);

$R^{10}$ or $R^{11}$ are each independently selected from hydrogen; halo; hydroxyl; amino; $C_{1-6}$alkyl; nitro; polyhalo$C_{1-6}$alkyl; cyano; cyano$C_{1-6}$alkyl; tetrazolo$C_{1-6}$alkyl; aryl; heteroaryl; heteroaryl$C_{1-6}$alkyl; aryl(hydroxy)$C_{1-6}$alkyl; arylcarbonyl; $C_{1-6}$alkylcarbonyl; $C_{3-7}$cycloalkylcarbonyl; $C_{3-7}$cycloalkyl(hydroxy)$C_{1-6}$alkyl; aryl$C_{1-6}$alkyloxy$C_{1-6}$alkyl; $C_{1-6}$alkyloxy$C_{1-6}$alkyloxy$C_{1-6}$alkyl; $C_{1-6}$alkylcarbonyloxy$C_{1-6}$alkyl; $C_{1-6}$alkyloxycarbonyl$C_{1-6}$alkyloxy$C_{1-6}$alkyl; hydroxy$C_{1-6}$alkyloxy$C_{1-6}$alkyl; $C_{1-6}$alkyloxycarbonyl$C_{2-6}$alkenyl; $C_{1-6}$alkyloxy$C_{1-6}$alkyl; $C_{1-6}$alkyloxycarbonyl; aminocarbonyl; hydroxy$C_{1-6}$alkyl; amino$C_{1-6}$alkyl; hydroxycarbonyl; hydroxycarbonyl-$C_{1-6}$alkyl and —$(CH_2)_v$—$(C(=O))_r$—$(CHR^{19})_u$—$NR^{13}R^{14}$;

v is 0 or 1;

u is 0 or 1;

$R^{12}$ is hydrogen or $C_{1-6}$alkyl;

$R^{13}$ and $R^{14}$ are each independently selected from hydrogen; $C_{1-12}$alkyl; $C_{1-6}$alkylcarbonyl; $C_{1-6}$alkylsulfonyl; aryl$C_{1-6}$alkylcarbonyl; $C_{3-7}$cycloalkylcarbonyl; —$(CH_2)_k$—$NR^{15}R^{16}$; $C_{1-12}$alkyl substituted with a substituent selected from hydroxy, hydroxycarbonyl, cyano, $C_{1-6}$alkyloxycarbonyl or aryl; or $R^{13}$ and $R^{14}$ together with the nitrogen to which they are attached form morpholinyl, pyrrolidinyl, piperazinyl or piperazinyl substituted with a substituent selected from $C_{1-6}$alkyl or aryl$C_{1-6}$alkyloxycarbonyl;

k is 2;

$R^{15}$ and $R^{16}$ are each independently selected from hydrogen, $C_{1-12}$alkyl or aryl$C_{1-6}$alkyloxycarbonyl; in particular hydrogen, $C_{1-6}$alkyl or aryl$C_{1-6}$alkyloxycarbonyl; or $R^{15}$ and $R^{16}$ together with the nitrogen to which they are attached form morpholinyl; piperazinyl; or piperazinyl substituted with $C_{1-6}$alkyloxycarbonyl;

aryl is phenyl or phenyl substituted with halo; and heteroaryl is pyridinyl, indolyl, oxadiazolyl or tetrazolyl; and each pyridinyl, indolyl, oxadiazolyl or tetrazolyl can optionally be substituted with one substituent selected from $C_{1-6}$alkyl, aryl or aryl$C_{1-6}$alkyl.

A seventh group of more preferred compounds (herein referred to as group "G7") consists of those compounds of formula (I), wherein:

m is 0; n is 1 or 2, in particular 1; p is 0; s is 0; t is 0; X is $CH_2$;

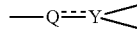

is —$CR^9$=C< and $R^9$ is hydrogen or $C_{1-6}$alkyl, preferably hydrogen or methyl, more preferably hydrogen, or $R^9$ together with one of $R^2$ or $R^{20}$ form a direct bond; $R^1$ is hydrogen; $R^3$ is hydrogen; and $R^6$ is hydrogen.

An eight group of more preferred compounds (herein referred to as group "G8") consists of those compounds of formula (I) or compounds of group "G7" as defined above, wherein:

$R^4$ and $R^5$ are each independently hydrogen, halo, $C_{1-6}$alkyl, hydroxy$C_{1-6}$alkyl, polyhalo-$C_{1-6}$alkyl, cyano, cyano$C_{1-6}$alkyl, hydroxy, amino, $C_{2-6}$alkenyl or $C_{1-6}$alkyloxy; in particular hydrogen, halo, $C_{1-6}$alkyl, polyhalo$C_{1-6}$alkyl, cyano, cyano$C_{1-6}$alkyl, hydroxy, amino or $C_{1-6}$alkyloxy;

more preferably $R^4$ and $R^5$ are each independently hydrogen, halo, $C_{1-6}$alkyl, hydroxyl-$C_{1-6}$alkylpolyhalo$C_{1-6}$alkyl, hydroxy, amino, $C_{2-6}$alkenyl or $C_{1-6}$alkyloxy; in particular hydrogen, halo, $C_{1-6}$alkyl, polyhalo$C_{1-6}$alkyl, hydroxy, amino, or $C_{1-6}$alkyloxy;

still more preferably $R^4$ and $R^5$ are each independently hydrogen, halo, $C_{1-6}$alkyl, hydroxyl-$C_{1-6}$alkyl, hydroxyl, $C_{2-6}$alkenyl or $C_{1-6}$alkyloxy; in particular hydrogen, halo, $C_{1-6}$alkyl, hydroxy or $C_{1-6}$alkyloxy;

most preferably $R^4$ and $R^5$ are each independently hydrogen, $C_{1-6}$alkyl, hydroxy$C_{1-6}$alkyl, $C_{2-6}$alkenyl or $C_{1-6}$alkyloxy (such as, e.g., $R^4$ and $R^5$ may each independently be hydrogen, methyl or methyloxy).

A ninth group of more preferred compounds (herein referred to as group "G9") consists of those compounds of formula (I) or compounds of any of groups "G7" or "G8" as defined above, wherein:

Z is a radical selected from (a-1), (a-2), (a-3), (a-4) and (a-5);

or preferably Z is a radical selected from (a-1), (a-2) and (a-4).

A tenth group of more preferred compounds (herein referred to as group "G10") consists of those compounds of formula (I) or compounds of any of groups "G7", "G8" or "G9" as defined above, wherein:

$R^{10}$ or $R^{11}$ are each independently selected from hydrogen, halo, hydroxy, amino, $C_{1-6}$alkyl, nitro, polyhalo$C_{1-6}$alkyl, cyano, cyano$C_{1-6}$alkyl, tetrazolo$C_{1-6}$alkyl, aryl, heteroaryl, heteroaryl$C_{1-6}$alkyl, aryl(hydroxy)$C_{1-6}$alkyl, arylcarbonyl, $C_{1-6}$alkylcarbonyl, $C_{3-7}$cycloalkylcarbonyl, $C_{3-7}$cycloalkyl(hydroxy)$C_{1-6}$alkyl, aryl$C_{1-6}$alkyloxy$C_{1-6}$alkyl, $C_{1-6}$alkyloxy$C_{1-6}$alkyloxy$C_{1-6}$alkyl, $C_{1-6}$alkylcarbonyloxy$C_{1-6}$alkyl, $C_{1-6}$alkyloxycarbonyl$C_{1-6}$alkyloxy$C_{1-6}$alkyl, hydroxy$C_{1-6}$alkyloxy$C_{1-6}$alkyl, $C_{1-6}$alkyloxycarbonyl$C_{2-6}$alkenyl, $C_{1-6}$alkyloxy$C_{1-6}$alkyl, $C_{1-6}$alkyloxycarbonyl, aminocarbonyl, hydroxy$C_{1-6}$alkyl, amino$C_{1-6}$alkyl, hydroxycarbonyl, hydroxycarbonyl-$C_{1-6}$alkyl and —$(CH_2)_v$—$(C(=O))_r$—$(CHR^{19})_u$—$NR^{13}R^{14}$;

v is 0 or 1;

r is 0 or 1;

u is 0 or 1;

$R^{13}$ and $R^{14}$ are each independently selected from hydrogen; $C_{1-12}$alkyl; $C_{1-6}$alkylcarbonyl; $C_{1-6}$alkylsulfony; aryl$C_{1-6}$alkylcarbonyl; $C_{3-7}$cycloalkylcarbonyl; —$(CH_2)_k$—$NR^{15}R^{16}$; $C_{1-12}$alkyl substituted with a substituent selected from hydroxy, hydroxycarbonyl, cyano, $C_{1-6}$alkyloxycarbonyl or aryl; or $R^{13}$ and $R^{14}$ together with the nitrogen to which they are attached form a morpholinyl, pyrrolidinyl, piperazinyl or piperazinyl substituted with a substituent selected from $C_{1-6}$alkyl or aryl$C_{1-6}$alkyloxycarbonyl;

k is 2;

$R^{15}$ and $R^{16}$ are each independently selected from hydrogen, $C_{1-12}$alkyl or aryl$C_{1-6}$alkyloxycarbonyl; in particular hydrogen, $C_{1-6}$alkyl or aryl-$C_{1-6}$alkyloxycarbonyl; or $R^{15}$ and $R^{16}$ together with the nitrogen to which they are attached form morpholinyl, piperazinyl, or piperazinyl substituted with $C_{1-6}$alkyloxycarbonyl; $R^{12}$ is hydrogen or $C_{1-6}$alkyl.

An eleventh group of more preferred compounds (herein referred to as group "G11") consists of those compounds of group "G10" as defined above, wherein:

$R^{10}$ or $R^{11}$ are each independently selected from hydrogen, hydroxy, amino, $C_{1-6}$alkyl, nitro, polyhalo$C_{1-6}$alkyl, cyano, aryl, aryl$C_{1-6}$alkyl, aryl(hydroxy)$C_{1-6}$alkyl, arylcarbonyl, $C_{1-6}$alkyloxy, $C_{1-6}$alkyloxy$C_{1-6}$alkyl, $C_{1-6}$alkyloxycarbonyl, aminocarbonyl, hydroxy$C_{1-6}$alkyl, amino$C_{1-6}$alkyl, hydroxycarbonyl and —(CH$_2$)$_v$—(C(=O))$_r$—(CH$_2$)$_u$—NR$^{13}$R$^{14}$;

v is 0 or 1;
r is 0 or 1;
u is 0;
R$^{13}$ and R$^{14}$ are each independently selected from hydrogen, $C_{1-6}$alkyl, —(CH$_2$)$_k$—NR$^{15}$R$^{16}$ and $C_{1-12}$alkyl substituted with hydroxy; or
R$^{13}$ and R$^{14}$ together with the nitrogen to which they are attached form pyrrolidinyl;
k is 2;
R$^{15}$ and R$^{16}$ are each independently $C_{1-6}$alkyl;
R$^{12}$ is hydrogen or $C_{1-6}$alkyl, preferably hydrogen.

A twelfth group of more preferred compounds (herein referred to as group "G12") consists of those compounds of group "G10" as defined above, wherein:
R$^{10}$ and R$^{11}$ are each independently selected from hydrogen, hydroxy and hydroxy$C_{1-6}$alkyl; and R$^{12}$ is hydrogen or $C_{1-6}$alkyl, preferably hydrogen (such as, e.g., R$^{10}$ and R$^{11}$ may each be independently selected from hydrogen, hydroxy and hydroxymethyl; and R$^{12}$ may be hydrogen or methyl, preferably hydrogen).

A thirteenth group of more preferred compounds (herein referred to as group "G13") consists of those compounds of formula (I) or compounds of any of groups "G7", "G8", "G9", "G10", "G11" or "G12" as defined above, wherein:
aryl is phenyl or phenyl substituted with halo; and
heteroaryl is pyridinyl, indolyl, oxadiazolyl or tetrazolyl; and each pyridinyl, indolyl, oxadiazolyl or tetrazolyl can optionally be substituted with one substituent selected from $C_{1-6}$alkyl, aryl and aryl$C_{1-6}$alkyl.

A fourteenth group of more preferred compounds (herein referred to as group "G14") consists of those compounds of group "G13" as defined above, wherein: aryl is phenyl or phenyl substituted with halo; and
heteroaryl is pyridinyl or indolyl.

A fifteenth group of particularly preferred compounds (herein referred to as group "G15") consists of those compounds of formula (I) or any subgroup thereof, wherein: m is 0; n is 1 or 2, in particular 1; p is 0; s is 0; t is 0; X is CH$_2$;

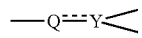

is —CR$^9$=C< and R$^9$ is hydrogen or $C_{1-6}$alkyl, more preferably hydrogen, or R$^9$ together with one of R$^2$ or R$^{20}$ form a direct bond; R$^1$ is hydrogen; R$^3$ is hydrogen; R$^4$ and R$^5$ are each independently hydrogen, $C_{1-6}$alkyl, hydroxy$C_{1-6}$alkyl, $C_{2-6}$alkenyl or $C_{1-6}$alkyloxy; in particular hydrogen, $C_{1-6}$alkyl or $C_{1-6}$alkyloxy; R$^8$ is hydrogen; Z is a radical selected from (a-1), (a-2) and (a-4); and R$^{10}$ or R$^{11}$ are each independently hydrogen, hydroxy or hydroxy$C_{1-6}$alkyl.

A sixteenth group of particularly preferred compounds (herein referred to as group "G16") consists of those compounds of formula (I) or any subgroup thereof, wherein:
m is 0; n is 1 or 2, in particular 1; p is 0; s is 0; t is 0; X is CH$_2$;

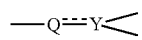

is —CR$^9$=C< and R$^9$ is hydrogen or methyl, or R$^9$ together with one of R$^2$ or R$^{20}$ form a direct bond; R$^1$ is hydrogen; R$^3$ is hydrogen; R$^4$ and R$^5$ are each independently hydrogen, methyl or methyloxy; R$^6$ is hydrogen; Z is a radical selected from (a-1), (a-2) and (a-4); and R$^{10}$ or R$^{11}$ are each independently hydrogen, hydroxy or hydroxymethyl.

A seventeenth group of particularly preferred compounds (herein referred to as group "G17") consists of those compounds of formula (I) or, whenever possible any subgroup thereof as defined hereinabove, wherein:

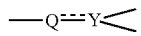

is —CR$^9$=C< and then the dotted line is a bond, —C(=O)—CH<, —CHR$^9$—CH<, or —CHR$^9$—N<, wherein each R$^9$ is independently hydrogen or $C_{1-6}$alkyl, or wherein R$^9$ together with one of R$^2$ or R$^{20}$ form a direct bond; in particular

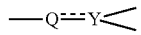

is —CR$^9$=C< and then the dotted line is a bond, —CHR$^9$—CH<, or —CHR$^9$—N<, wherein each R$^9$ is independently hydrogen or $C_{1-6}$alkyl, or wherein R$^9$ together with one of R$^2$ or R$^{20}$ form a direct bond; more in particular

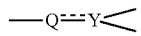

is —CR$^9$=C< and then the dotted line is a bond, wherein each R$^9$ is independently hydrogen or $C_{1-6}$alkyl, or wherein R$^9$ together with one of R$^2$ or R$^{20}$ form a direct bond.

Preferably, in compounds of formula (I), and in particular in compounds of any one of the above groups "G1" to "G17", the substituents on the central phenyl ring other than R$^2$ and R$^{20}$ may be in the para (p-) position.

In an embodiment, when m is 1, when the substituents on the phenyl ring other than R$^2$ and R$^{20}$ are in the meta position, when s is 0 and t is 0; then Z may be a radical selected from (a-1), (a-3), (a-4), (a-5), (a-6), (a-7) or (a-8).

In a preferred embodiment, in compounds of formula (I), and in particular in compounds of any one of the above groups "G1" to "G17" (the recitation "any one of the groups 'G1' to 'G17'" as used throughout this specification encompasses a specific reference to any one or each of the compound groups "G1", "G2", "G3", "G4", "G5", "G6", "G7", "G8", "G9", "G10", "G11", "G12", "G13", "G14", "G15", "G16" or "G17" as defined herein), R$^2$ and R$^{20}$ are each independently selected from halo, cyano, amino, mono- or di($C_{1-6}$alkyl)amino, $C_{1-6}$alkyl, aryl, heteroaryl, aryl$C_{1-6}$alkyl, heteroaryl$C_{1-6}$alkyl, hydroxy$C_{1-6}$alkyl, polyhalo-$C_{1-6}$alkyl preferably perhalo$C_{1-6}$alkyl, $C_{1-6}$alkyloxy, polyhalo$C_{1-6}$alkyloxy preferably perhalo$C_{1-6}$alkyloxy, aryl$C_{1-6}$alkyloxy, heteroaryl$C_{1-6}$alkyloxy, $C_{1-6}$alkylthio, arylthio preferably phenylthio, $C_{1-6}$alkylcarbonyl, hydroxy$C_{1-6}$alkylcarbonyl, $C_{1-6}$alkyloxycarbonyl, $C_{1-6}$alkylcarbonyloxy, $C_{1-6}$alkylcarbonylamino, morpholinyl, piperidinyl, pyrrolidinyl and piperazinyl; or R$^2$ and R$^{20}$ together with the central phenyl ring form a naphthalenyl.

In another preferred embodiment, in compounds of formula (I), and in particular in compounds of any one of the above groups "G1" to "G17", R$^2$ and R$^{20}$ are each independently selected from $C_{1-6}$alkyl, aryl, heteroaryl, aryl$C_{1-6}$alkyl, heteroaryl$C_{1-6}$alkyl, hydroxy$C_{1-6}$alkyl, polyhalo$C_{1-6}$alkyl, polyhalo$C_{1-6}$alkyloxy, $C_{1-6}$alkyloxy, aryl$C_{1-6}$alkyloxy, heteroaryl$C_{1-6}$alkyloxy, $C_{1-6}$alkylthio, arylthio preferably phenylthio, $C_{1-6}$alkylcarbonyl, hydroxy$C_{1-6}$alkylcarbonyl, $C_{1-6}$alkyloxycarbonyl, $C_{1-6}$alkylcarbonyloxy, $C_{1-6}$alkylcarbonylamino morpholinyl, piperidinyl, pyrrolidinyl and piperazinyl, any of said groups being optionally and independently substituted with one or more, preferably one or two, substituents selected from halo, hydroxy, cyano, amino, mono- or di($C_{1-6}$alkyl)amino, $C_{1-6}$alkyl, polyhalo$C_{1-6}$alkyl, aryl, heteroaryl and $C_{1-6}$alkyloxy; or $R^2$ and $R^{20}$ together with the central phenyl ring form a naphthalenyl.

In a particularly preferred embodiment, in compounds of formula (I), and in particular in compounds of any one of the above groups "G1" to "G17", $R^2$ and $R^{20}$ are each independently selected from halo, cyano, $C_{1-6}$alkyl, hydroxy$C_{1-6}$alkyl, polyhalo$C_{1-6}$alkyl preferably perhalo-$C_{1-6}$alkyl, $C_{1-6}$alkyloxy, $C_{1-6}$alkylcarbonylamino and morpholinyl; or $R^2$ and $R^{20}$ together with the central phenyl ring form a naphthalenyl.

In another preferred embodiment, in compounds of formula (I), and in particular in compounds of any one of the above groups "G1" to "G17", $R^2$ and $R^{20}$ are each independently selected from halo, $C_{1-6}$alkyl, polyhalo$C_{1-6}$alkyl preferably perhalo$C_{1-6}$alkyl, and $C_{1-6}$alkyloxy, or $R^2$ and $R^{20}$ together with the central phenyl ring form a naphthalenyl.

In another preferred embodiment, in compounds of formula (I), and in particular in compounds of any one of the above groups "G1" to "G17", $R^2$ and $R^{20}$ are each independently selected from halo, $C_{1-6}$alkyl, and $C_{1-6}$alkyloxy.

In another preferred embodiment, in compounds of formula (I), and in particular in compounds of any one of the above groups "G1" to "G17", $R^2$ and $R^{20}$ are each independently selected from halo, $C_{1-6}$alkyl, $C_{1-6}$alkyloxy, hydroxy$C_{1-6}$alkyl, or $R^2$ and $R^{20}$ together with the central phenyl ring form a naphthalenyl.

In another particularly preferred embodiment, in compounds of formula (I), and in particular in compounds of any one of the above groups "G1" to "G17", $R^2$ and $R^{20}$ are each independently selected from fluoro, chloro, bromo, cyano, methyl, hydroxymethyl, trihalomethyl preferably trifluoromethyl, methyloxy, methylcarbonylamino and morpholinyl, or $R^2$ and $R^{20}$ together with the central phenyl ring form a naphthalenyl.

In a further preferred embodiment, in compounds of formula (I), and in particular in compounds of any one of the above groups "G1" to "G17", $R^2$ and $R^{20}$ are each independently selected from fluoro, chloro, methyl, trifluoromethyl and methyloxy, or $R^2$ and $R^{20}$ together with the central phenyl ring form a naphthalenyl.

In a further preferred embodiment, in compounds of formula (I), and in particular in compounds of any one of the above groups "G1" to "G17", $R^2$ and $R^{20}$ are each independently selected from fluoro, chloro, methyl and methyloxy.

In another preferred embodiment, in compounds of formula (I), and in particular in compounds of any one of the above groups "G1" to "G17", $R^2$ and $R^{20}$ are each independently selected from fluoro, chloro, bromo, methyl, methyloxy, hydroxymethyl, or $R^2$ and $R^{20}$ together with the central phenyl ring form a naphthalenyl.

In another preferred embodiment, in compounds of formula (I), and in particular in compounds of any one of the above groups "G1" to "G17", $R^2$ and $R^{20}$ are each independently selected from halo, cyano, polyhalo$C_{1-6}$alkyl, $C_{1-6}$alkyl, morpholinyl, $C_{1-6}$alkyloxy, hydroxyl-$C_{1-6}$alkyl, —NR$^{21}$R$^{22}$ wherein $R^{21}$ is hydrogen and $R^{22}$ is $C_{1-6}$alkylcarbonyl; or $R^2$ and $R^{20}$ together with the phenyl ring to which they are attached form a naphthalenyl group, or one of $R^2$ or $R^{20}$ is as defined above and the other one of $R^2$ or $R^{20}$ together with $R^9$ form a direct bond; in particular $R^2$ and $R^{20}$ are each independently selected from chloro, fluoro, bromo, cyano, trifluoromethyl, methyl, morpholinyl, methyloxy, hydroxymethyl, —NH—C(=O)—CH$_3$; or $R^2$ and $R^{20}$ together with the phenyl ring to which they are attached form a naphthalenyl group, or one of $R^2$ or $R^{20}$ is as defined above and the other one of $R^2$ or $R^{20}$ together with $R^9$ form a direct bond.

Several preferred albeit non-limiting embodiments of compounds of formula (I), in particular of compounds of any one of the above groups "G1" to "G17", include compounds wherein $R^2$ and $R^{20}$ substituent combinations are as shown in Table 1:

TABLE 1

| Combination | $R^2$ | $R^{20}$ |
|---|---|---|
| 1 | $C_{1-6}$alkyl | $C_{1-6}$alkyl |
| 2 | methyl | methyl |
| 3 | perhalo$C_{1-6}$alkyl | perhalo$C_{1-6}$alkyl |
| 4 | trifluoromethyl | trifluoromethyl |
| 5 | halo | $C_{1-6}$alkyl |
| 6 | chloro | methyl |
| 7 | halo | halo |
| 8 | fluoro | fluoro |
| 9 | chloro | chloro |
| 10 | halo | $C_{1-6}$alkyloxy |
| 11 | fluoro | methyloxy |
| 12 | halo | $C_{1-6}$alkylcarbonylamino |
| 13 | fluoro | acetylamino |
| 14 | halo | hydroxy$C_{1-6}$alkyl |
| 15 | bromo | hydroxymethyl |
| 16 | cyano | morpholinyl |
| 17 | $R^2$ and $R^{20}$ together with the central phenyl ring form a naphthalenyl | |

In an embodiment, particularly interesting $R^2$, $R^{20}$ combinations include combinations #1, 2, 3, 4, 5, 6, 7, 8, 9, 10, 11 and 17 as defined in Table 1, more particularly combinations #2, 4, 6, 8, 9, 11 and 17 as defined in Table 1.

In another embodiment, particularly interesting $R^2$, $R^{20}$ combinations include combinations #5, 6, 7, 8, 9, 10 and 11 as defined in Table 1, more particularly combinations #10 and 11 as defined in Table 1.

In a further embodiment, particularly interesting $R^2$, $R^{20}$ combinations include combinations #1, 2, 5, 6, 7, 8, 9, 10, 11, 14, 15 and 17 as defined in Table 1, more particularly combinations #10 and 11 as defined in Table 1.

Thus, exemplary preferred groups of compounds consists of those compounds of formula (I) or any subgroup thereof, wherein:

m is 0; n is 1 or 2; p is 0; s is 0; t is 0; X is CH$_2$;

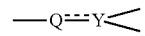

is —CR$^9$=C< and $R^9$ is hydrogen or $C_{1-6}$alkyl, more preferably hydrogen; $R^1$ is hydrogen; $R^3$ is hydrogen; $R^4$ and $R^5$ are each independently hydrogen, $C_{1-6}$alkyl, hydroxy $C_{1-6}$alkyl, $C_{2-6}$alkenyl or $C_{1-6}$alkyloxy; $R^6$ is hydrogen; Z is a radical selected from (a-1), (a-2) and (a-4); $R^{10}$ or $R^{11}$ are each independently hydrogen, hydroxy or hydroxy$C_{1-6}$alkyl; $R^{12}$ is hydrogen or $C_{1-6}$alkyl, preferably hydrogen; and $R^2$ and $R^{20}$ are each independently selected from halo, cyano, $C_{1-6}$alkyl, hydroxy$C_{1-6}$alkyl, polyhalo$C_{1-6}$alkyl preferably perhaloC$_{1-6}$alkyl, C$_{1-6}$alkyloxy, C$_{1-6}$alkylcarbonylamino and morpholinyl, or R$^2$ and R$^{20}$ together with the central phenyl ring form a naphthalenyl; or one of R$^2$ or R$^{20}$ is as defined above and the other one of R$^2$ or R$^{20}$ together with R$^9$ form a direct bond;

more preferably R$^2$ and R$^{20}$ are each independently selected from halo, C$_{1-6}$alkyl, polyhalo-C$_{1-6}$alkyl preferably perhaloC$_{1-6}$alkyl and C$_{1-6}$alkyloxy, or R$^2$ and R$^{20}$ together with the central phenyl ring form a naphthalenyl;

also more preferably R$^2$ and R$^{20}$ can be each independently selected from halo, C$_{1-6}$alkyl, and C$_{1-6}$alkyloxy;

as well more preferably R$^2$ and R$^{20}$ can be each independently selected from halo, C$_{1-6}$alkyl, C$_{1-6}$alkyloxy, hydroxyC$_{1-6}$alkyl, or R$^2$ and R$^{20}$ together with the central phenyl ring to form a naphthalenyl;

even more preferably R$^2$ and R$^{20}$ are each independently selected from fluoro, chloro, bromo, cyano, methyl, hydroxymethyl, trihalomethyl preferably trifluoromethyl, methyloxy, methylcarbonylamino and morpholinyl; or R$^2$ and R$^{20}$ together with the central phenyl ring form a naphthalenyl; or one of R$^2$ or R$^{20}$ is as defined above and the other one of R$^2$ or R$^{20}$ together with R$^9$ form a direct bond;

still more preferably R$^2$ and R$^{20}$ are each independently selected from fluoro, chloro, methyl, trifluoromethyl and methyloxy, or R$^2$ and R$^{20}$ together with the central phenyl ring form a naphthalenyl;

also more preferably R$^2$ and R$^{20}$ are each independently selected from fluoro, chloro, methyl and methyloxy;

as well more preferably R$^2$ and R$^{20}$ are each independently selected from fluoro, chloro, bromo, methyl, methyloxy, hydroxymethyl, or R$^2$ and R$^{20}$ together with the central phenyl ring form a naphthalenyl;

and also particularly preferably R$^2$ and R$^{20}$ may be as shown in Table 1.

Another embodiment consists of compounds of formula (I)

hydroxy, amino, aryl and heteroaryl, piperazinylcarbonyl substituted with a substituent selected from hydroxy, hydroxyC$_{1-6}$alkyl and hydroxyC$_{1-6}$alkyloxyC$_{1-6}$alkyl, pyrrolidinyl substituted with hydroxyC$_{1-6}$alkyl, and piperidinylcarbonyl substituted with one or two substituents selected from hydroxy, C$_{1-6}$alkyl, hydroxyC$_{1-6}$alkyl, C$_{1-6}$alkyloxyC$_{1-6}$alkyl, C$_{1-6}$alkyl(dihydroxy)C$_{1-6}$alkyl and C$_{1-6}$alkyloxy(hydroxy)C$_{1-6}$alkyl;

R$^{17}$ and R$^{18}$ are each independently selected from hydrogen, C$_{1-6}$alkyl, di(C$_{1-6}$alkyl)aminoC$_{1-6}$alkyl, arylC$_{1-6}$alkyl, C$_{1-6}$alkyloxyC$_{1-6}$alkyl, hydroxyC$_{1-6}$alkyl, hydroxyC$_{1-6}$alkyl(C$_{1-6}$alkyl), or hydroxyC$_{1-6}$alkyl(arylC$_{1-6}$alkyl);

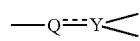

is —CR$^9$=C<, and then the dotted line is a bond, —C(=O)—CH<, —C(=O)—N<, —CHR$^9$—CH<, or —CHR$^9$—N<, wherein each R$^9$ is independently hydrogen or C$_{1-6}$alkyl, or wherein R$^9$ together with one of R$^2$ or R$^{20}$ form a direct bond;

R$^1$ is hydrogen, aryl, heteroaryl, C$_{1-6}$alkyloxycarbonyl, C$_{1-12}$alkyl, or C$_{1-12}$alkyl substituted with one or two substituents independently selected from hydroxy, aryl, heteroaryl, amino, C$_{1-6}$alkyloxy, mono- or di(C$_{1-6}$alkyl)amino, morpholinyl, piperidinyl, pyrrolidinyl, piperazinyl, C$_{1-6}$alkylpiperazinyl, arylC$_{1-6}$alkylpiperazinyl, heteroarylC$_{1-6}$alkylpiperazinyl, C$_{3-7}$cycloalkyl-piperazinyl and C$_{3-7}$cycloalkylC$_{1-6}$alkylpiperazinyl;

R$^2$ and R$^{20}$ are each independently selected from
halo, hydroxy, cyano, nitro, carboxyl;
polyhaloC$_{1-6}$alkyl, perhaloC$_{1-6}$alkyl, polyhaloC$_{1-6}$alkyloxy, perhaloC$_{1-6}$alkyloxy; C$_{1-6}$alkyl, C$_{3-7}$cycloalkyl,

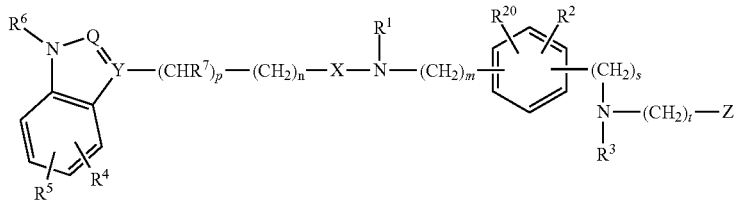

an N-oxide form, an addition salt, a solvate, or a stereochemically isomeric form thereof, wherein m is 0, 1 or 2 and when m is 0 then a direct bond is intended;

n is 0, 1, 2 or 3 and when n is 0 then a direct bond is intended;

p is 0 or 1 and when p is 0 then a direct bond is intended;
s is 0 or 1 and when s is 0 then a direct bond is intended;
t is 0 or 1 and when t is 0 then a direct bond is intended;
X is C(=O) or CHR$^8$, wherein
R$^8$ is selected from hydrogen, C$_{1-6}$alkyl, C$_{3-7}$cycloalkyl, —C(=O)—NR$^{17}$R$^{18}$, carboxyl, arylC$_{1-6}$alkyloxycarbonyl, heteroaryl, heteroarylcarbonyl, heteroarylC$_{1-6}$alkyloxycarbonyl, piperazinylcarbonyl, pyrrolidinyl, piperidinylcarbonyl, C$_{1-6}$alkyloxycarbonyl, C$_{1-6}$alkyl substituted with a substituent selected from hydroxy, amino, aryl and heteroaryl, C$_{3-7}$cycloalkyl substituted with a substituent selected from C$_{2-6}$alkenyl, aryl, heteroaryl, arylC$_{1-6}$alkyl, heteroarylC$_{1-6}$alkyl, C$_{3-7}$cycloalkylC$_{1-6}$alkyl, morpholinyl, piperidinyl, pyrrolidinyl, piperazinyl, C$_{1-6}$alkyloxy, aryloxy, heteroaryloxy, C$_{1-6}$alkylthio, arylthio, heteroarylthio, C$_{1-6}$alkylcarbonyl, C$_{3-7}$cycloalkylcarbonyl, arylcarbonyl, heteroarylcarbonyl, C$_{1-6}$alkyloxycarbonyl, C$_{3-7}$cycloalkyloxycarbonyl, aryloxycarbonyl, heteroaryloxycarbonyl, C$_{1-6}$alkylcarbonyloxy, C$_{3-7}$cycloalkylcarbonyloxy, arylcarbonyloxy or heteroarylcarbonyloxy, any of said groups being optionally independently substituted with one or more, preferably one or two, substituents selected from halo, hydroxy, cyano, nitro, carboxyl, amino, mono- or di(C$_{1-6}$alkyl)amino, C$_{1-6}$alkyl, polyhaloC$_{1-6}$alkyl, aryl, heteroaryl, C$_{1-6}$alkyloxy, C$_{1-6}$alkylcarbonyl, C$_{1-6}$alkyloxycarbonyl and C$_{1-6}$alkylcarbonyloxy; and
—(CH$_2$)$_w$—(C(=O))$_y$NR$^{21}$R$^{22}$ wherein
w is 0, 1, 2, 3, 4, 5 or 6 and when w is 0 then a direct bond is intended;

y is 0 or 1 and when y is 0 then a direct bond is intended;

$R^{21}$ and $R^{22}$ are each independently selected from hydrogen, $C_{1-6}$alkyl, $C_{3-7}$cycloalkyl, $C_{1-6}$alkylcarbonyl and aryl$C_{1-6}$alkylcarbonyl, any of said groups being optionally independently substituted with one or more, preferably one or two, substituents selected from halo, hydroxy, amino, mono- or di($C_{1-6}$alkyl)amino, $C_{1-6}$alkyl, polyhalo$C_{1-6}$alkyl, $C_{1-6}$alkyloxy, aryl and heteroaryl, or $R^{21}$ and $R^{22}$ together with the nitrogen to which they are attached form morpholinyl, piperidinyl, pyrrolidinyl or piperazinyl, any of said groups being optionally independently substituted with one or more, preferably one or two, substituents selected from $C_{1-6}$alkyl, polyhalo$C_{1-6}$alkyl, $C_{1-6}$alkyloxy, $C_{3-7}$cycloalkyl, $C_{3-7}$cycloalkyl$C_{1-6}$alkyl, aryl$C_{1-6}$alkyl and heteroaryl$C_{1-6}$alkyl;

or $R^2$ and $R^{20}$ together with the phenyl ring to which they are attached form a naphthalenyl group, optionally substituted with one or more, preferably one or two, substituents selected from halo, hydroxy, amino, mono- or di($C_{1-6}$alkyl)amino, $C_{1-6}$alkyl, polyhalo-$C_{1-6}$alkyl, $C_{1-6}$alkyloxy, aryl and heteroaryl;

or $R^2$ and $R^{20}$ together form a bivalent radical of the formula —(CH$_2$)$_b$— wherein b is 3, 4 or 5, optionally substituted with one or more, preferably one or two, substituents selected from halo, hydroxy, amino, mono- or di($C_{1-6}$alkyl)amino, $C_{1-6}$alkyl, polyhalo$C_{1-6}$alkyl, $C_{1-6}$alkyloxy, aryl and heteroaryl;

or one of $R^2$ or $R^{20}$ is as defined above and the other one of $R^2$ or $R^{20}$ together with $R^9$ form a direct bond;

$R^3$ is hydrogen, $C_{1-6}$alkyl, heteroaryl, $C_{3-7}$cycloalkyl, $C_{1-6}$alkyl substituted with a substituent selected from hydroxy, amino, aryl and heteroaryl, or $C_{3-7}$cycloalkyl substituted with a substituent selected from hydroxy, amino, aryl and heteroaryl;

$R^4$ and $R^5$ are each independently hydrogen, halo, $C_{1-6}$alkyl, polyhalo$C_{1-6}$alkyl, cyano, cyano$C_{1-6}$alkyl, hydroxy, amino, or $C_{1-6}$alkyloxy, or $R^4$ and $R^5$ together form a bivalent radical selected from methylenedioxy or ethylenedioxy;

$R^5$ is hydrogen, $C_{1-6}$alkyloxycarbonyl, or $C_{1-6}$alkyl;

when p is 1 then $R^7$ is hydrogen, aryl$C_{1-6}$alkyl, hydroxy, or heteroaryl$C_{1-6}$alkyl;

Z is a radical selected from

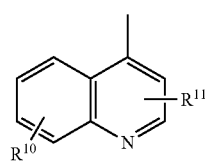

(a-1)

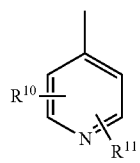

(a-2)

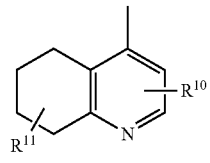

(a-3)

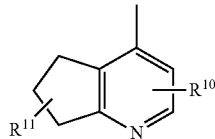

(a-4)

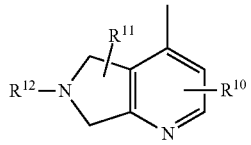

(a-5)

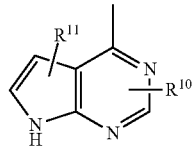

(a-6)

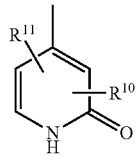

(a-7)

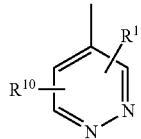

(a-8)

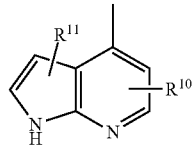

(a-9)

wherein $R^{10}$ or $R^{11}$ are each independently selected from hydrogen, halo, hydroxy, amino, $C_{1-6}$alkyl, nitro, polyhalo$C_{1-6}$alkyl, cyano, cyano$C_{1-6}$alkyl, tetrazolo$C_{1-6}$alkyl, aryl, heteroaryl, aryl$C_{1-6}$alkyl, heteroaryl$C_{1-6}$alkyl, aryl(hydroxy)$C_{1-6}$alkyl, heteroaryl(hydroxy)$C_{1-6}$alkyl, arylcarbonyl, heteroarylcarbonyl, $C_{1-6}$alkylcarbonyl, aryl$C_{1-6}$alkylcarbonyl, heteroaryl$C_{1-6}$alkylcarbonyl, $C_{1-6}$alkyloxy, $C_{3-7}$cycloalkylcarbonyl, $C_{3-7}$cycloalkyl(hydroxy)$C_{1-6}$alkyl, aryl$C_{1-6}$alkyloxy$C_{1-6}$alkyl, $C_{1-6}$alkyloxy$C_{1-6}$alkyloxy$C_{1-6}$alkyl, $C_{1-6}$alkylcarbonyloxy$C_{1-6}$alkyl, $C_{1-6}$alkyloxycarbonyl$C_{1-6}$alkyloxy$C_{1-6}$alkyl, hydroxy$C_{1-6}$alkyloxy$C_{1-6}$alkyl, $C_{1-6}$alkyloxycarbonyl$C_{2-6}$alkenyl, $C_{1-6}$alkyloxy$C_{1-6}$alkyl, $C_{1-6}$alkyloxycarbonyl, $C_{1-6}$alkylcarbonyloxy, aminocarbonyl, hydroxy$C_{1-6}$alkyl, amino$C_{1-6}$alkyl, hydroxycarbonyl, hydroxycarbonyl$C_{1-6}$alkyl and —(CH$_2$)$_v$—(C(=O))$_r$—(CHR$^{19}$)$_u$—NR$^{13}$R$^{14}$, wherein v is 0, 1, 2, 3, 4, 5, or 6 and when v is 0 then a direct bond is intended;

r is 0 or 1 and when r is 0 then a direct bond is intended;

u is 0, 1, 2, 3, 4, 5, or 6 and when u is 0 then a direct bond is intended;

$R^{19}$ is hydrogen or $C_{1-6}$alkyl;

$R^{13}$ and $R^{14}$ are each independently selected from hydrogen, $C_{1-12}$alkyl, $C_{1-6}$alkylcarbonyl, $C_{1-6}$alkylsulfonyl, arylC$_{1-6}$alkylcarbonyl, C$_{3-7}$cycloalkyl, C$_{3-7}$cycloalkylcarbonyl, —(CH$_2$)$_k$—NR$^{15}$R$^{16}$, C$_{1-12}$alkyl substituted with a substituent selected from hydroxy, hydroxycarbonyl, cyano, C$_{1-6}$alkyloxycarbonyl, C$_{1-6}$alkyloxy, aryl or heteroaryl, or C$_{3-7}$cycloalkyl substituted with a substituent selected from hydroxy, C$_{1-6}$alkyloxy, aryl, amino, arylC$_{1-6}$alkyl, heteroaryl or heteroarylC$_{1-6}$alkyl, or R$^{13}$ and R$^{14}$ together with the nitrogen to which they are attached form morpholinyl, piperidinyl, pyrrolidinyl, piperazinyl, or piperazinyl substituted with a substituent selected from C$_{1-6}$alkyl, arylC$_{1-6}$alkyl, arylC$_{1-6}$alkyloxycarbonyl, heteroarylC$_{1-6}$alkyl, C$_{3-7}$cycloalkyl and C$_{3-7}$cycloalkylC$_{1-6}$alkyl; wherein k is 0, 1, 2, 3, 4, 5, or 6 and when k is 0 then a direct bond is intended;

R$^{15}$ and R$^{16}$ are each independently selected from hydrogen, C$_{1-6}$alkyl, arylC$_{1-6}$alkyloxycarbonyl, C$_{3-7}$cycloalkyl, C$_{1-12}$alkyl substituted with a substituent selected from hydroxy, C$_{1-6}$alkyloxy, aryl, and heteroaryl, and C$_{3-7}$cycloalkyl substituted with a substituent selected from hydroxy, C$_{1-6}$alkyloxy, aryl, arylC$_{1-6}$alkyl, heteroaryl, and heteroarylC$_{1-6}$alkyl, or R$^{15}$ and R$^{16}$ together with the nitrogen to which they are attached form morpholinyl, piperazinyl, or piperazinyl substituted with C$_{1-6}$alkyloxycarbonyl;

R$^{12}$ is hydrogen, C$_{1-6}$alkyl, C$_{3-7}$cycloalkyl, C$_{1-6}$alkyl substituted with a substituent selected from hydroxy, amino, C$_{1-6}$alkyloxy and aryl, or C$_{3-7}$cycloalkyl substituted with a substituent selected from hydroxy, amino, aryl and C$_{1-6}$alkyloxy;

aryl is phenyl or naphthalenyl;

each phenyl or naphthalenyl can optionally be substituted with one, two or three substituents each independently selected from halo, hydroxy, C$_{1-6}$alkyl, amino, polyhaloC$_{1-6}$alkyl and C$_{1-6}$alkyloxy; and each phenyl or naphthalenyl can optionally be substituted with a bivalent radical selected from methylenedioxy and ethylenedioxy;

heteroaryl is pyridinyl, indolyl, quinolinyl, imidazolyl, furanyl, thienyl, oxadiazolyl, tetrazolyl, benzofuranyl or tetrahydrofuranyl;

each pyridinyl, indolyl, quinolinyl, imidazolyl, furanyl, thienyl, oxadiazolyl, tetrazolyl, benzofuranyl, or tetrahydrofuranyl can optionally be substituted with one, two or three substituents each independently selected from halo, hydroxy, C$_{1-6}$alkyl, amino, polyhaloC$_{1-6}$alkyl, aryl, arylC$_{1-6}$alkyl or C$_{1-6}$alkyloxy; and each pyridinyl, indolyl, quinolinyl, imidazolyl, furanyl, thienyl, benzofuranyl, or tetrahydrofuranyl can optionally be substituted with a bivalent radical selected from methylenedioxy or ethylenedioxy.

Another embodiment of particularly preferred compounds consists of those compounds of formula (I) wherein s is 0; t is 0; m is 0; p is 0; n is 1 or 2; R$^1$ is hydrogen; R$^2$ and R$^{20}$ are each independently selected from halo, cyano, polyhaloC$_{1-6}$alkyl, C$_{1-6}$alkyl, morpholinyl, C$_{1-6}$alkyloxy, hydroxyC$_{1-6}$alkyl, —NR$^{21}$R$^{22}$ wherein R$^{21}$ is hydrogen and R$^{22}$ is C$_{1-6}$alkylcarbonyl; or R$^2$ and R$^{20}$ together with the phenyl ring to which they are attached form a naphthalenyl group, or one of R$^2$ or R$^{20}$ is as defined above and the other one of R$^2$ or R$^{20}$ together with R$^9$ form a direct bond; R$^3$ is hydrogen; R$^4$ and R$^5$ are each independently hydrogen, C$_{1-6}$alkyl, C$_{1-6}$alkyloxy, hydroxyC$_{1-6}$alkyl, C$_{2-6}$alkenyl; R$^6$ is hydrogen;

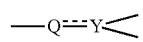

is —CR$^9$═C< and then the dotted line is a bond; R$^9$ is hydrogen or C$_{1-6}$alkyl; X is CH$_2$; Z is a radical selected from (a-1), (a-2) or (a-4); R$^{10}$ and R$^{11}$ are each independently selected from hydrogen, hydroxy and hydroxyC$_{1-6}$alkyl.

It shall be appreciated that when in compounds of formula (I), and in particular in compounds of any one of the above groups "G1" to "G17", R$^2$ and R$^{20}$ together with the phenyl ring to which they are attached form a naphthalenyl group, optionally substituted as defined above, then the substituents

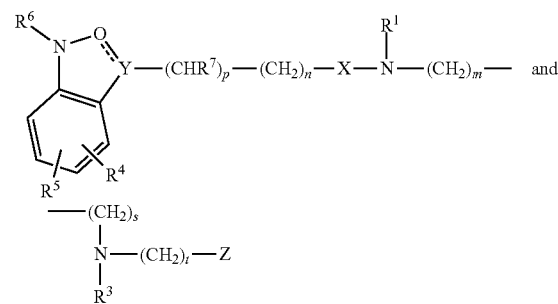

may be bound to either the same ring or to different rings of said naphthalenyl group.

In a preferred embodiment, R$^2$ and R$^{20}$ together with the phenyl ring to which they are attached may form a naphthalenyl group, as may be depicted by formulas (II-a) and (II-b), more preferably formula (II-a):

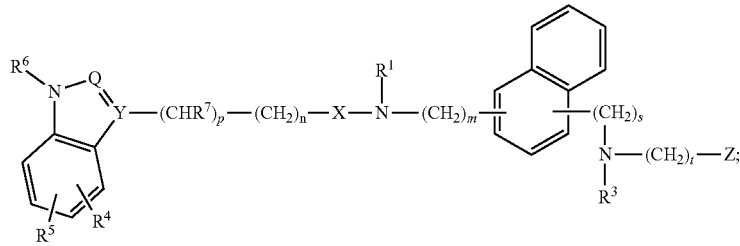

(II-a)

-continued

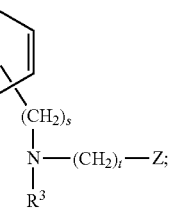

(II-b)

wherein substituents have meanings as defined above.

In another embodiment, in compounds of formula (I), and in particular in compounds of any one of the above groups "G1" to "G17", one of $R^2$ or $R^{20}$ is as defined herein before and the other one of $R^2$ or $R^{20}$ together with $R^9$ form a direct bond. By means of example, compound of formula (I) wherein

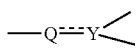

is —CR$^9$=C< and wherein $R^{20}$ together with $R^9$ form a direct bond may be depicted by the general formula (III):

(III)

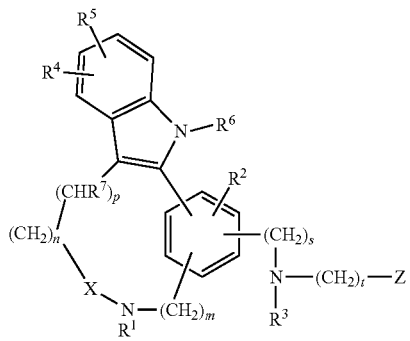

wherein substituents have meanings as defined above.

Preferably, where one of $R^2$ or $R^{20}$ together with $R^9$ form a direct bond, said direct bond may connect to a carbon of the central phenyl ring adjacent (i.e., o-position) to the carbon of the central phenyl ring to which the —(CH$_2$)$_m$— group is bound.

As can be appreciated, in compounds of formula (I), and in particular in compounds of any one of the above groups "G1" to "G17", the substituents $R^2$ and $R^{20}$ may be in ortho (o-), meta (m-) or para (p-) positions relative to one another on the central phenyl ring.

When $R^2$ and $R^{20}$ together form a bivalent radical of the formula —(CH$_2$)$_b$— wherein b is 3, 4 or 5, optionally substituted as above, then bonds of said bivalent radical are preferably attached in ortho (o-) positions relative to one another on the central phenyl ring.

As can be appreciated, in compounds of formula (I), and in particular in compounds of any one of the above groups "G1" to "G17", the four substituents on the central phenyl ring may be in various positions relative to one another. For example and without limitation, in compounds where substituents on the central phenyl ring other than $R^2$ and $R^{20}$ are in the para position, i.e., 1-, 4-, the $R^2$ and $R^{20}$ substituents may be in positions 2- and 3-, or in positions 2- and 5-, or in positions 2- and 6-, etc.

Table 2 lists preferred albeit non-limiting examples of compounds of formula (I) that were prepared in the present invention. The following abbreviations were used in the table: .HCl stands for hydrochloric acid salt, mp. stands for melting point.

TABLE 2

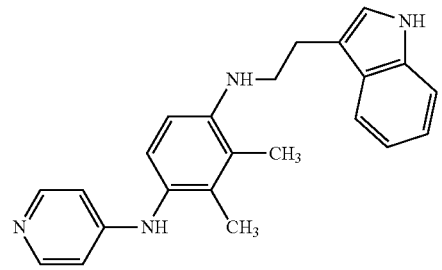

Comp. No. 1; mp. 186° C.

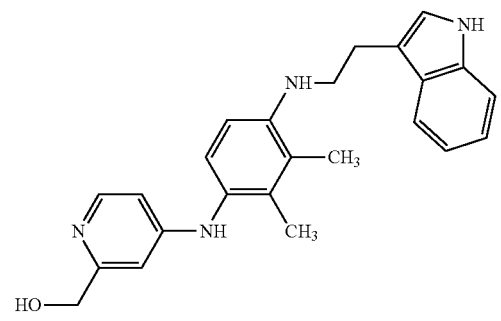

Comp. No. 2; mp. 163° C.

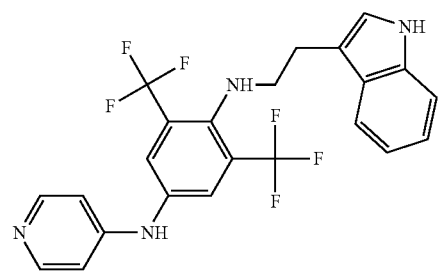

Comp. No. 3; mp. 187° C.

TABLE 2-continued
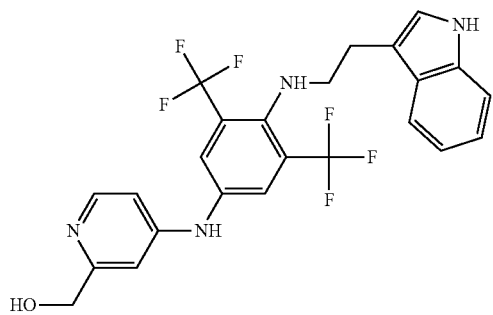
Comp. No. 4; mp. 164° C.
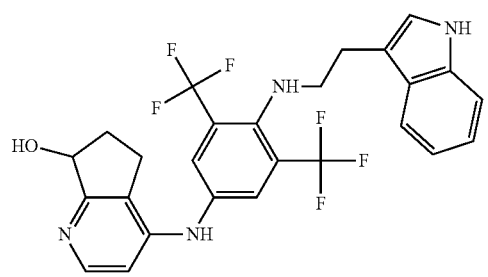
Comp. No. 5; mp. 178° C.
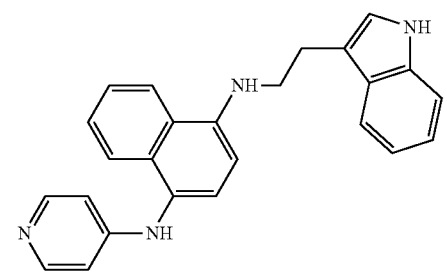
.1.5 HCl; Comp. No. 6; mp. 166° C.
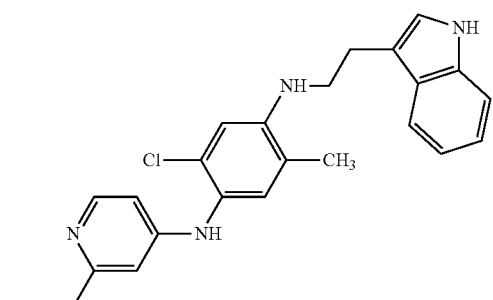
Comp. No. 7; mp. 205° C.
TABLE 2-continued
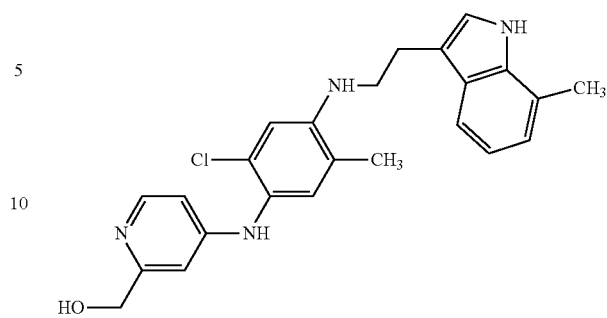
Comp. No. 8; mp. 163° C.
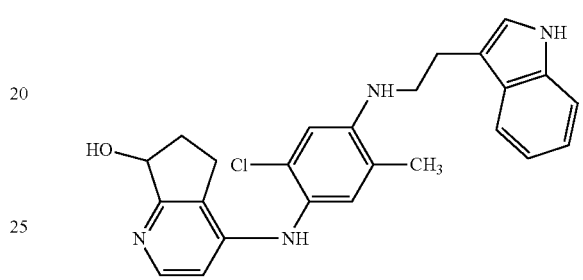
Comp. No. 9; mp. 207° C.
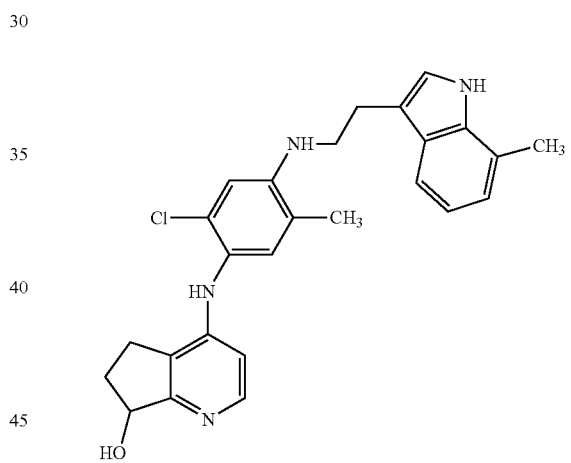
Comp. No. 10; mp. 237° C.
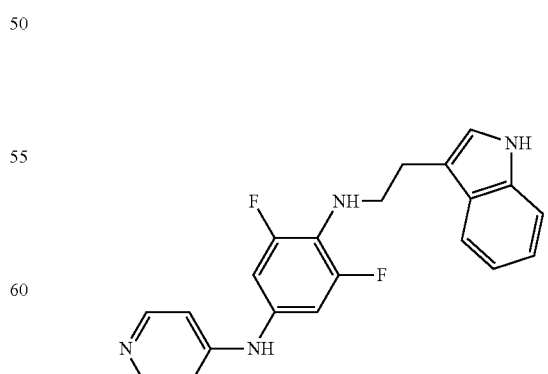
Comp. No. 11; mp. 164° C.

TABLE 2-continued
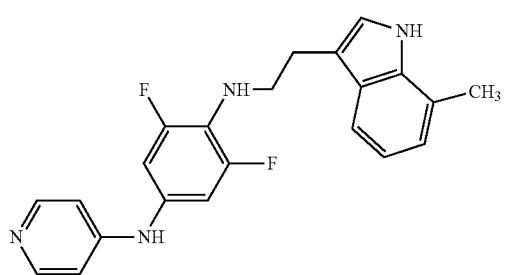
Comp. No. 12; mp. 80° C.
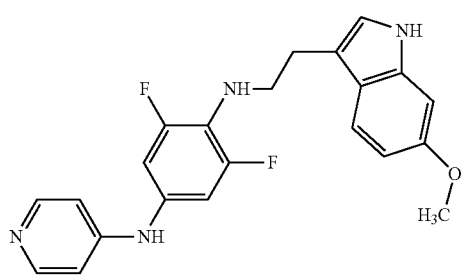
Comp. No. 13; mp. 170° C.
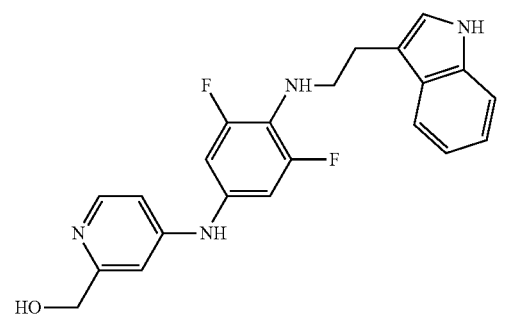
.1.52 HCl; Comp. No. 14; mp. 110° C.
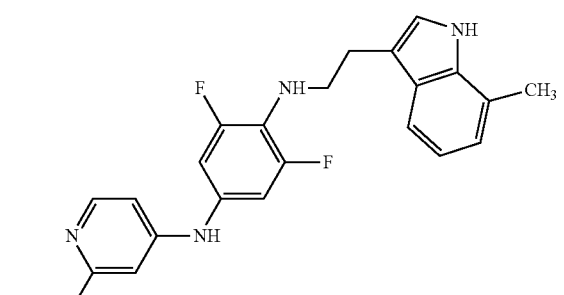
Comp. No. 15; mp. 166° C.
TABLE 2-continued
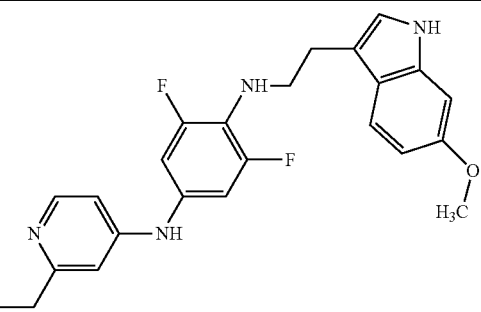
Comp. No. 16; mp. 135° C.
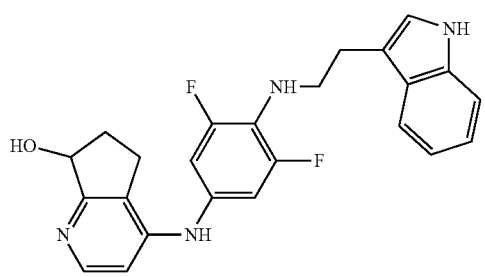
Comp. No. 17; mp. 147° C.
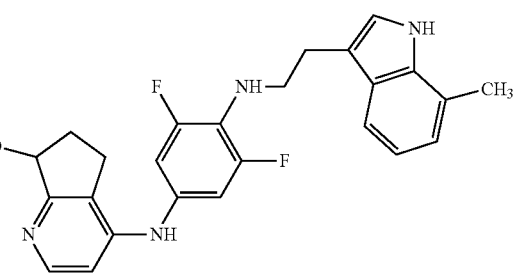
Comp. No. 18; mp. 200° C.
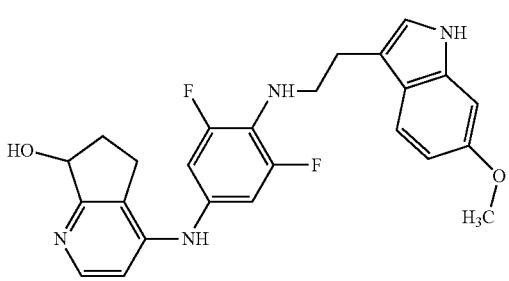
Comp. No. 19; mp. 180° C.
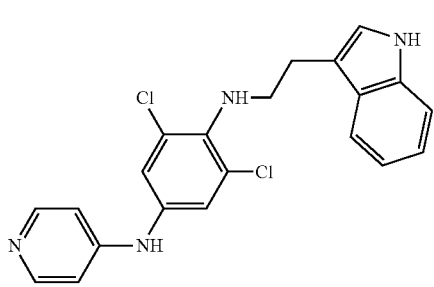
Comp. No. 20; mp. 161° C.

TABLE 2-continued
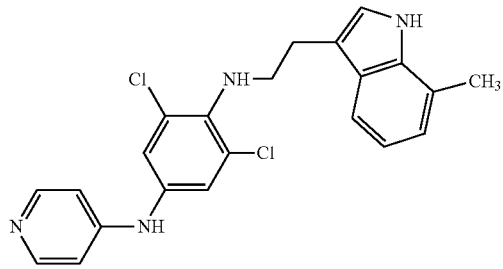
Comp. No. 21; mp. 132° C.
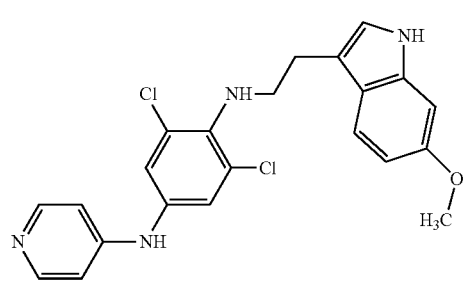
Comp. No. 22; mp. 154° C.
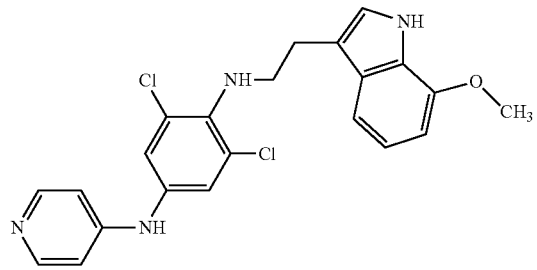
Comp. No. 23; mp. 146° C.
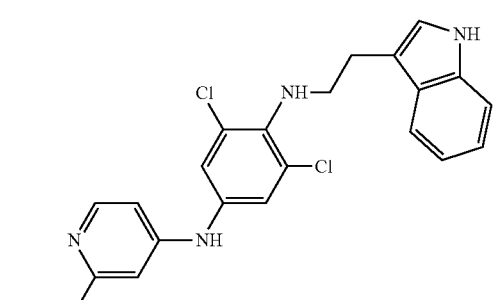
Comp. No. 24; mp. 115° C.
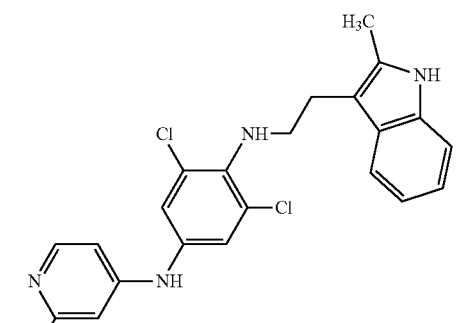
Comp. No. 25; mp. 186° C.
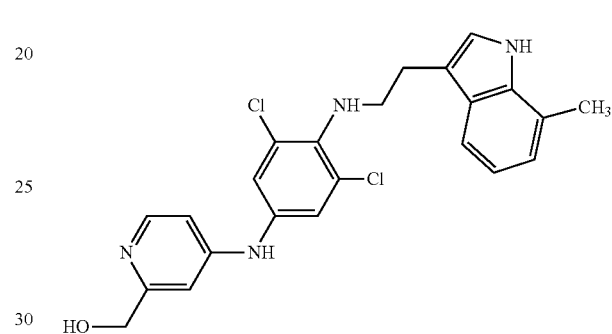
Comp. No. 26; mp. 170° C.
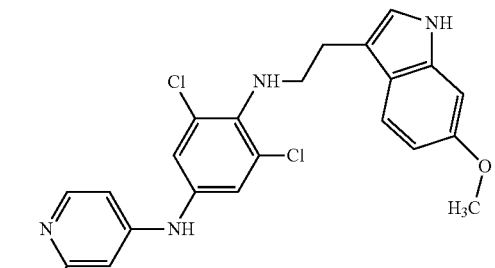
Comp. No. 27; mp. 241° C.
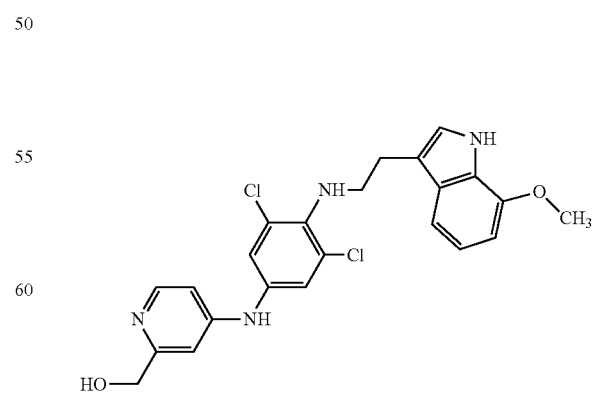
Comp. No. 28; mp. 160° C.

TABLE 2-continued
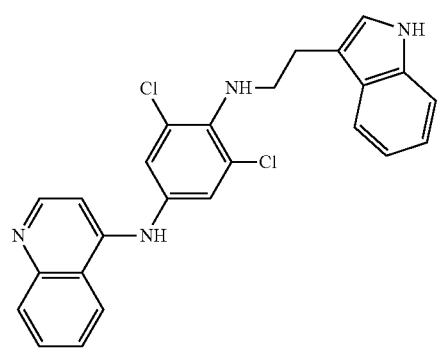
Comp. No. 29; mp. 158° C.
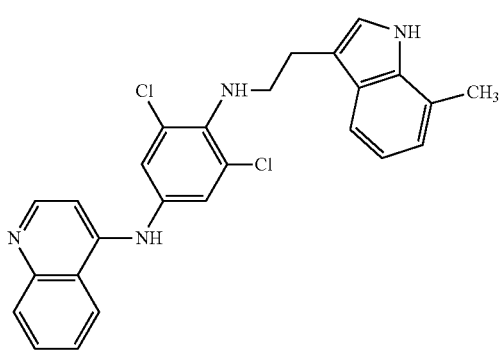
.0.97 HCl; Comp. No. 30; mp. 214° C.
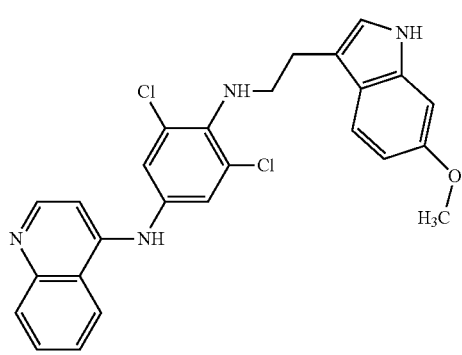
Comp. No. 31; mp. 175° C.
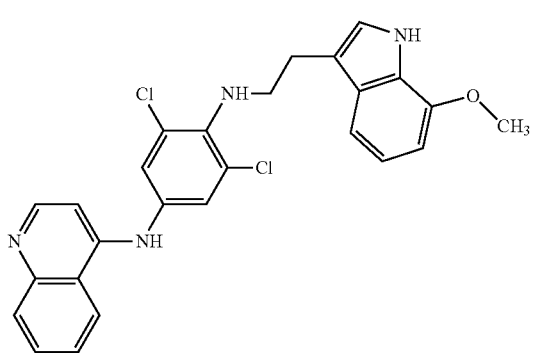
Comp. No. 32; mp. 203° C.
TABLE 2-continued
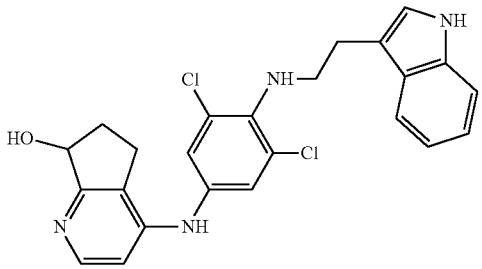
Comp. No. 33; mp. 151° C.
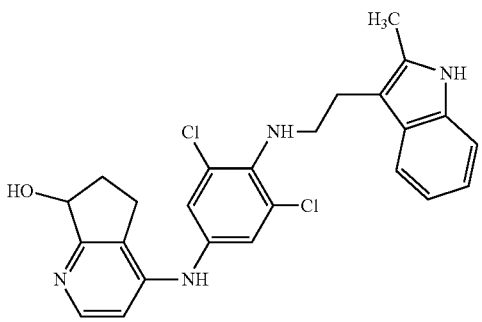
.0.98 HCl; Comp. No. 34; mp. 260° C.
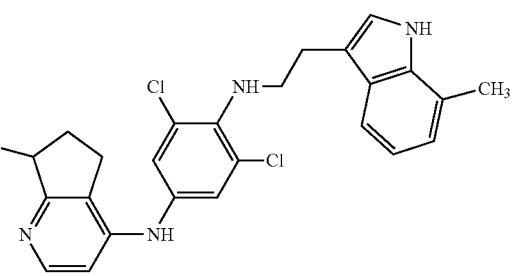
Comp. No. 35; mp. 202° C.
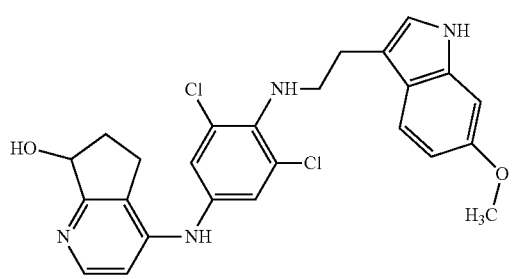
Comp. No. 36; mp. 203° C.
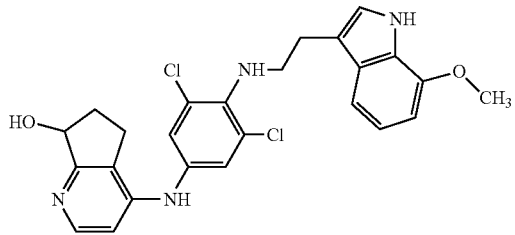
Comp. No. 37; mp. 196° C.

TABLE 2-continued
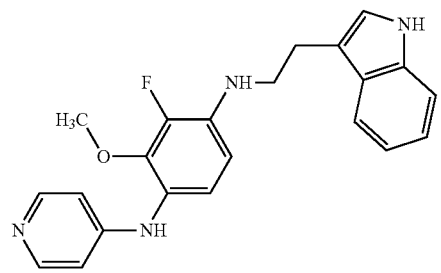
Comp. No. 38; mp. 90° C.
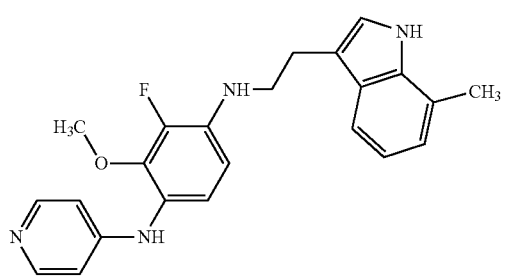
Comp. No. 39; mp. 124° C.
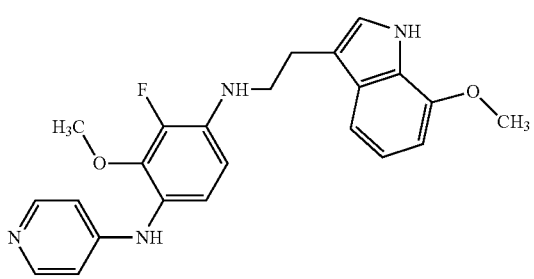
Comp. No. 40; mp. 93° C.
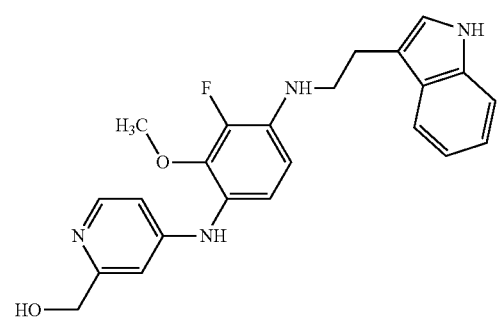
.1.31 HCl; Comp. No. 41; mp. 118° C.
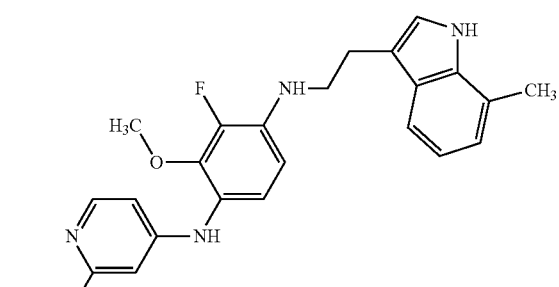
.Comp. No. 42; mp. 154° C.
TABLE 2-continued
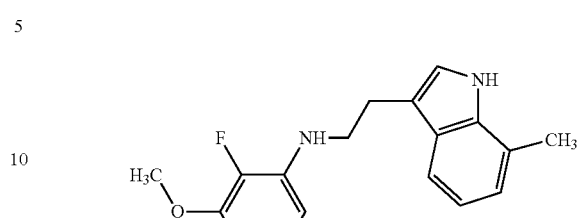
Comp. No. 44; mp. 121° C.
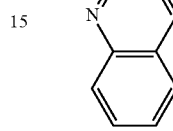
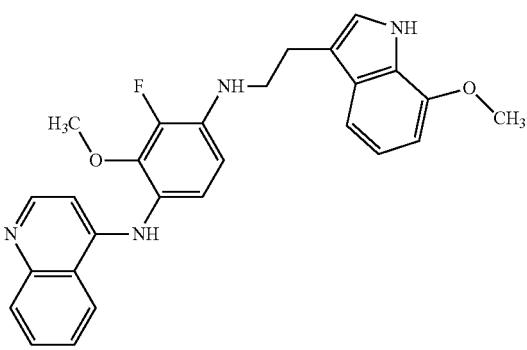
.1.56 HCl; Comp. No. 45; mp. 175° C.
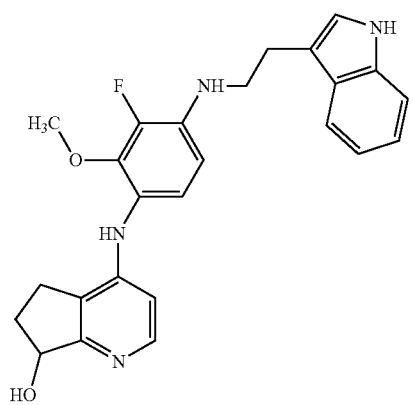
.1.2 HCl; Comp. No. 46; mp. 151° C.

TABLE 2-continued
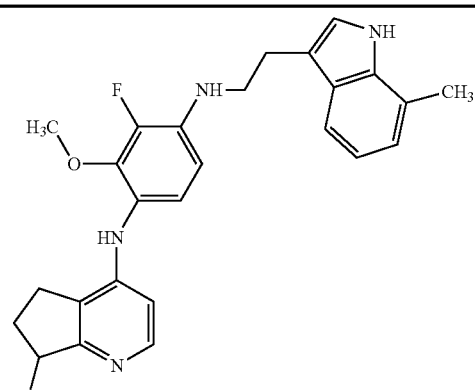
Comp. No. 47; mp. 196° C.
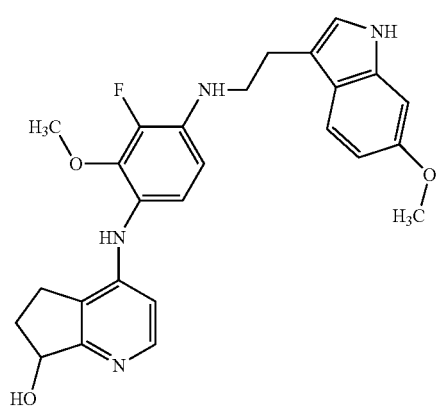
Comp. No. 48; mp. 194° C.
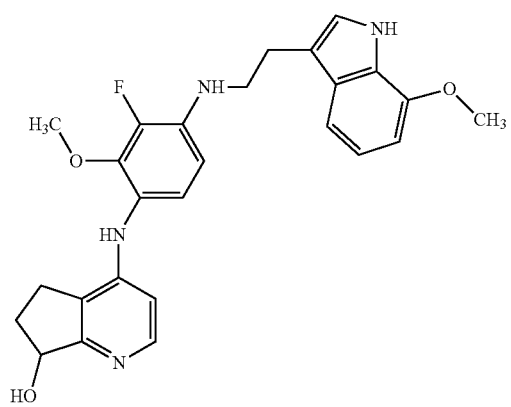
Comp. No. 49; mp. 123° C.
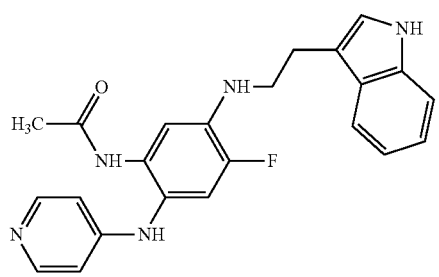
Comp. No. 50; mp. 241° C.
TABLE 2-continued
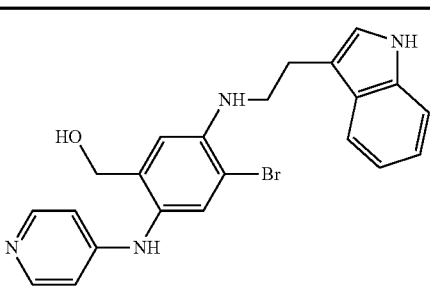
Comp. No. 51; mp. 230° C.
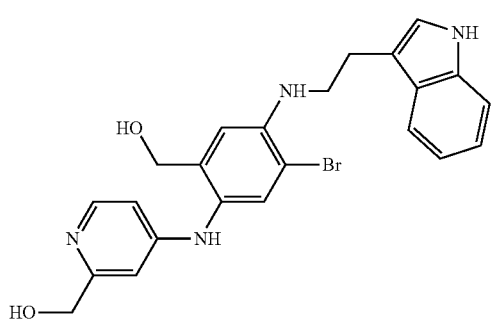
Comp. No. 52; mp. 198° C.
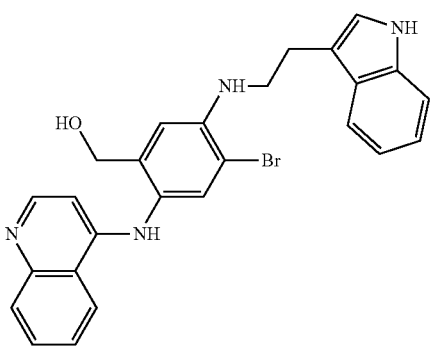
Comp. No. 53; mp. 192° C.
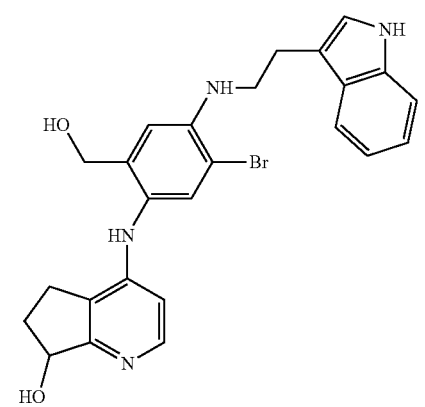
Comp. No. 54; mp. 240° C.

TABLE 2-continued
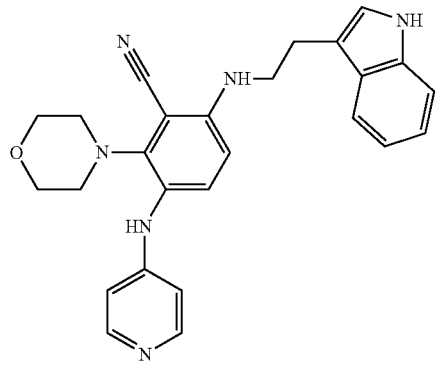
.0.99 HCl; Comp. No. 55; mp. 245° C.
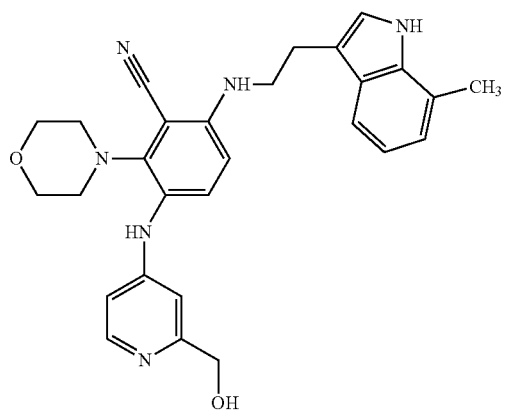
.1.32 HCl; Comp. No. 56; mp. 211° C.
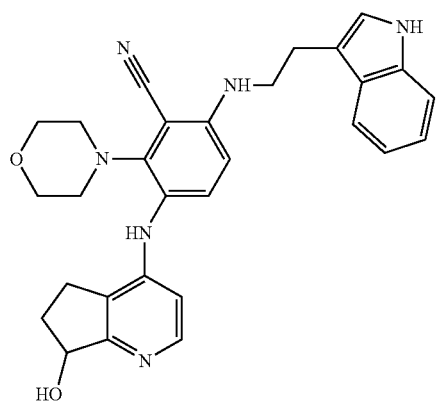
.HCl; Comp. No. 57; mp. 155° C.
TABLE 2-continued
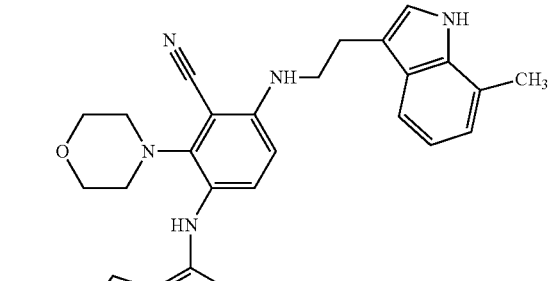
Comp. No. 58; mp. 168° C.
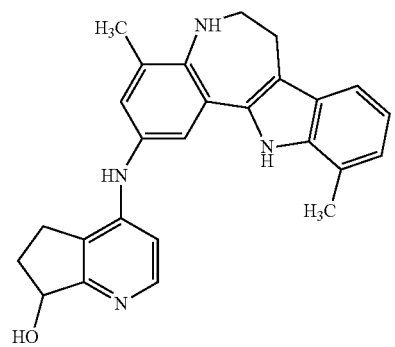
Comp. No. 59
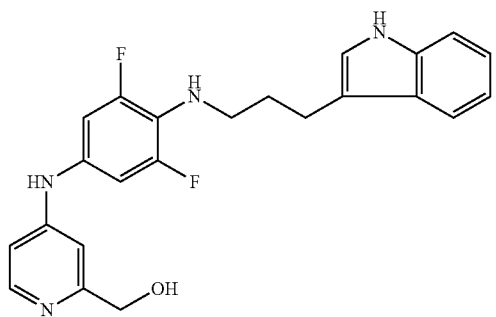
.095 HCl; Comp. No. 60; mp. 162° C.
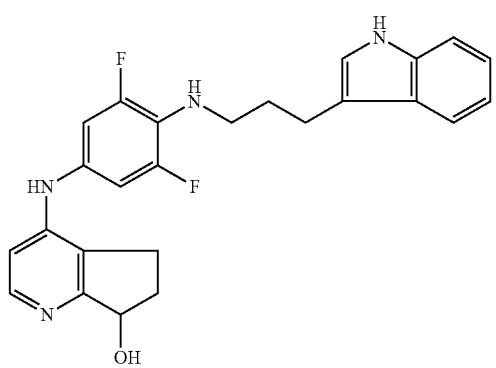
Comp. No. 61; mp. 171° C.

TABLE 2-continued

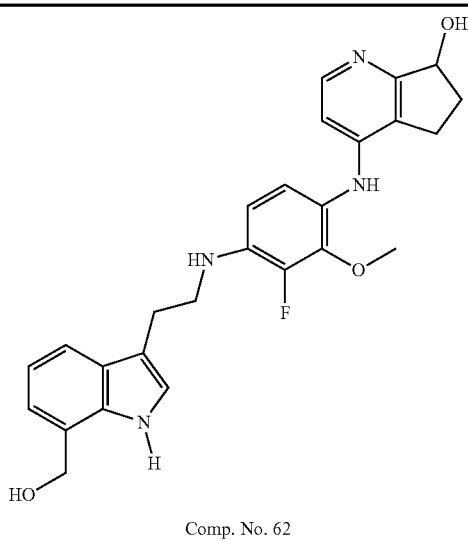

Comp. No. 62

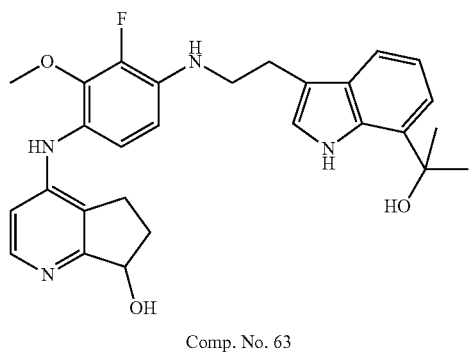 [SMILES: COc1c(Nc2ccnc3c2CCC3O)ccc(NCCc2c[nH]c3c(C(C)(C)O)cccc23)c1F]

Comp. No. 63

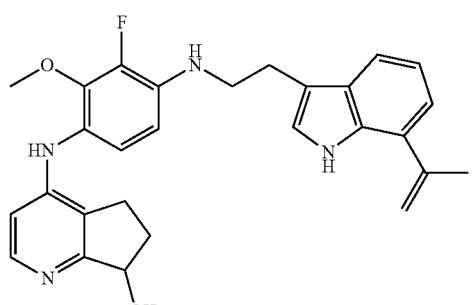

Comp. No. 64

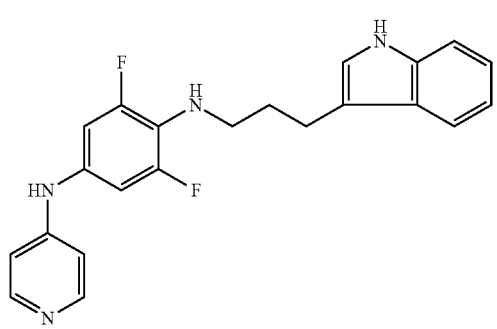

.1.18 HCl; Comp. No. 65; mp. 167° C.

In an embodiment, particularly preferred are compounds No. 2, 5, 6, 10, 12, 17, 25, 29, 30, 31, 33, 34, 35, 36, 37, 38, 39, 40, 41, 42, 43, 44, 45, 46, 47, 48 and 49, even more preferably compounds No. 5, 6, 10, 17, 29, 30, 31, 34, 35, 39, 40, 41, 42, 43, 44, 45, 46, 47, 48 and 49, and still more preferably compounds No. 5, 39, 41, 42, 43 and 47; which compounds may achieve particularly pronounced desired biological effects.

In another embodiment, particularly preferred are compounds No. 7, 9, 17, 29, 30, 31, 38, 39, 40, 41, 42, 43, 44, 45, 46, 47 and 49, even more preferably compound No. 42; which compounds may achieve particularly pronounced desired biological effects.

In a further embodiment, particularly preferred are compounds No. 2, 6, 8, 10, 11, 12, 13, 15, 17, 18, 19, 22, 29, 30, 31, 32, 38, 39, 40, 41, 42, 43, 44, 45, 46, 47, 48, 51, 52 and 53, even more preferably compounds No. 38, 39, 42, 44, 45, 46, and 47; which compounds may achieve particularly pronounced desired biological effects.

In a further embodiment, particularly preferred are the following compounds:

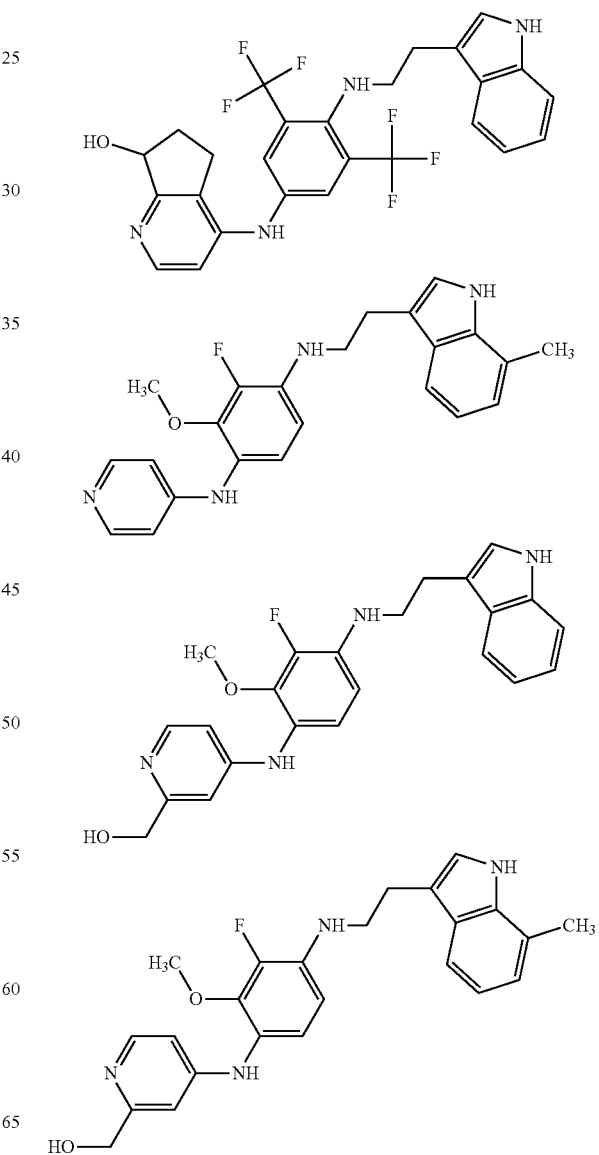

-continued

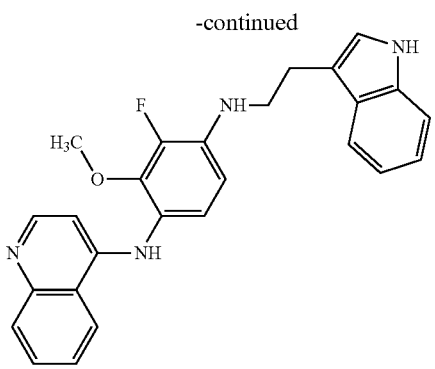

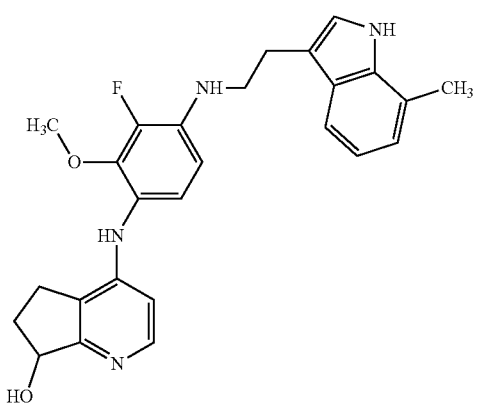

including any stereochemically isomeric form thereof; an N-oxide form thereof, an addition salt thereof or a solvate thereof.

In a further embodiment, particularly preferred are compounds No. 39, 41, 42, 47, 49 and 63.

The compounds of formula (I), their N-oxides, pharmaceutically acceptable salts, solvates, and stereochemically isomeric forms thereof may be prepared in conventional manner. The starting materials and some of the intermediates are known compounds and are commercially available or may be prepared according to conventional reaction procedures as generally known in the art.

A number of such preparation methods will be described hereinafter in more detail. Other methods for obtaining final compounds of formula (I) are described in the examples.

The compounds of formula (I) can be prepared by reacting an intermediate of formula (IV) with an intermediate of formula (V) wherein W is an appropriate leaving group such as, for example, halo, e.g., fluoro, chloro, bromo or iodo, or a sulfonyloxy radical such as methylsulfonyloxy, 4-methylphenylsulfonyloxy and the like. The reaction can be performed in a reaction-inert solvent such as, for example, an alcohol, e.g., methanol, ethanol, 2-methoxy-ethanol, propanol, butanol and the like; an ether, e.g., 1, 4-dioxane, mixture hydrochloric acid/1,4-dioxane, 1,1'-oxybispropane and the like; a ketone, e.g., 4-methyl-2-pentanone; or N,N-dimethylformamide, nitrobenzene, acetonitrile, acetic acid and the like or mixtures thereof. The addition of an appropriate base such as, for example, an alkali or earth alkaline metal carbonate or organic carbonate or organic base, e.g., triethylamine or sodium carbonate or N,N-diisopropylethanamine, may be utilized to neutralise the acid which is liberated during the course of the reaction. A small amount of an appropriate metal iodide, e.g., sodium or potassium iodide may be added to promote the reaction. Stirring may enhance the rate of the reaction. The reaction may conveniently be carried out at a temperature ranging between room temperature and the reflux temperature of the reaction mixture and, if desired, the reaction may be carried out at an increased pressure.

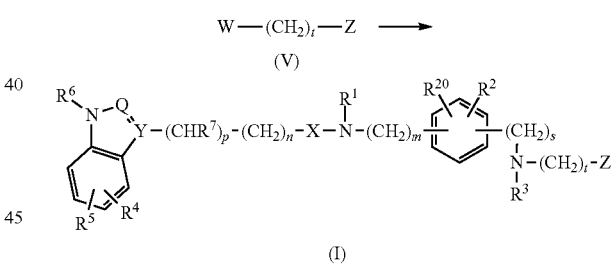

The compounds of formula (I), wherein X is $CH_2$, herein referred to as compounds of formula (I-a), can be prepared by reacting compounds of formula (I) wherein X is $C(=O)$, herein referred to as compounds of formula (I-b), with lithium aluminium hydride or $BH_3$ in a suitable solvent such as tetrahydrofuran.

(I-b)

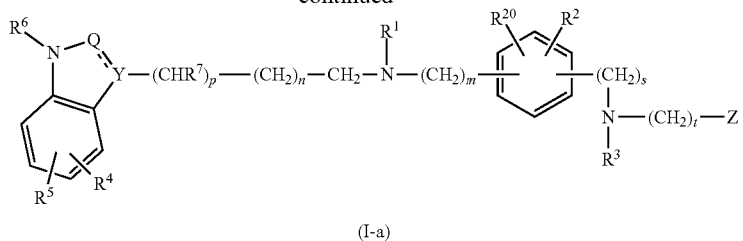

(I-a)

The compounds of formula (I-a) can also be prepared by reacting an appropriate carboxaldehyde of formula (VI), with an intermediate of formula (VII), in the presence of an appropriate reagent, such as a sodium borohydride, e.g., sodium tetrahydroborate or polymer supported cyanotrihydroborate, in a suitable solvent, such as an alcohol, e.g., methanol.

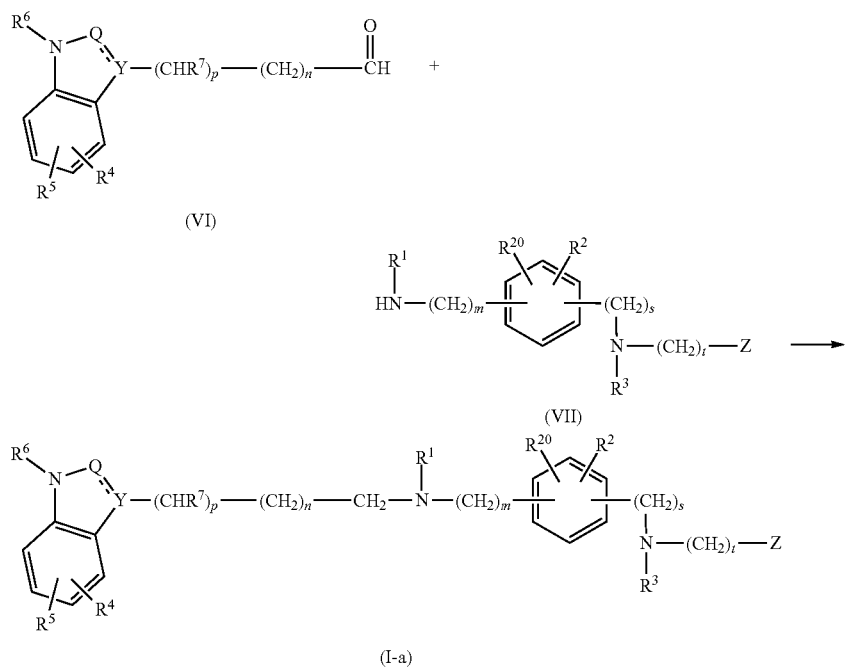

In an identical way the compounds of formula (I) wherein t is 1, herein referred to as compounds of formula (I-c), may be prepared by reacting an intermediate of formula (IV) with an appropriate carboxaldehyde of formula HC(=O)Z.

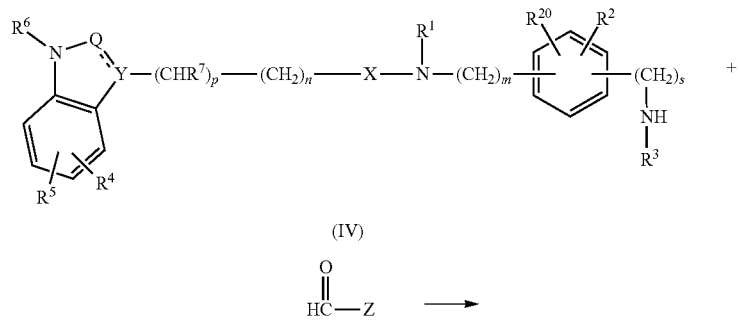

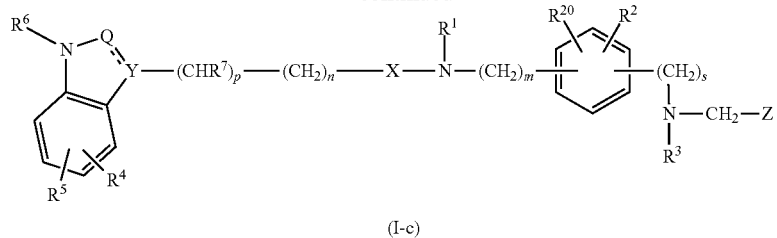

(I-c)

The compounds of formula (I), wherein s is 1, herein referred to as compounds of formula (I-d), can be prepared by reacting an intermediate of formula (VIII) with lithium aluminium hydride in a suitable solvent such as tetrahydrofuran.

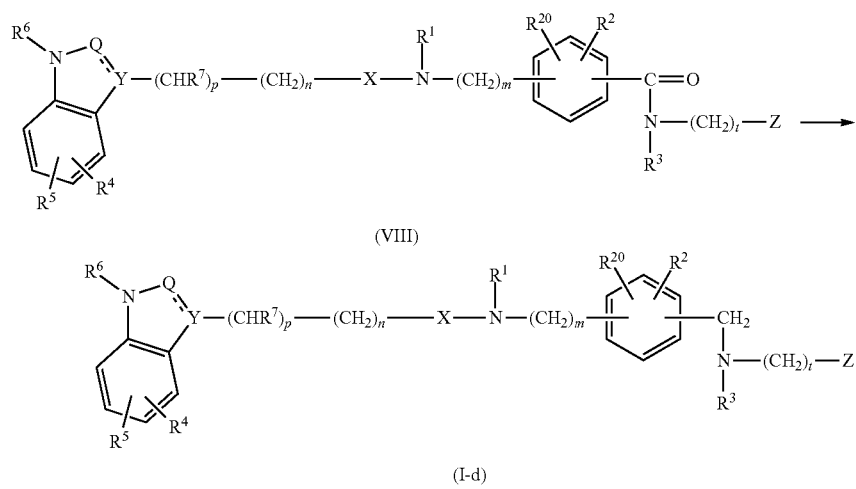

The compounds of formula (I) wherein $R^4$ is —$CH_2$—OH, herein referred to as compounds of formula (I-e), can be prepared by reacting an intermediate of formula (XXIV) with lithium aluminium hydride in a suitable solvent such as tetrahydrofuran.

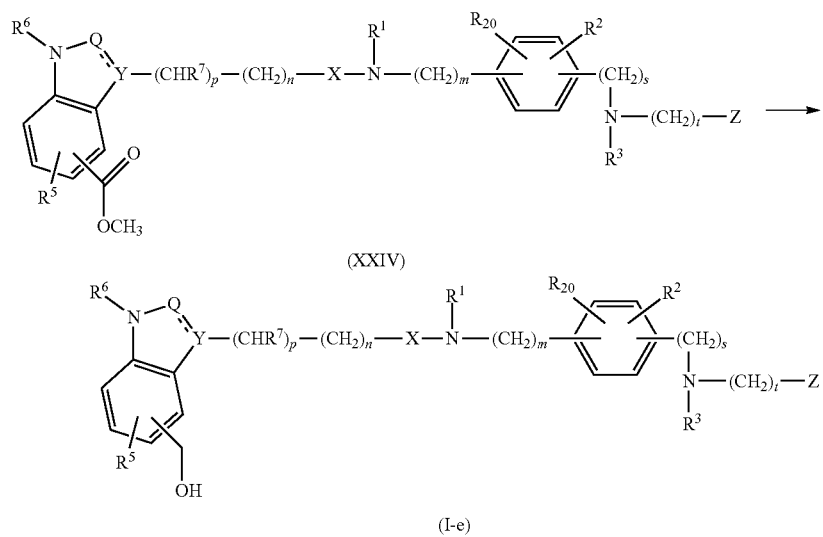

The compounds of formula (III) can be prepared by converting an intermediate of formula (XIX) in the presence of a strong acid, for example HCl, in a suitable solvent such as tetrahydrofuran.

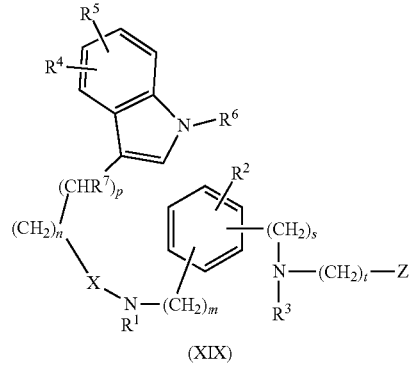

(XIX)

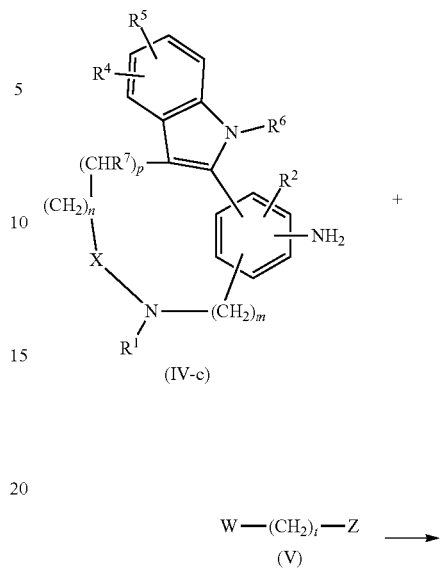

(IV-c)

+

W—(CH$_2$)$_t$—Z (V)

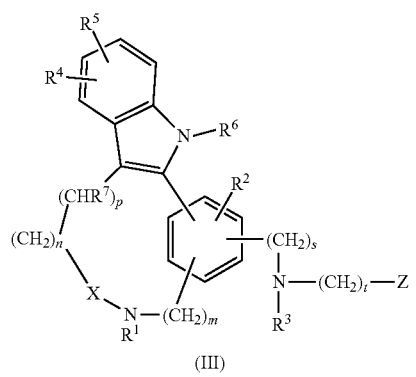

(III)

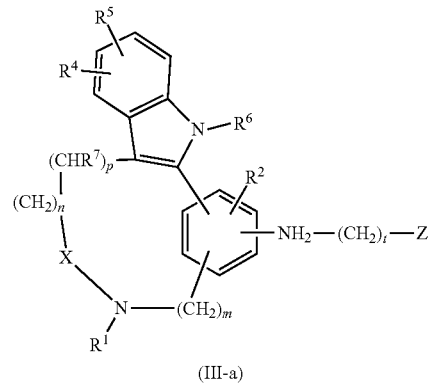

(III-a)

The compounds of formula (III) wherein s is 0 and R$^3$ is hydrogen, herein referred to as compounds of formula (III-a), can be prepared by reacting intermediates of formula (IV) wherein s is 0, R$^3$ is hydrogen,

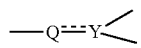

is —CR$^9$=C< and R$^9$ together with R$^{20}$ forms a direct bond, herein referred to as intermediates of formula (IV-c), with an intermediate of formula (V) wherein W is a suitable leaving group as defined above, in a reaction-inert solvent such as, for example, an alcohol, e.g., methanol, ethanol, 2-methoxyethanol, propanol, butanol and the like; an ether, e.g., 1,4-dioxane, 1,1'-oxybispropane and the like; a ketone, e.g., 4-methyl-2-pentanone; or N,N-dimethylformamide, nitrobenzene, acetonitrile, acetic acid and the like. The addition of an appropriate base such as, for example, an alkali or earth alkaline metal carbonate or organic base, e.g., triethylamine or sodium carbonate, may be utilized to neutralise the acid which is liberated during the course of the reaction.

The compounds of formula (III) wherein R$^B$ is hydrogen, herein referred to as compounds of formula (III-b), can also be prepared by Fisher indole synthesis starting form intermediates of formula (XXII) and (XXIII).

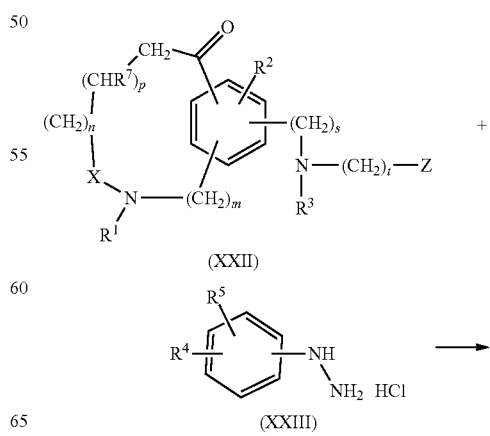

-continued

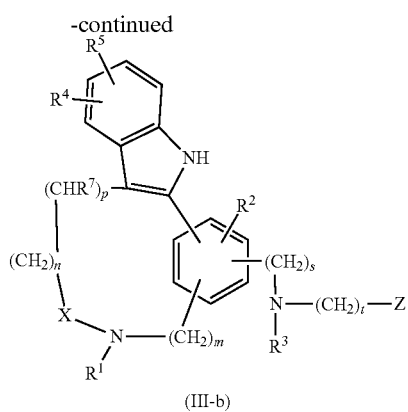

(III-b)

The compounds of formula (I) and their intermediates may also be converted into each other via art-known reactions or functional group transformations. A number of such transformations are already described hereinabove. Other examples are hydrolysis of carboxylic esters to the corresponding carboxylic acid or alcohol; hydrolysis of amides to the corresponding carboxylic acids or amines; hydrolysis of nitriles to the corresponding amides; amino groups on imidazole or phenyl may be replaced by a hydrogen by art-known diazotation reactions and subsequent replacement of the diazo-group by hydrogen; alcohols may be converted into esters and ethers; primary amines may be converted into to secondary or tertiary amines; double bonds may be hydrogenated to the corresponding single bond; an iodo radical on a phenyl group may be converted in to an ester group by carbon monoxide insertion in the presence of a suitable palladium catalyst; etc.

Intermediates of formula (IV), wherein X is $CH_2$, m is 0, s is 0 and $R^3$ is hydrogen, herein referred to as intermediates of formula (IV-a), can be prepared by a nitro to amine reduction reaction starting with an intermediate of formula (IX), in the presence of a suitable catalyst such as Raney Nickel or palladium on charcoal, and an appropriate reductant such as hydrogen, in a suitable solvent such as methanol, ethanol, toluene, tetrahydrofuran or mixtures thereof. For compounds bearing catalytic hydrogenation sensible moieties, Pt/C optionally poisoned with thiophene may be used. $V_2O_5$ may be used as an auxiliary catalyst. Suitable solvents for this reaction are tetrahydrofuran or toluene.

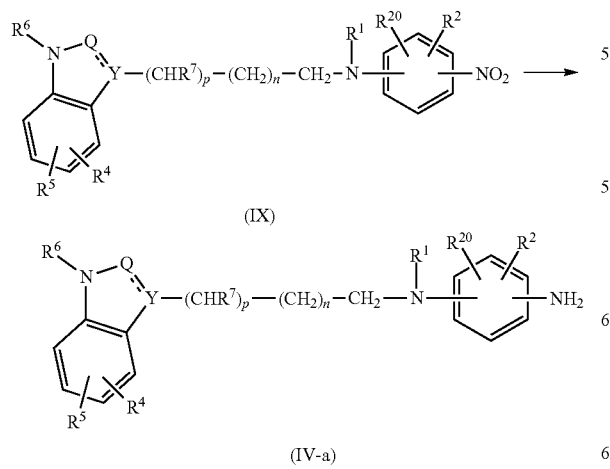

Intermediates of formula (IV), wherein X is C(=O), s is 0 and $R^3$ is hydrogen, herein referred to as intermediates of formula (IV-b), can be prepared by reacting an intermediate of formula (X) with an intermediate of formula (XI) in the presence of appropriate coupling reagents such as N'-(ethylcarbonimidoyl)-N,N-dimethyl-1,3-propanediamine, monohydrochloride (EDC) and 1-hydroxy-1H-benzotriazole (HOBT). The reaction may be performed in the presence of a base such as triethylamine, in a suitable solvent, such as, a mixture of dichloromethane and tetrahydrofuran.

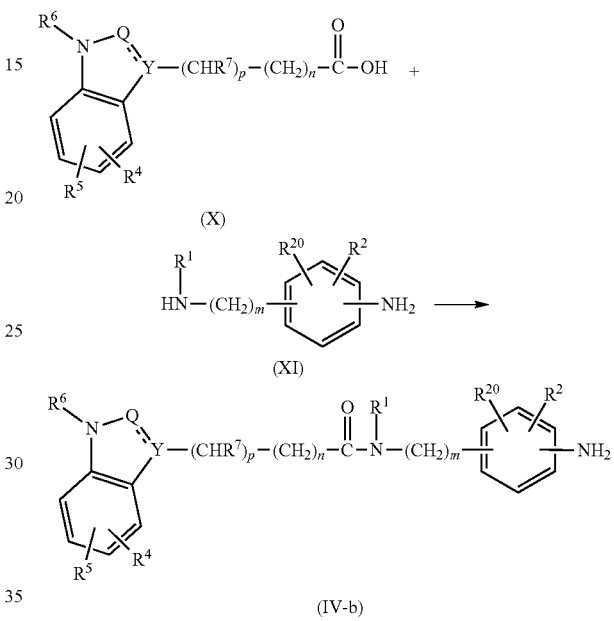

The intermediates of formula (VI) can be prepared by reacting intermediates of formula (XII) with lithium aluminium hydride in a suitable solvent such as tetrahydrofuran.

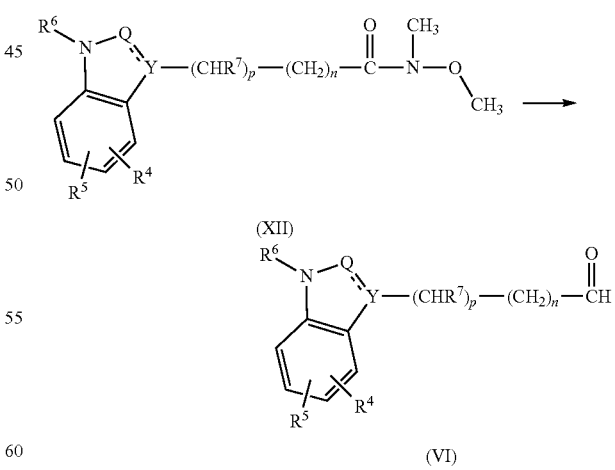

The intermediates of formula (VIII) can be prepared by reacting an intermediate of formula (XIII) with an intermediate of formula (XIV) in the presence of 2-Chloro-1-methylpyridinium iodide and triethylamine in a suitable solvent such as acetonitrile.

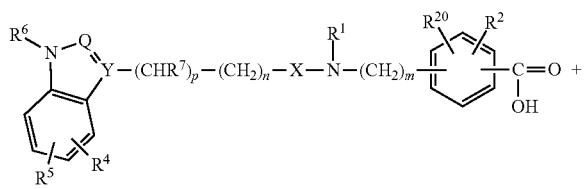

(XIII)

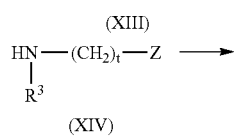

(XIV)

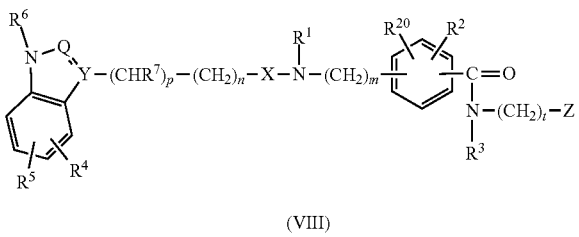

(VIII)

The intermediates of formula (IX) can be prepared by reacting an intermediate of formula (XV) with an intermediate of formula (XVI), wherein A is an appropriate leaving group such as, for example, halo, e.g., fluoro, chloro, bromo or iodo, or $C_{1-6}$alkyloxy, e.g., methyloxy, in a suitable solvent such as dimethylsulfoxide or toluene, preferably in the presence of a base such as $NaHCO_3$ or N,N-diisopropylethanamine, optionally at elevated temperatures such as at about 60° C.

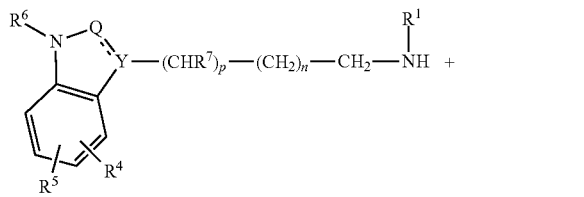

(XV)

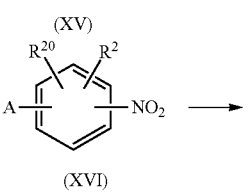

(XVI)

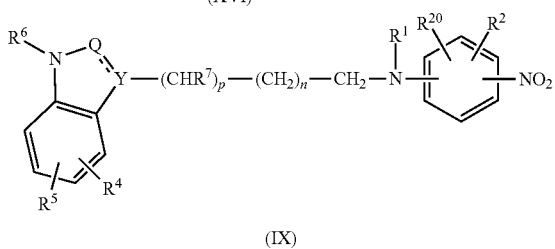

(IX)

The intermediates of formula (XIII) wherein $R^{20}$ represents —$CH_2$—OH, herein referred to as intermediates of formula (XVI-a), can be prepared by reducing an intermediate of formula (XXV) with a suitable reducing agent such as $NaBH_4$, in a suitable solvent such as an alcohol, e.g. methanol.

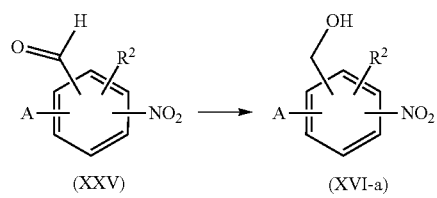

(XXV)  (XVI-a)

The intermediates of formula (XIII) can be prepared by converting an intermediate of formula (XVII) in the presence of sodium hydroxide and water, in a suitable solvent, such as ethanol.

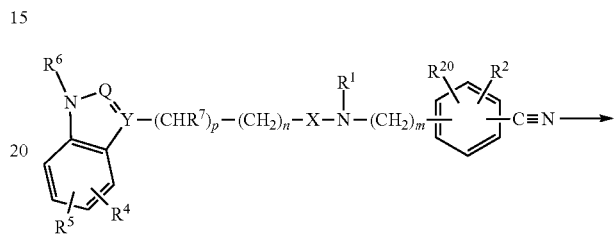

(XVII)

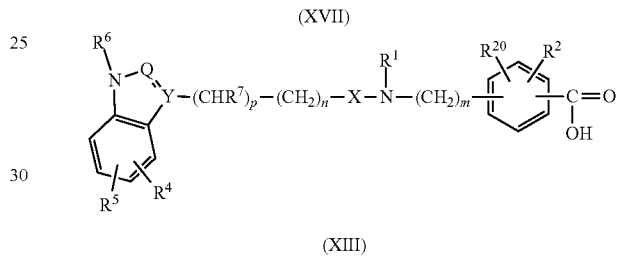

(XIII)

The intermediates of formula (XVII) can be prepared by reacting an intermediate of formula (XVIII), wherein A is a suitable leaving group as defined above, with an intermediate of formula (XV), in a suitable solvent such as diisopropylethyl amine.

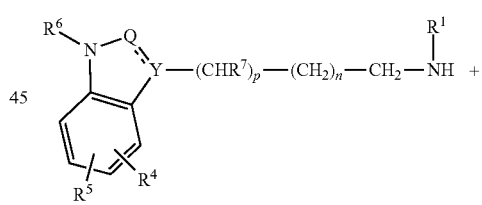

(XV)

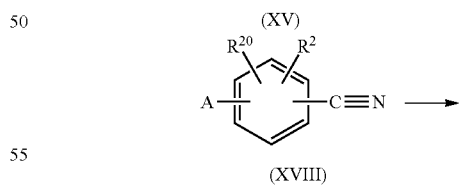

(XVIII)

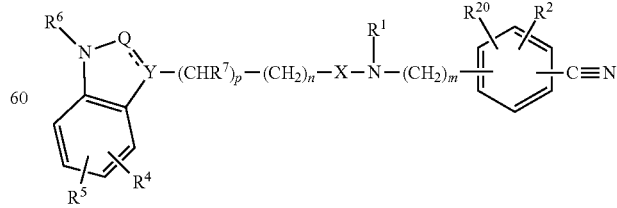

(XVII)

Intermediates of formula (XV) wherein $R^1$ represents hydrogen, herein referred to as intermediates of formula (XV-a), can be prepared by reacting an intermediate of formula (XXVI) in the presence of a suitable catalyst such as Raney nickel, ammonia, and a suitable solvent such as an alcohol, e.g. methanol.

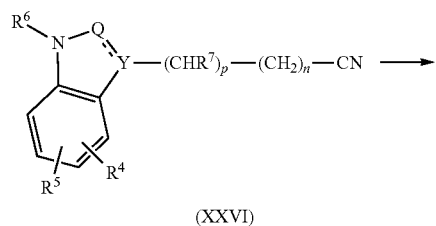

(XXVI)

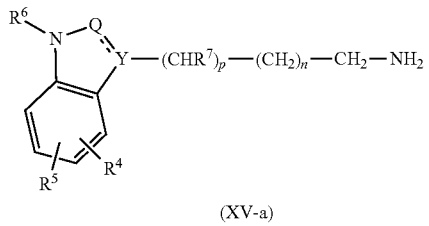

(XV-a)

Intermediates of formula (XXVI) can be prepared by reacting an intermediate of formula (XXVII) wherein C represents a suitable counter ion such as e.g. iodide, with sodium cyanide in a suitable solvent such as N,N-dimethylformamide.

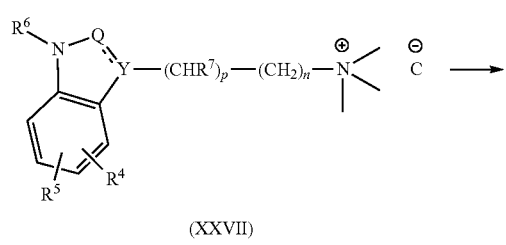

(XXVII)

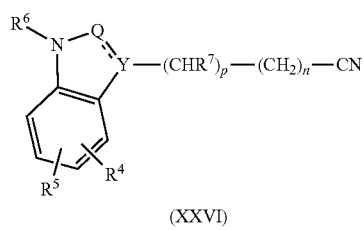

(XXVI)

Intermediates of formula (XXVI) wherein $R^4$ or $R^5$ represents hydroxy$C_{1-6}$alkyl (e.g. —CH(CH$_3$)—OH or —C(CH$_3$)$_2$—OH) can be prepared from the corresponding aldehyde or ketone compound (e.g. —C(=O)H or —C(=O)—CH$_3$) by reaction with methyl magnesium chloride in a suitable solvent such as tetrahydrofuran.

Intermediates of formula (XXVI) wherein $R^4$ or $R^5$ represents —C(=O)—CH$_3$ can be prepared from the corresponding —CH(CH$_3$)—OH compound by reaction with a suitable oxidizing reagent such as Dess Martin's reagent.

Intermediates of formula (XXVII) can be prepared from the corresponding secondary amine by reaction with a suitable alkylating agent such as methyl iodide, in a suitable solvent such as an alcohol, e.g. ethanol.

Intermediates of formula (IV-c) can be prepared by a nitro to amine reduction reaction starting with an intermediate of formula (XX), in the presence of a metal catalyst such as Raney Nickel and an appropriate reductant such as hydrogen, in a suitable solvent such as methanol or ethanol.

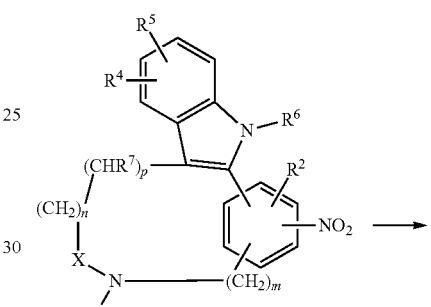

(XX)

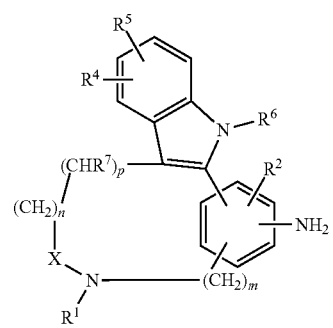

(IV-c)

Intermediates of formula (XX) can be prepared from intermediates of formula (XXI) wherein D is an appropriate halogen leaving group such as for example bromo or iodo, by cyclic Heck reaction in the presence of a base such as for example MgO and an organopalladium catalyst such as for example Pd(OAc)$_2$, in a suitable inert polar solvent such as an alcohol, e.g., methanol, acetonitrile or DMF.

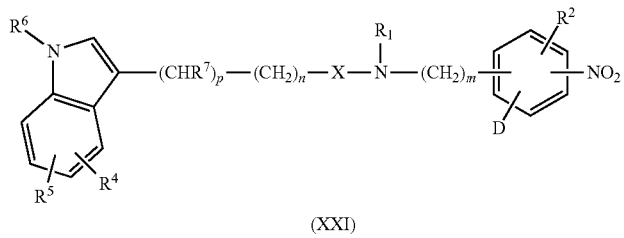 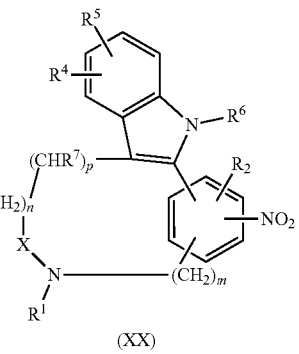

The intermediates of formula (XIX) or (XXIV) can be prepared according to the reaction described above for the preparation of compounds of formula (I) from intermediates of formula (IV) and (V).

Some compounds of formula (I) and some of the intermediates may have at least one stereogenic centre in their structure. Any such stereogenic centre may be independently present in an R or an S configuration.

Some of the compounds of formula (I) and some of the intermediates in the present invention may contain an asymmetric carbon atom. Such compounds as prepared in the hereinabove described processes may generally be racemic mixtures of enantiomers or diastereoisomers, which can be separated from one another following art-known resolution procedures. For example, diastereoisomers can be separated by physical methods such as selective crystallization or chromatographic techniques, e.g., counter current distribution, liquid chromatography and the like methods. Enantiomers can be obtained from racemic mixtures by first converting said racemic mixtures with suitable resolving agents such as, for example, chiral acids, to mixtures of diastereomeric salts or compounds; then physically separating said mixtures of diastereomeric salts or compounds by, for example, selective crystallization, supercritical fluid chromatography or chromatographic techniques, e.g., liquid chromatography and the like methods; and finally converting said separated diastereomeric salts or compounds into the corresponding enantiomers. Pure stereochemically isomeric forms may also be obtained from the pure stereochemically isomeric forms of the appropriate intermediates and starting materials, provided that the intervening reactions occur stereospecifically.

The compounds of formula (I), pharmaceutically acceptable acid or base addition salts, solvates, N-oxides and stereoisomeric forms thereof have valuable pharmacological properties in that they inhibit the interaction between p53 and MDM2.

The term "MDM2" (Murine Double Minute2) is used herein to mean a protein obtained as a result of expression of the mdm2 gene. Within the meaning of this term, MDM2 encompass all proteins encoded by mdm2, mutants thereof, alternative slice proteins thereof, and phosphorylated proteins thereof. Additionally, as used herein, the term "MDM2" includes MDM2 analogues, e.g. MDMX, also known as MDM4, and MDM2 homologues and analogues of other animals, e.g. the human homologue HDM2 or the human analogue HDMX.

The term "inhibiting the interaction" or "inhibitor of the interaction" is used herein to mean preventing or reducing the direct or indirect association of one or more molecules, peptides, proteins, enzymes or receptors; or preventing or reducing the normal activity of one or more molecules, peptides, proteins, enzymes, or receptors.

The term "inhibitor of the interaction of p53 with MDM2" or "p53-MDM2 inhibitor" is used herein to describe an agent which increases the expression of p53 in the assay described in C.1. This increase may be caused by, but is not limited to, one or more of the following mechanisms of action:

inhibiting the interaction between p53 and MDM2,
direct association with either the MDM2 or the p53 protein,
interactions with upstream or downstream targets, e.g. kinases, or enzyme activities involved in ubiquitination or SUMO modification,
sequestering or transportation of MDM2 and p53 into different cellular compartments,
modulation of proteins associating with MDM2, for example (but not limited to), p63, p73, E2F-1, Rb, p21waf1 or cip1, HIF1alpha, Foxo3A, p14ARF,
downregulating or interference with MDM2 expression and/or MDM2 activity, for example (but not limited to), impacting on its cellular localisation, post-translational modification, nuclear export, ubiquitin ligase activity or interference with binding of MDM2 with the proteasome, modulating the MDM2-proteasome interaction,
direct or indirect stabilization of the p53 protein, e.g. by keeping it in its functional structural form, or by preventing misfolding,
enhancing p53 expression or expression of p53 family members, e.g. p63 and p73.
increasing p53 activity, for example by (but not limited to), enhancing its transcriptional activity and/or
increasing expression of genes and proteins of the p53-signalling pathway, for example (but not limited to) p21waf1, cip1, MIC-1 (GDF-15), PIG-3, Bax, Puma, Noxa, and ATF-3.

Hence, the present invention discloses the compounds of formula (I) for use as a medicine, in particular for the treatment of cancer or related diseases, for inhibiting tumour growth, for inhibiting the interaction between MDM2 and p53, for modulating the MDM2-proteasome interaction.

Furthermore, the invention also concerns the use of a compound for the manufacture of a medicament for the treatment of a disorder mediated through a p53-MDM2 interaction, wherein said compound is a compound of formula (I)

The term "treating" or "treatment" as used herein covers any treatment of a disease and/or condition in an animal, particularly a human, and includes: (i) inhibiting the disease and/or condition, i.e., arresting its development; or (ii) relieving the disease and/or condition, i.e., causing regression of the disease and/or condition. In certain embodiments, the disclosed compounds additionally prevent a disease and/or condition from occurring in a subject which may be predisposed to the disease and/or condition but has not yet been diagnosed as having it.

With the term "a disorder mediated through a p53-MDM2 interaction" is meant any undesired or detrimental condition that results from the interaction between the MDM2 protein and p53 or other cellular proteins that induce apoptosis, induce cellular death, or regulate the cell cycle.

This invention also provides a method for treating a disorder mediated through a p53-MDM2 interaction by administering an effective amount of a compound of the present invention, to a subject, e.g. a mammal (and more particularly a human) in need of such treatment.

The compounds of the invention can have antiproliferative effects in tumour cells, even if such cells are devoid of functional p53. More in particular, the compounds of the invention can have antiproliferative effects in tumours with wild-type or mutant p53 and/or in tumours overexpressing MDM2.

Thus, this invention also provides a method for inhibiting tumour growth by administering an effective amount of a compound of the present invention, to a subject, e.g. a mammal (and more particularly a human) in need of such treatment.

Examples of tumours including adult and pediatric malignancies, which may be inhibited by the compounds of the present invention include, but are not limited to, lung cancer including small cell lung cancer and non-small cell lung cancer (e.g. adenocarcinoma), pancreatic cancers, colon cancers (e.g. colorectal carcinomas, such as, for example, colon adenocarcinoma and colon adenoma), oesophageal cancer, oral squamous carcinoma, tongue carcinoma, gastric carcinoma, liver cancer, nasopharyngeal cancer, hematopoietic tumours of lymphoid lineage (e.g. acute lymphocytic leukemia, B-cell lymphoma, Burkitt's lymphoma), non-Hodgkin's lymphoma (e.g. mantle cell lymphoma), Hodgkin's disease, myeloid leukemias (for example, acute myelogenous leukemia (AML) or chronic myelogenous leukemia (CML)), acute lymphoblastic leukemia, chronic lymphocytic leukemia (CLL), thyroid follicular cancer, myelodysplastic syndrome (MDS), tumours of mesenchymal origin, soft tissue sarcomas, liposarcomas, gastrointestinal stromal sarcomas, malignant peripheral nerve sheath tumours (MPNST), Ewing sarcomas, leiomyosarcomas, mesenchymal chondrosarcomas, lymphosarcomas, fibrosarcomas, rhabdomyosarcomas, melanomas, teratocarcinomas, neuroblastomas, brain tumours, gliomas, benign tumour of the skin (e.g. keratoacanthomas), breast carcinoma (e.g. advanced breast cancer), kidney carcinoma, ovary carcinoma, cervical carcinoma, endometrial carcinoma, bladder carcinoma, prostate cancer including the advanced disease and hormone refractory prostate cancer, testicular cancers, osteosarcoma, head and neck cancer, epidermal carcinoma, multiple myeloma (e.g. refractory multiple myeloma), mesothelioma. Particular cancers that can be treated with the compounds of the present invention are breast cancer, colorectal cancer, non-small cell lung cancer, acute myelogenous leukemia (AML).

The compounds of the present invention can also be used for the treatment and prevention of inflammatory conditions.

Thus, this invention also provides a method for the treatment and prevention of inflammatory conditions by administering an effective amount of a compound of the present invention, to a subject, e.g. a mammal (and more particularly a human) in need of such treatment.

The compounds of the present invention can also be used for the treatment of autoimmune diseases and conditions. With the term "autoimmune diseases" is meant any disease in which an animal's immune system reacts adversely to a self-antigen. With the term "self-antigen" is meant any antigen that is normally found in the animal's body. Representative autoimmune diseases include but are not limited to: Hashimoto's thyroiditis, Grave's disease, multiple sclerosis, pernicious anemia, Addison's disease, insulin-dependent diabetes mellitus, rheumatoid arthritis, systemic lupus erythematosus (SLE or lupus), dermatomyositis, Crohn's disease, Wegener's granulomatosis, Anti Glomerular Basement Membrane Disease, Antiphospholipid Syndrome, 25 Dermatitis Herpetiformis, Allergic Encephalomyelitis, Glomerulonephritis, Membranous Glomerulonephritis, Goodpasture Syndrome, Lambert-Eaton, Myasthenic Syndrome, Myasthenia Gravis, Bullous Pemphigoid, Polyendocrinopathies, Reiter's Disease, and Stiff-Man Syndrome.

Thus, this invention also provides a method for the treatment of autoimmune diseases and conditions by administering an effective amount of a compound of the present invention, to a subject, e.g. a mammal (and more particularly a human) in need of such treatment.

The compounds of the present invention can also be useful for the treatment of diseases associated with conformational unstable or misfolded proteins.

Examples of diseases associated with conformational unstable or misfolded proteins include but are not limited to: cystic fibrosis (CFTR), Marfan syndrome (fibrillin), Amyotrophic lateral sclerosis (superoxide dismutase), scurvy (collagen), maple syrup urine disease (alpha-ketoacid dehydrogenase complex), osteogenesis imperfecta (typeI procollagen pro-alpha), Creutzfeldt-Jakob disease (prion), Alzheimer's disease (beta-amyloid), familial amyloidosis (lysozyme), cataracts (crystallins), familial hypercholesterolemia (LDL receptor), □ I-antitrypsin deficiency, Tay-Sachs disease (beta-hexosaminidase), retinitis pigmentosa (rhodopsin), and leprechaunism (insulin receptor).

Thus, this invention also provides a method for the treatment of diseases associated with conformational unstable or misfolded proteins by administering an effective amount of a compound of the present invention, to a subject, e.g. a mammal (and more particularly a human) in need of such treatment.

In view of their useful pharmacological properties, the subject compounds may be formulated into various pharmaceutical forms for administration purposes.

To prepare the pharmaceutical compositions of this invention, an effective amount of a compound of the present invention, as the active ingredient is combined in intimate admixture with a pharmaceutically acceptable carrier, which carrier may take a wide variety of forms depending on the form of preparation desired for administration. These pharmaceutical compositions are desirably in unitary dosage form suitable, preferably, for administration orally, rectally, percutaneously, or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules and tablets.

Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, to aid solubility for example, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wetting agent, optionally combined with suitable additives of any nature in minor proportions, which additives do not cause a significant deleterious effect to the skin. Said additives may facilitate the administration to the skin and/or may be helpful for preparing the desired compositions. These compositions may be administered in various ways, e.g., as a transdermal patch, as a spot-on, as an ointment. It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient, calculated to produce the desired therapeutic effect, in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

The compound of the invention is administered in an amount sufficient to inhibit the interaction between MDM2 and p53 or other cellular proteins that induce apoptosis, induce cellular death, regulate the cell cycle, regulate tumor cell migration or invasion or metastasis, in particular an amount sufficient to modulate the MDM2-proteasome interaction.

The oncogenic potential of MDM2 is not only determined by its ability to suppress p53, but also by its ability to regulate other tumour suppressor proteins, e.g. the retinoblastoma protein pRb and the closely associated E2F1 transcription factor, p63, p73.

Thus, the compound of the invention is administered in an amount sufficient to modulate the interaction between MDM2 and the E2F1 transcription factors.

Those skilled in the art could easily determine the effective amount from the test results presented hereinafter. In general it is contemplated that a therapeutically effective amount would be from 0.005 mg/kg to 100 mg/kg body weight, and in particular from 0.005 mg/kg to 10 mg/kg body weight. It may be appropriate to administer the required dose as single, two, three, four or more sub-doses at appropriate intervals throughout the day. Said sub-doses may be formulated as unit dosage forms, for example, containing 0.5 to 500 mg, in particular 1 mg to 500 mg, more in particular 10 mg to 500 mg of active ingredient per unit dosage form.

Depending on the mode of administration, the pharmaceutical composition will preferably comprise from 0.05 to 99% by weight, more preferably from 0.1 to 70% by weight, even more preferably from 0.1 to 50% by weight of the compound of the present invention, and, from 1 to 99.95% by weight, more preferably from 30 to 99.9% by weight, even more preferably from 50 to 99.9% by weight of a pharmaceutically acceptable carrier, all percentages being based on the total weight of the composition.

As another aspect of the present invention, a combination of a p53-MDM2 inhibitor with another anticancer agent is envisaged, especially for use as a medicine, more specifically in the treatment of cancer or related diseases.

For the treatment of the above conditions, the compounds of the invention may be advantageously employed in combination with one or more other medicinal agents, more particularly, with other anti-cancer agents or adjuvants in cancer therapy. Examples of anti-cancer agents or adjuvants (supporting agents in the therapy) include but are not limited to:

platinum coordination compounds for example cisplatin optionally combined with amifostine, carboplatin or oxaliplatin;

taxane compounds for example paclitaxel, paclitaxel protein bound particles (Abraxane™) or docetaxel;

topoisomerase I inhibitors such as camptothecin compounds for example irinotecan, SN-38, topotecan, topotecan hcl;

topoisomerase II inhibitors such as anti-tumour epipodophyllotoxins or podophyllotoxin derivatives for example etoposide, etoposide phosphate or teniposide;

anti-tumour vinca alkaloids for example vinblastine, vincristine or vinorelbine;

anti-tumour nucleoside derivatives for example 5-fluorouracil, leucovorin, gemcitabine, gemcitabine hcl, capecitabine, cladribine, fludarabine, nelarabine;

alkylating agents such as nitrogen mustard or nitrosourea for example cyclophosphamide, chlorambucil, carmustine, thiotepa, mephalan (melphalan), lomustine, altretamine, busulfan, dacarbazine, estramustine, ifosfamide optionally in combination with mesna, pipobroman, procarbazine, streptozocin, telozolomide, uracil;

anti-tumour anthracycline derivatives for example daunorubicin, doxorubicin optionally in combination with dexrazoxane, doxil, idarubicin, mitoxantrone, epirubicin, epirubicin hcl, valrubicin;

molecules that target the IGF-1 receptor for example picropodophilin;

tetracarcin derivatives for example tetracarcin A;

glucocorticoiden for example prednisone;

antibodies for example trastuzumab (HER2 antibody), rituximab (CD20 antibody), gemtuzumab, gemtuzumab ozogamicin, cetuximab, pertuzumab, bevacizumab, alemtuzumab, eculizumab, ibritumomab tiuxetan, nofetumomab, panitumumab, tositumomab, CNTO 328;

estrogen receptor antagonists or selective estrogen receptor modulators or inhibitors of estrogen synthesis for example tamoxifen, fulvestrant, toremifene, droloxifene, faslodex, raloxifene or letrozole;

aromatase inhibitors such as exemestane, anastrozole, letrazole, testolactone and vorozole;
differentiating agents such as retinoids, vitamin D or retinoic acid and retinoic acid metabolism blocking agents (RAMBA) for example accutane;
DNA methyl transferase inhibitors for example azacytidine or decitabine;
antifolates for example premetrexed disodium;
antibiotics for example antinomycin D, bleomycin, mitomycin C, dactinomycin, carminomycin, daunomycin, levamisole, plicamycin, mithramycin;
antimetabolites for example clofarabine, aminopterin, cytosine arabinoside or methotrexate, azacitidine, cytarabine, floxuridine, pentostatin, thioguanine;
apoptosis inducing agents and antiangiogenic agents such as Bcl-2 inhibitors for example YC 137, BH 312, ABT 737, gossypol, HA 14-1, TW 37 or decanoic acid;
tubuline-binding agents for example combrestatin, colchicines or nocodazole:
kinase inhibitors (e.g. EGFR (epithelial growth factor receptor) inhibitors, MTKI (multi target kinase inhibitors), mTOR inhibitors) for example flavoperidol, imatinib mesylate, erlotinib, gefitinib, dasatinib, lapatinib, lapatinib ditosylate, sorafenib, sunitinib, sunitinib maleate, temsirolimus;
farnesyltransferase inhibitors for example tipifarnib;
histone deacetylase (HDAC) inhibitors for example sodium butyrate, suberoylanilide hydroxamide acid (SAHA), depsipeptide (FR 901228), NVP-LAQ824, R306465, JNJ-26481585, trichostatin A, vorinostat;
Inhibitors of the ubiquitin-proteasome pathway for example PS-341, MLN 0.41 or bortezomib;
Yondelis;
Telomerase inhibitors for example telomestatin;
Matrix metalloproteinase inhibitors for example batimastat, marimastat, prinostat or metastat.
Recombinant interleukins for example aldesleukin, denileukin diftitox, interferon alfa 2a, interferon alfa 2b, peginterferon alfa 2b
MAPK inhibitors
Retinoids for example alitretinoin, bexarotene, tretinoin
Arsenic trioxide
Asparaginase
Steroids for example dromostanolone propionate, megestrol acetate, nandrolone (decanoate, phenpropionate), dexamethasone
Gonadotropin releasing hormone agonists or antagonists for example abarelix, goserelin acetate, histrelin acetate, leuprolide acetate
Thalidomide, lenalidomide
Mercaptopurine, mitotane, pamidronate, pegademase, pegaspargase, rasburicase
BH3 mimetics for example ABT-737
MEK inhibitors for example PD98059, AZD6244, CI-1040
colony-stimulating factor analogs for example filgrastim, pegfilgrastim, sargramostim; erythropoietin or analogues thereof (e.g. darbepoetin alfa); interleukin 11; oprelvekin; zoledronate, zoledronic acid; fentanyl; bisphosphonate; palifermin.

As stated above, the compounds of the present invention also have therapeutic applications in sensitising tumour cells for radiotherapy and chemotherapy.

Hence the compounds of the present invention can be used as "radiosensitizer" and/or "chemosensitizer" or can be given in combination with another "radiosensitizer" and/or "chemosensitizer".

The term "radiosensitizer", as used herein, is defined as a molecule, preferably a low molecular weight molecule, administered to animals in therapeutically effective amounts to increase the sensitivity of the cells to ionizing radiation and/or to promote the treatment of diseases which are treatable with ionizing radiation.

The term "chemosensitizer", as used herein, is defined as a molecule, preferably a low molecular weight molecule, administered to animals in therapeutically effective amounts to increase the sensitivity of cells to chemotherapy and/or promote the treatment of diseases which are treatable with chemotherapeutics.

Several mechanisms for the mode of action of radiosensitizers have been suggested in the literature including: hypoxic cell radiosensitizers (e.g., 2- nitroimidazole compounds, and benzotriazine dioxide compounds) mimicking oxygen or alternatively behave like bioreductive agents under hypoxia; non-hypoxic cell radiosensitizers (e.g., halogenated pyrimidines) can be analogues of DNA bases and preferentially incorporate into the DNA of cancer cells and thereby promote the radiation-induced breaking of DNA molecules and/or prevent the normal DNA repair mechanisms; and various other potential mechanisms of action have been hypothesized for radiosensitizers in the treatment of disease.

Many cancer treatment protocols currently employ radiosensitizers in conjunction with radiation of x-rays. Examples of x-ray activated radiosensitizers include, but are not limited to, the following: metronidazole, misonidazole, desmethylmisonidazole, pimonidazole, etanidazole, nimorazole, mitomycin C, RSU 1069, SR 4233, E09, RB 6145, nicotinamide, 5-bromodeoxyuridine (BUdR), 5- iododeoxyuridine (IUdR), bromodeoxycytidine, fluorodeoxyuridine (FudR), hydroxyurea, cisplatin, and therapeutically effective analogs and derivatives of the same.

Photodynamic therapy (PDT) of cancers employs visible light as the radiation activator of the sensitizing agent. Examples of photodynamic radiosensitizers include the following, but are not limited to: hematoporphyrin derivatives, Photofrin, benzoporphyrin derivatives, tin etioporphyrin, pheoborbide-a, bacteriochlorophyll-a, naphthalocyanines, phthalocyanines, zinc phthalocyanine, and therapeutically effective analogs and derivatives of the same.

Radiosensitizers may be administered in conjunction with a therapeutically effective amount of one or more other compounds, including but not limited to: compounds which promote the incorporation of radiosensitizers to the target cells; compounds which control the flow of therapeutics, nutrients, and/or oxygen to the target cells; chemotherapeutic agents which act on the tumour with or without additional radiation; or other therapeutically effective compounds for treating cancer or other diseases.

Chemosensitizers may be administered in conjunction with a therapeutically effective amount of one or more other compounds, including but not limited to: compounds which promote the incorporation of chemosensitizers to the target cells; compounds which control the flow of therapeutics, nutrients, and/or oxygen to the target cells; chemotherapeutic agents which act on the tumour or other therapeutically effective compounds for treating cancer or other disease. Calcium antagonists, for example verapamil, are found useful in combination with antineoplastic agents to establish chemosensitivity in tumor cells resistant to accepted chemotherapeutic agents and to potentiate the efficacy of such compounds in drug-sensitive malignancies.

In view of their useful pharmacological properties, the components of the combinations according to the invention, i.e. the one or more other medicinal agent and the p53-MDM2 inhibitor according to the present invention may be formulated into various pharmaceutical forms for administration purposes. The components may be formulated separately in individual pharmaceutical compositions or in a unitary pharmaceutical composition containing all components.

The present invention therefore also relates to a pharmaceutical composition comprising the one or more other medicinal agent and the p53-MDM2 inhibitor according to the present invention together with a pharmaceutical carrier.

The present invention further relates to the use of a combination according to the invention in the manufacture of a pharmaceutical composition for inhibiting the growth of tumour cells.

The present invention further relates to a product containing as first active ingredient a p53-MDM2 inhibitor according to the invention and as further active ingredient one or more anticancer agent, as a combined preparation for simultaneous, separate or sequential use in the treatment of patients suffering from cancer.

The one or more other medicinal agents and p53-MDM2 inhibitor may be administered simultaneously (e.g. in separate or unitary compositions) or sequentially in either order. In the latter case, the two or more compounds will be administered within a period and in an amount and manner that is sufficient to ensure that an advantageous or synergistic effect is achieved. It will be appreciated that the preferred method and order of administration and the respective dosage amounts and regimes for each component of the combination will depend on the particular other medicinal agent and p53-MDM2 inhibitor being administered, their route of administration, the particular tumour being treated and the particular host being treated. The optimum method and order of administration and the dosage amounts and regime can be readily determined by those skilled in the art using conventional methods and in view of the information set out herein.

The weight ratio of the compound according to the present invention and the one or more other anticancer agent(s) when given as a combination may be determined by the person skilled in the art. Said ratio and the exact dosage and frequency of administration depends on the particular compound according to the invention and the other anticancer agent(s) used, the particular condition being treated, the severity of the condition being treated, the age, weight, gender, diet, time of administration and general physical condition of the particular patient, the mode of administration as well as other medication the individual may be taking, as is well known to those skilled in the art. Furthermore, it is evident that the effective daily amount may be lowered or increased depending on the response of the treated subject and/or depending on the evaluation of the physician prescribing the compounds of the instant invention. A particular weight ratio for the present compound of formula (I) and another anticancer agent may range from 1/10 to 10/1, more in particular from 1/5 to 5/1, even more in particular from 1/3 to 3/1.

The platinum coordination compound is advantageously administered in a dosage of 1 to 500 mg per square meter ($mg/m^2$) of body surface area, for example 50 to 400 $mg/m^2$, particularly for cisplatin in a dosage of about 75 $mg/m^2$ and for carboplatin in about 300 $mg/m^2$ per course of treatment.

The taxane compound is advantageously administered in a dosage of 50 to 400 mg per square meter ($mg/m^2$) of body surface area, for example 75 to 250 $mg/m^2$, particularly for paclitaxel in a dosage of about 175 to 250 $mg/m^2$ and for docetaxel in about 75 to 150 $mg/m^2$ per course of treatment.

The camptothecin compound is advantageously administered in a dosage of 0.1 to 400 mg per square meter ($mg/m^2$) of body surface area, for example 1 to 300 $mg/m^2$, particularly for irinotecan in a dosage of about 100 to 350 $mg/m^2$ and for topotecan in about 1 to 2 $mg/m^2$ per course of treatment.

The anti-tumour podophyllotoxin derivative is advantageously administered in a dosage of 30 to 300 mg per square meter ($mg/m^2$) of body surface area, for example 50 to 250 $mg/m^2$, particularly for etoposide in a dosage of about 35 to 100 $mg/m^2$ and for teniposide in about 50 to 250 $mg/m^2$ per course of treatment.

The anti-tumour vinca alkaloid is advantageously administered in a dosage of 2 to 30 mg per square meter ($mg/m^2$) of body surface area, particularly for vinblastine in a dosage of about 3 to 12 $mg/m^2$, for vincristine in a dosage of about 1 to 2 $mg/m^2$, and for vinorelbine in dosage of about 10 to 30 $mg/m^2$ per course of treatment.

The anti-tumour nucleoside derivative is advantageously administered in a dosage of 200 to 2500 mg per square meter ($mg/m^2$) of body surface area, for example 700 to 1500 $mg/m^2$, particularly for 5-FU in a dosage of 200 to 500 $mg/m^2$, for gemcitabine in a dosage of about 800 to 1200 $mg/m^2$ and for capecitabine in about 1000 to 2500 $mg/m^2$ per course of treatment.

The alkylating agents such as nitrogen mustard or nitrosourea is advantageously administered in a dosage of 100 to 500 mg per square meter ($mg/m^2$) of body surface area, for example 120 to 200 $mg/m^2$, particularly for cyclophosphamide in a dosage of about 100 to 500 $mg/m^2$, for chlorambucil in a dosage of about 0.1 to 0.2 mg/kg, for carmustine in a dosage of about 150 to 200 $mg/m^2$, and for lomustine in a dosage of about 100 to 150 $mg/m^2$ per course of treatment.

The anti-tumour anthracycline derivative is advantageously administered in a dosage of 10 to 75 mg per square meter ($mg/m^2$) of body surface area, for example 15 to 60 $mg/m^2$, particularly for doxorubicin in a dosage of about 40 to 75 $mg/m^2$, for daunorubicin in a dosage of about 25 to 45 $mg/m^2$, and for idarubicin in a dosage of about 10 to 15 $mg/m^2$ per course of treatment.

The antiestrogen agent is advantageously administered in a dosage of about 1 to 100 mg daily depending on the particular agent and the condition being treated. Tamoxifen is advantageously administered orally in a dosage of 5 to 50 mg, preferably 10 to 20 mg twice a day, continuing the therapy for sufficient time to achieve and maintain a therapeutic effect. Toremifene is advantageously administered orally in a dosage of about 60 mg once a day, continuing the therapy for sufficient time to achieve and maintain a therapeutic effect. Anastrozole is advantageously administered orally in a dosage of about 1 mg once a day. Droloxifene is advantageously administered orally in a dosage of about 20-100 mg once a day. Raloxifene is advantageously administered orally in a dosage of about 60 mg once a day. Exemestane is advantageously administered orally in a dosage of about 25 mg once a day.

Antibodies are advantageously administered in a dosage of about 1 to 5 mg per square meter ($mg/m^2$) of body surface area, or as known in the art, if different. Trastuzumab is advantageously administered in a dosage of 1 to 5 mg per square meter ($mg/m^2$) of body surface area, particularly 2 to 4 $mg/m^2$ per course of treatment.

These dosages may be administered for example once, twice or more per course of treatment, which may be repeated for example every 7, 14, 21 or 28 days.

The compounds of formula (I), the pharmaceutically acceptable acid addition salts and stereoisomeric forms thereof can have valuable diagnostic properties in that they can be used for detecting or identifying a p53-MDM2 interaction in a biological sample comprising detecting or measuring the formation of a complex between a labelled compound and/or p53 and/or MDM2 and or other molecules, peptides, proteins, enzymes or receptors.

The detecting or identifying methods can use compounds that are labelled with labelling agents such as radioisotopes, enzymes, fluorescent substances, luminous substances, etc. Examples of the radioisotopes include $^{125}I$, $^{131}I$, $^{3}H$ and $^{14}C$. Enzymes are usually made detectable by conjugation of an appropriate substrate which, in turn catalyses a detectable reaction. Examples thereof include, for example, beta-galactosidase, beta-glucosidase, alkaline phosphatase, peroxidase and malate dehydrogenase, preferably horseradish peroxidase. The luminous substances include, for example, luminol, luminol derivatives, luciferin, aequorin and luciferase.

Biological samples can be defined as body tissue or body fluids. Examples of body fluids are cerebrospinal fluid, blood, plasma, serum, urine, sputum, saliva and the like.

The following examples illustrate the present invention.

EXPERIMENTAL PART

Hereinafter, the term 'DIPEA' means N-ethyl-N-(1-methylethyl)-2-propanamine, '$K_2CO_3$' means potassium carbonate, '$CH_2Cl_2$' means dichloromethane, '$CH_3OH$' means methanol, '$MgSO_4$' means magnesium sulphate, '$NaHCO_3$' means carbonic acid monosodium salt, 'DMSO' means dimethylsulfoxide, 'M.P.' means melting point, '$CH_3CN$' means acetonitrile, 'EtOAc' means ethyl acetate, 'DIPE' means diisopropyl ether, 'DMF' means N,N-dimethylformamide, 'THF' means tetrahydrofuran, '$V_2O_5$' means vanadium oxide, '$NaBH_4$' means sodium tetrahydroborate (-1), 'NaCl' means sodium chloride, 'EtOH' means ethanol, '$NH_4OH$' means ammonium hydroxide. Column chromatography over Sunfire means reversed-phase HPLC using C18-bonded silica stationary phase columns Sunfire™ from Waters Corp. (Milford, Mass.)

A. Preparation of the Intermediates

Example A1 a) Preparation of Intermediate 1

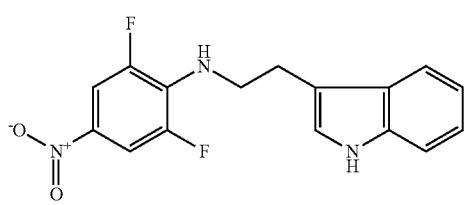

A mixture of 1,2,3-trifluoro-5-nitrobenzene (0.0037 mol), 1H-indole-3-ethanamine (0.0037 mol) and DIPEA (0.0189 mol) was stirred at 120° C. for 18 hours, then cooled to room temperature, poured out into $K_2CO_3$ 10% aqueous solution and extracted with $CH_2Cl_2/CH_3OH$ (few). The organic layer was separated, dried ($MgSO_4$), filtered and the solvent was evaporated till dryness, yielding 1.3 g (>100%) of intermediate 1.

b) Preparation of Intermediate 2

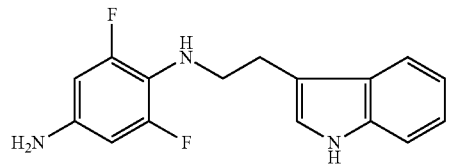 [SMILES: Nc1cc(F)c(NCCc2c[nH]c3ccccc23)c(F)c1]

A mixture of intermediate 1 (0.0037 mol) and Pd/C 10% (0.13 g) in toluene (50 ml) was hydrogenated at room temperature for 3 days under atmospheric pressure, then filtered over celite. The filtrate was evaporated till dryness. The residue was taken up in $CH_2Cl_2$. The organic layer was separated, dried ($MgSO_4$), filtered and the solvent was evaporated till dryness, yielding 1.2 g (>100%) of intermediate 2.

Example A2 a) Preparation of Intermediate 3

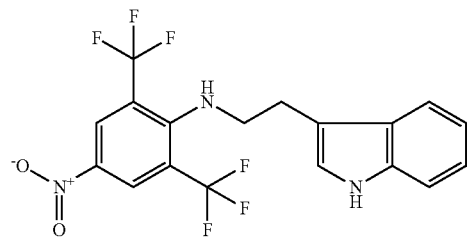

A mixture of 2-chloro-5-nitro-1,3-bis(trifluoromethyl) benzene (0.002 mol), 1H-indole-3-ethanamine (0.0024 mol) and $NaHCO_3$ (0.0026 mol) in DMSO (4 ml) was stirred at 100° C. for 48 hours, then cooled to room temperature and poured out into $H_2O$. The precipitate was filtered, washed with diethyl ether and dried, yielding 0.41 g (49%) of intermediate 3 (M.P.: 152° C.).

b) Preparation of Intermediate 4

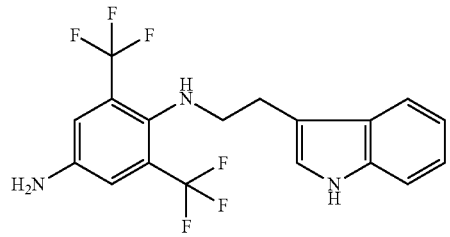 [SMILES: Nc1cc(C(F)(F)F)c(NCCc2c[nH]c3ccccc23)c(C(F)(F)F)c1]

A mixture of intermediate 3 (0.0008 mol) and Raney Nickel (0.36 g) in $CH_3OH$ (10 ml) was hydrogenated at room temperature for 18 hours under atmospheric pressure, then filtered over celite. The filtrate was evaporated till dryness. The residue was dissolved in CH$_2$Cl$_2$. The organic layer was separated, dried (MgSO$_4$), filtered and the solvent was evaporated till dryness, yielding 0.32 g (96%) of intermediate 4.

Example A3 a) Preparation of Intermediate 5a

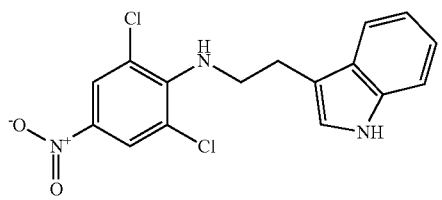

A mixture of 1,3-dichloro-2-fluoro-5-nitrobenzene (0.0048 mol), 1H-indole-3-ethanamine (0.0048 mol) and NaHCO$_3$ (0.0057 mol) in DMSO (10 ml) was stirred at 60° C. overnight, cooled to room temperature. Ice water was added. The mixture was extracted with EtOAc. The organic layer was decanted, dried (MgSO$_4$), filtered off and the solvent was evaporated till dryness. The residue was crystallized from CH$_3$CN/DIPE. The precipitate was filtered off and dried, yielding 1.03 g (62%) of intermediate 5a (M.P.: 98° C.).

b) Preparation of Intermediate 6a

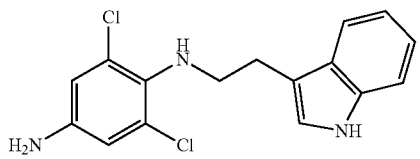 [SMILES: Nc1cc(Cl)c(NCCc2c[nH]c3ccccc23)c(Cl)c1]

A mixture of intermediate 5a (0.0027 mol) and Pt/C 5% (0.1 g) in V$_2$O$_5$ (0.01 g), a 4% thiophene solution in DIPE (0.1 ml) and THF (20 ml) was hydrogenated at room temperature for 18 hours under atmospheric pressure. The catalyst was removed by filtration. The filtrate was evaporated till dryness, yielding 0.91 g (100%) of intermediate 6a.

c) Preparation of Intermediate 5b

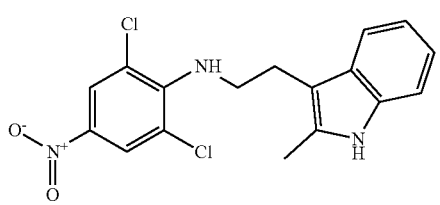 [SMILES: Cc1[nH]c2ccccc2c1CCNc1c(Cl)cc([N+](=O)[O-])cc1Cl]

A mixture of 1,3-dichloro-2-fluoro-5-nitrobenzene (0.0048 mol), 1H-indole-2-methyl-3-ethanamine (0.004 mol) and NaHCO$_3$ (0.0048 mol) in DMSO (10 ml) was stirred at 60° C. overnight, cooled to room temperature. Ice water was added. The precipitate was filtered, washed with CH$_3$CN and dried, yielding 0.48 g (28%) of intermediate 5b (M.P.: 147° C.).

d) Preparation of Intermediate 6b

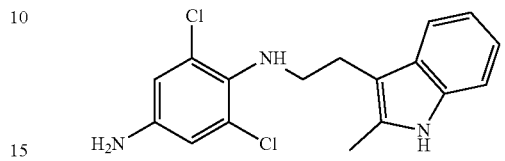

A mixture of intermediate 5b (0.0013 mol) and Pt/C 5% (0.05 g) in V$_2$O$_5$ (0.005 g), a 4% thiophene solution in DIPE (0.05 ml) and THF (10 ml) was hydrogenated at room temperature for 18 hours under atmospheric pressure, then filtered. The filtrate was evaporated till dryness, yielding 0.48 g (100%) of intermediate 6b.

e) Preparation of Intermediate 5c

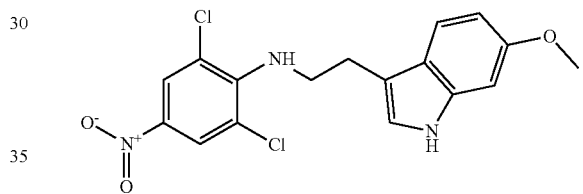

A mixture of 1,3-dichloro-2-fluoro-5-nitrobenzene (0.0048 mol), 1H-indole-6-methoxy-3-ethanamine (0.0048 mol) and NaHCO$_3$ (0.0057 mol) in DMSO (10 ml) was stirred at 60° C. overnight, cooled to room temperature. Ice water was added. The precipitate was filtered, washed with CH$_3$CN and the solvent was evaporated till dryness, yielding 1.2 g (66%) of intermediate 5c (M.P.: 116° C.).

f) Preparation of Intermediate 6c

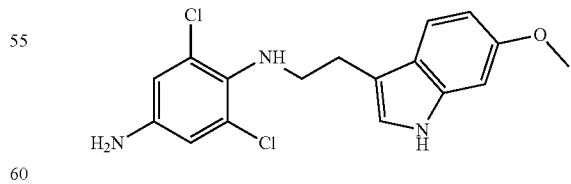

A mixture of intermediate 5c (0.0031 mol) and Pt/C 5% (0.12 g) in V$_2$O$_5$ (0.012 g), a 4% thiophene solution in DIPE (0.12 ml) and THF (25 ml) was hydrogenated at room temperature for 18 hours under atmospheric pressure, then filtered over celite. The filtrate was evaporated till dryness, yielding 1.2 g (100%) of intermediate 6c.

Example A4 a) Preparation of Intermediate 7a

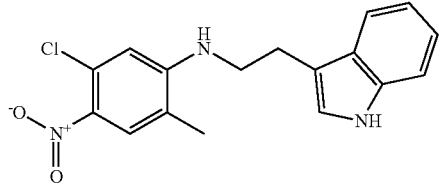

A mixture of 1-chloro-5-fluoro-4-methyl-2-nitrobenzene (0.0026 mol), 1H-indole-3-ethanamine (0.0026 mol) and NaHCO$_3$ (0.0032 mol) in DMSO (5 ml) was stirred at 60° C. overnight, cooled to room temperature. Ice water was added. The precipitate was filtered off, washed with CH$_3$CN and dried, yielding 0.54 g (62%) of intermediate 7a (M.P.: 146° C.).

b) Preparation of Intermediate 8a

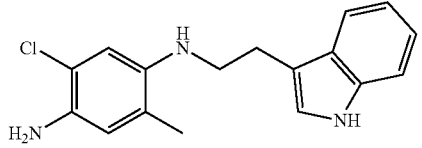

A mixture of intermediate 7a (0.0012 mol) and Pt/C 5% (0.049 g) in V$_2$O$_5$ (0.005 g), a 4% thiophene solution in DIPE (0.049 ml) and THF (10 ml) was hydrogenated at room temperature for 18 hours under atmospheric pressure. The catalyst was removed by filtration. The filtrate was evaporated till dryness, yielding 0.36 g (100%) of intermediate 8a.

c) Preparation of Intermediate 7b

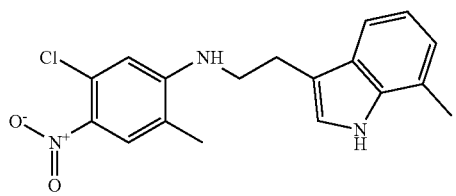 [SMILES: Cc1cc([N+](=O)[O-])c(Cl)cc1NCCc1c[nH]c2c(C)cccc12]

A mixture of 1-chloro-5-fluoro-4-methyl-2-nitrobenzene (0.0026 mol), 1H-indole-7-methyl-3-ethanamine (0.0026 mol), NaHCO$_3$ (0.0032 mol) in DMSO (5 ml) was stirred at 60° C. overnight, cooled to room temperature. Ice water was added. The precipitate was filtered off, washed with CH$_3$CN and the solvent was evaporated till dryness, yielding 0.53 g (58%) of intermediate 7b (M.P.: 171° C.).

d) Preparation of Intermediate 8b

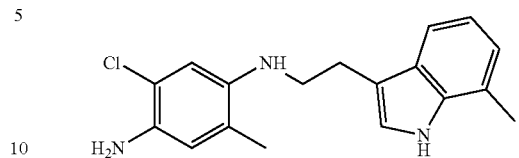

A mixture of intermediate 7b (0.0014 mol) and Pt/C 5% (0.05 g) in V$_2$O$_5$ (0.005 g), a 4% thiophene solution in DIPE (0.05 ml) and THF (15 ml) was hydrogenated at room temperature for 18 hours under atmospheric pressure, then filtered over celite. The filtrate was evaporated till dryness, yielding 0.49 g (100%) of intermediate 8b.

Example A5 a) Preparation of Intermediate 9

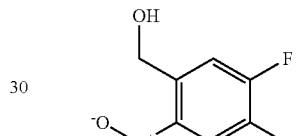

NaBH$_4$ (0.024 mol) was added portionwise at 5° C. to a solution of 4-bromo-5-fluoro-2-nitrobenzaldehyde (0.02 mol) in CH$_3$OH (50 ml). The mixture was stirred at room temperature for 2 hours. Saturated NaCl aqueous solution was added. The mixture was extracted with CH$_2$Cl$_2$. The organic layer was separated, dried (MgSO$_4$), filtered and the solvent was evaporated till dryness, yielding 5 g (100%) of intermediate 9.

b) Preparation of Intermediate 10

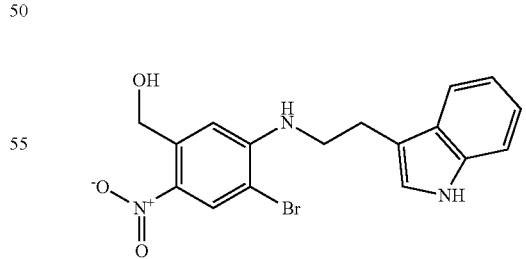

A mixture of intermediate 9 (0.01 mol), 1H-indole-3-ethanamine (0.01 mol) and NaHCO$_3$ (0.012 mol) in DMSO (25 ml) was stirred at 60° C. overnight, then cooled to room temperature. Ice and water were added. The precipitate was filtered off, washed with CH$_3$CN and dried, yielding 1.77 g (45%) of intermediate 10.

c) Preparation of Intermediate 11

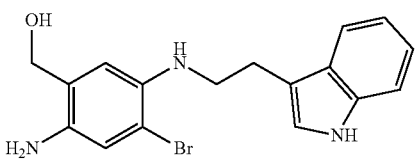 [SMILES: Nc1cc(Br)c(NCCc2c[nH]c3ccccc23)cc1CO]

A mixture of intermediate 10 (0.0045 mol), Pt/C 5% (0.18 g) and V$_2$O$_5$ (0.02 g) in a 4% thiophene solution (0.18 ml) and THF (50 ml) was hydrogenated at room temperature for 48 hours under atmospheric pressure, then filtered over celite. The filtrate was evaporated till dryness, yielding 1.7 g (100%) of intermediate 11.

Example A6 a) Preparation of Intermediate 12

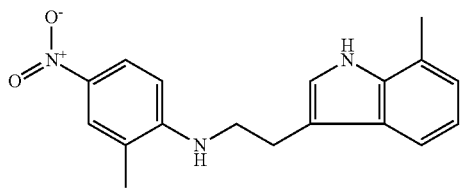 [SMILES: Cc1cc([N+](=O)[O-])ccc1NCCc1c[nH]c2c(C)cccc12]

A mixture of 1-fluoro-2-methyl-4-nitrobenzene (0.0103 mol), 7-methyl-1H-indole-3-ethanamine (0.0103 mol) and DIPEA (0.0515 mol) was stirred at 120° C. for 18 hours, then cooled to room temperature, diluted in CH$_2$Cl$_2$/CH$_3$OH (few) and washed with K$_2$CO$_3$ 10% aqueous solution. The organic layer was separated, dried (MgSO$_4$), filtered and the solvent was evaporated till dryness. The residue (4.1 g) was purified by column chromatography over silica gel (eluent: CH$_2$Cl$_2$/cyclohexane 70/30; 15-35 μm). The pure fractions were collected and the solvent was evaporated, yielding 1.45 g (45%) of intermediate 12.

b) Preparation of Intermediate 13

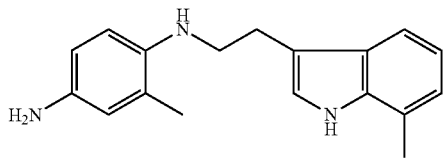 [SMILES: Cc1cc(N)ccc1NCCc1c[nH]c2c(C)cccc12]

A mixture of intermediate 12 (0.0045 mol) and Pt/C 5% (0.15 g) in toluene (40 ml) was hydrogenated at room temperature for 18 hours under a 3 bar pressure, then filtered. The filtrate was evaporated till dryness, yielding 1.25 g (100%) of intermediate 13.

c) Preparation of Intermediate 14

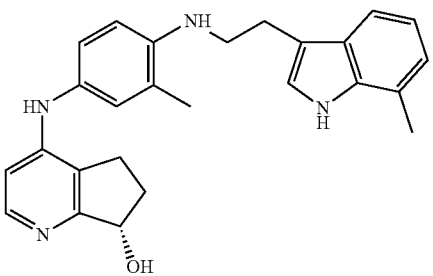 [SMILES: Cc1cc(Nc2ccnc3c2CC[C@@H]3O)ccc1NCCc1c[nH]c2c(C)cccc12]

A solution of intermediate 13 (0.04 mol), (7S)-4-chloro-6,7-dihydro-5H-cyclopenta[b]pyridin-7-ol (0.0044 mol), HCl/dioxane 4M (2 ml) in CH$_3$CN/EtOH (150 ml) was stirred at 65° C. for a weekend. K$_2$CO$_3$ 10% aqueous solution and EtOAc were added. The mixture was extracted. The organic layer was separated, dried (MgSO$_4$), filtered off and the solvent was evaporated. The residue (23 g) was purified by column chromatography (eluent: CH$_2$Cl$_2$/CH$_3$OH/NH$_4$OH 93/7/1). The pure fractions were collected and the solvent was evaporated. The residue (14.2 g, 85%) was crystallized from CH$_3$CN. The precipitate was filtered off and dried, yielding 10.4 g (63%) of intermediate 14.

Example A7 a) Preparation of Intermediate 15

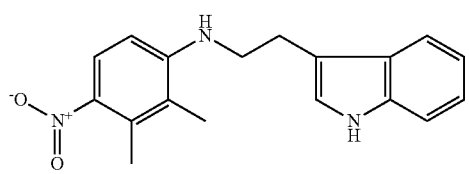

A mixture of 1-fluoro-2,3-dimethyl-4-nitrobenzene (0.003 mol), 1H-indole-3-ethanamine (0.0036 mol) and NaHCO$_3$ (0.0039 mol) in DMSO (4 ml) was stirred at 100° C. for 3 days, then cooled to room temperature. H$_2$O was added. The precipitate was filtered, washed with EtOH, then with diethyl ether and dried. A part of this fraction was dried at 60° C. for 18 hours under vacuo, yielding 0.052 g of intermediate 15 (M.P.: 178° C.).

b) Preparation of Intermediate 16

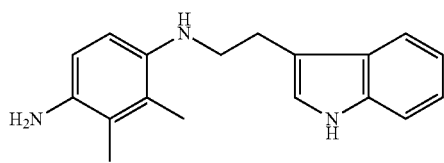 [SMILES: Cc1c(N)ccc(NCCc2c[nH]c3ccccc23)c1C]

A mixture of intermediate 15 (0.0022 mol) and Raney Nickel (0.7 g) in CH$_3$OH/THF (90/10) (20 ml) was hydrogenated at room temperature for 3 hours under atmospheric pressure, then filtered over celite. The filtrate was evaporated till dryness. The residue was taken up in diethyl ether. The organic layer was separated, dried (MgSO₄), filtered and the solvent was evaporated till dryness, yielding 0.64 g (100%) of intermediate 16 (M.P.: 161° C.).

Example A8 a) Preparation of Intermediate 17

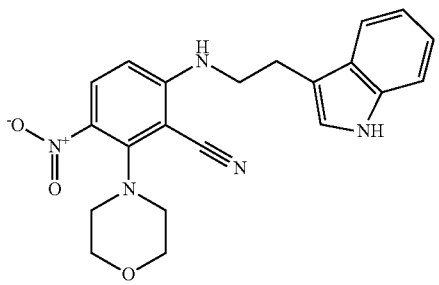

A mixture of 6-fluoro-2-(4-morpholinyl)-3-nitrobenzonitrile (0.002 mol), 1H-indole-3-ethanamine (0.002 mol) and NaHCO₃ (0.0024 mol) in DMSO (5 ml) was stirred at 60° C. overnight, cooled to room temperature. Ice water was added. The precipitate was filtered off, washed with CH₃CN and dried, yielding 0.64 g (82%) of intermediate 17 (M.P.: 205° C.).

b) Preparation of Intermediate 18

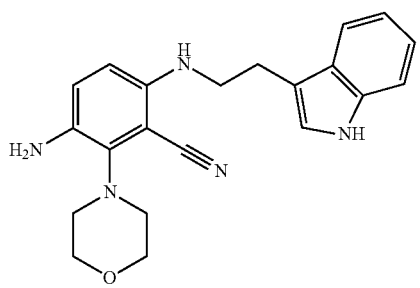 [SMILES: N#Cc1c(NCCc2c[nH]c3ccccc23)ccc(N)c1N1CCOCC1]

A mixture of intermediate 17 (0.0015 mol) and Pt/C 5% (0.06 g) in V₂O₅ (0.01 g), a 4% thiophene solution in DIPE (0.06 ml) and THF (15 ml) was hydrogenated at room temperature for 18 hours under atmospheric pressure. The catalyst was removed by filtration. The filtrate was evaporated till dryness, yielding 0.61 g (100%) of intermediate 18.

Example A9 a) Preparation of Intermediate 19

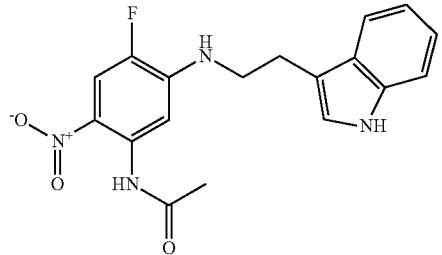

A mixture of N-(4,5-difluoro-2-nitrophenyl)-acetamide (0.0023 mol), 1H-indole-3-ethanamine (0.0023 mol) and NaHCO₃ (0.0028 mol) in DMSO (5 ml) was stirred at 60° C. overnight, then cooled to room temperature. Ice and water were added. The precipitate was filtered off and dried, yielding 0.73 g (88%) of intermediate 19 (M.P.: 166° C.).

b) Preparation of Intermediate 20

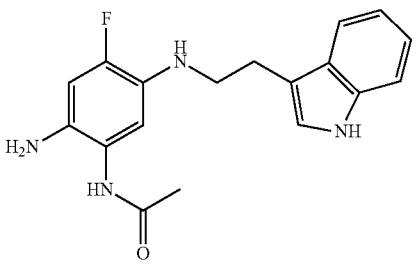 [SMILES: CC(=O)Nc1cc(NCCc2c[nH]c3ccccc23)c(F)cc1N]

A mixture of intermediate 19 (0.002 mol) and Raney Nickel (0.8 g) in CH₃OH (15 ml) was hydrogenated at room temperature for 4 hours under atmospheric pressure, then filtered over celite. The filtrate was evaporated till dryness. The residue was dissolved in CH₂Cl₂. The organic layer was separated, dried (MgSO₄), filtered and the solvent was evaporated till dryness, yielding 0.68 g (100%) of intermediate 20.

Example A10 a) Preparation of Intermediate 21

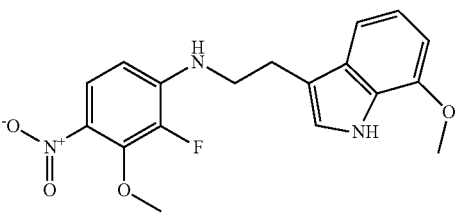

A mixture of 1,2-difluoro-3-methoxy-4-nitrobenzene (0.0074 mol), 7-methoxy-1H-indole-3-ethanamine (0.0074 mol) and NaHCO₃ (0.0088 mol) in DMSO (15 ml) was stirred at 60° C. overnight, then cooled to room temperature. Ice and water were added. The precipitate was filtered, washed with CH₃CN and dried, yielding 2.27 g (85%) of intermediate 21 (M.P.: 164° C.).

b) Preparation of Intermediate 22

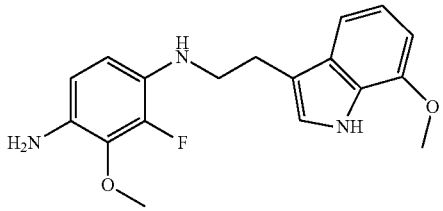 [SMILES: COc1c(N)ccc(NCCc2c[nH]c3c(OC)cccc23)c1F]

A mixture of intermediate 21 (0.0058 mol), Pt/C 5% (0.21 g) and V₂O₅ (0.021 g) in a 4% thiophene solution in DIPE (0.21 ml) and THF (30 ml) was hydrogenated at room temperature for 48 hours under atmospheric pressure, then filtered over celite. The filtrate was evaporated till dryness, yielding 2.1 g (100%) of intermediate 22.

Example A11

Intermediate compounds which comprise further substituent(s) on the 1H-indol-3-yl ring may be prepared analogously to the above reactions, employing a further-substituted 1H-indole-3-ethanamine, e.g., 2-methyl-1H-indole-3-ethanamine, 7-methyl-1H-indole-3-ethanamine, 6-methoxy-1H-indole-3-ethanamine, or 7-methoxy-1H-indole-3-ethanamine.

Example A12 a) Preparation of Intermediate 23

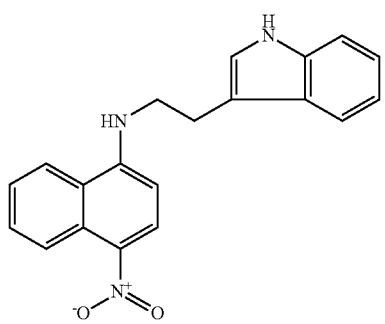

A mixture of 1-methoxy-4-nitro-naphthalene (0.0005 mol) and 1H-indole-3-ethanamine (0.0005 mol) in EtOH (3 ml) was stirred at 100° C. for 18 hours, then evaporated till dryness. The residue (0.4 g) was purified by column chromatography over silica gel (eluent: CH₂Cl₂ 100). The pure fractions were collected and the solvent was evaporated, yielding 0.03 g (10%) of intermediate 23 (melting point: 211° C.).

b) Preparation of Intermediate 24

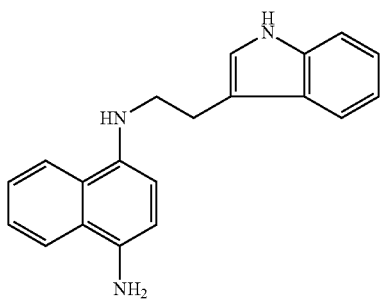 [SMILES: Nc1ccc(NCCc2c[nH]c3ccccc23)c2ccccc12]

A mixture of intermediate 23 (0.002 mol) and Raney Nickel (0.7 g) in EtOH (50 ml) was hydrogenated at room temperature for 18 hours under a 3 bar pressure, then filtered. The filtrate was evaporated till dryness. The residue (0.6 g) was purified by column chromatography over kromasil (eluent: CH₂Cl₂/CH₃OH/NH₄OH 99/1/0.1 to 97/3/0.3; 5 μm). The pure fractions were collected and the solvent was evaporated, yielding 0.32 g (53%) of intermediate 24 (melting point: 148° C.).

Example A13 a) Preparation of Intermediate 25

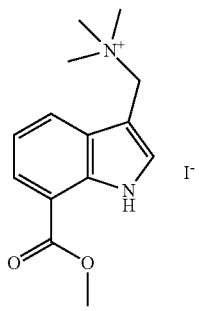 [SMILES: COC(=O)c1cccc2c(C[N+](C)(C)C)c[nH]c12 ; [I-]]

Methyl iodide (0.0215 mol) was added dropwise in a solution of 3-[(dimethylamino)methyl]-1H-Indole-7-carboxylic acid, methyl ester (0.0215 mol) in EtOH (50 ml). The mixture was stirred at room temperature for 24 hours. The precipitate was filtered off and washed with EtOH, yielding 7.5 g of intermediate 25.

This product was used directly in the next reaction step.

b) Preparation of Intermediate 26

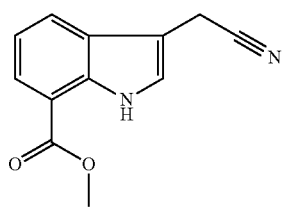 [SMILES: COC(=O)c1cccc2c(CC#N)c[nH]c12]

A mixture of intermediate 25 (0.02 mol) and sodium cyanide (0.026 mol) in DMF (75 ml) was stirred at 100° C. for 2 hours. Water was added. The precipitate was filtered off, yielding 2.2 g of intermediate 26.

This product was used directly in the next reaction step.

c) Preparation of Intermediate 27

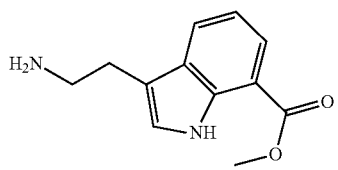 [SMILES: COC(=O)c1cccc2c(CCN)c[nH]c12]

Raney Nickel (37.485 mmol) was added to a solution of intermediate 26 and ammonia (7M, 25 ml) under nitrogen. The mixture was hydrogenated under 3 bars at room temperature for 5 hours. The crude was filtered over celite and the solvent was evaporated, yielding 2.2 g of intermediate 27.

d) Preparation of Intermediate 28

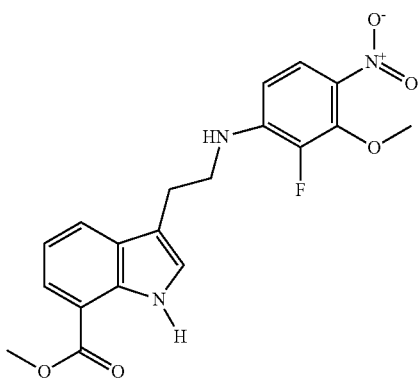 [SMILES: COC(=O)c1cccc2c(CCNc3ccc([N+](=O)[O-])c(OC)c3F)c[nH]c12]

A mixture of intermediate 27 (0.00504 mol), 2,3 difluoro-6-nitroanisole (0.00504 mol) and sodium hydrogencarbonate (0.00605 mol) in DMSO (110 ml) was heated at 60° C. overnight. The mixture was cooled to room temperature, then ice-water was added and the precipitate was filtered off, washed with CH₃CN and dried, yielding 0.860 g of intermediate 28.

e) Preparation of Intermediate 29

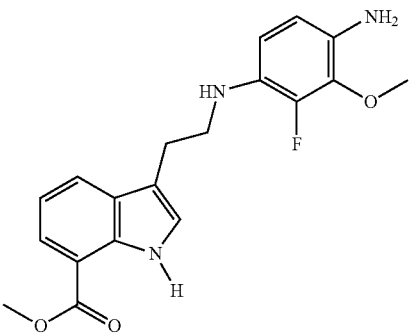

A mixture of intermediate 28 (0.0022 mol) and Raney Nickel (0.0147 mol) in CH₃OH (25 ml) was hydrogenated at room temperature under atmospheric pressure of H₂ for a week-end. The catalyst was removed by filtration and the filtrate was evaporated to dryness. The residue was dissolved with CH₂Cl₂, the organic layer was dried over MgSO₄, filtered and evaporated to dryness, yielding 0.6 g of intermediate 29.

This product was used directly in the next reaction step.

f) Preparation of Intermediate 30

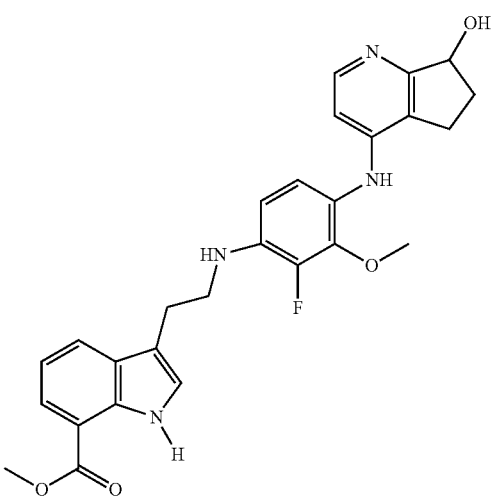 [SMILES: COC(=O)c1cccc2c(CCNc3ccc(Nc4ccnc5c4CCC5O)c(OC)c3F)c[nH]c12]

A mixture of intermediate 29 (0.00168 mol), 4-chloro-6,7-dihydro-5H-cyclopenta[b]pyridin-7-ol (0.00168 mol) and hydrogen chloride in dioxane 4M (0.000336 mol) in a solution of CH₃CN/EtOH (25 ml) was prepared. The mixture was stirred at 65° C. overnight. K₂CO₃ 10% aqueous solution was added and the organic layer was extracted with CH₂Cl₂, dried (MgSO₄), filtered and the solvent was evaporated. The residue (0.9 g) was purified by column chromatography over silica gel (eluent:CH₂Cl₂/CH₃OH/NH₄OH gradient 97/3/0.5; 90 g 15-40 μm). The pure fractions were collected and the solvent was evaporated. The residue was crystallized in CH₃OH, yielding 0.160 g of intermediate 30.

Example A14 a) Preparation of Intermediate 31

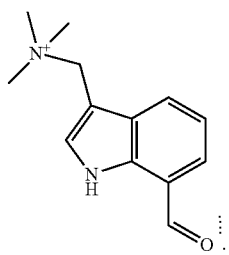 [SMILES: C[N+](C)(C)Cc1c[nH]c2c(C=O)cccc12]

3-[(dimethylamino)methyl]-1H-Indole-7-carboxaldehyde (0.13 mol), iodomethane (0.14 mol) in EtOH (300 ml) were stirred at room temperature for 2 days. The precipitate was filtered off and dried, yielding 47 g of intermediate 31.

b) Preparation of Intermediate 32

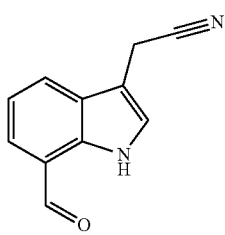 [SMILES: N#CCc1c[nH]c2c(C=O)cccc12]

Intermediate 31 (136.5 mmol), sodium cyanide (177.5 mmol) in DMF (400 ml) were stirred at room temperature for 2 hours. Water was added, the reaction mixture was extracted with EtOAc. The organic layer was separated, dried over MgSO$_4$, filtered and evaporated. The residue was purified by high-performance liquid chromatography (Irregular SiOH 20-45 μm 1000 g MATREX/Mobile phase: cyclohexane 70% ETOAc 30%). The pure fractions were collected and the solvent was evaporated, yielding 11.8 g of intermediate 32.

c) Preparation of Intermediate 33

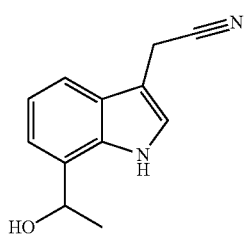

Methylmagnesium chloride (0.07 mol) was added dropwise to a solution of intermediate 32 (0.022 mol) in THF (50 ml). NH$_4$Cl 10% aqueous solution and EtOAc were added. The reaction mixture was extracted, the organic layer was separated, dried over MgSO$_4$, filtered and evaporated. The residue (2.9 g) was purified by high-performance liquid chromatography (Irregular SiOH 20-45 μm 450 g MATREX/Mobile phase:cyclohexane 60% EtOAc 40%). The pure fractions were collected and the solvent was evaporated, yielding 2 g of intermediate 33.

d) Preparation of Intermediate 34

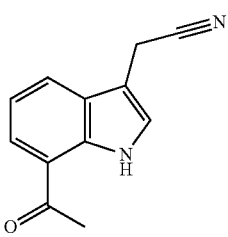

Dess-Martin periodinane (24.9 ml) was added dropwise at room temperature to a solution of intermediate 33 (10 mmol) in CH$_2$Cl$_2$ (20 ml). The reaction mixture was stirred at room temperature for 1 hour, then poured out into ice water, filtered over celite and the filtrate was extracted with CH$_2$Cl$_2$. The organic layer was separated, dried over MgSO$_4$, filtered and the solvent was evaporated. The residue (2.8 g) was purified by column chromatography over silica gel (eluent: 60/40 cyclohexane/EtOAc). The pure fractions were collected and the solvent was evaporated, yielding 0.8 g of intermediate 34.

e) Preparation of Intermediate 35

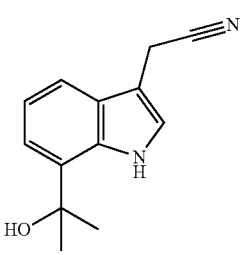 [SMILES: CC(C)(O)c1cccc2c(CC#N)c[nH]c12]

Methylmagnesium chloride (12.9 mmol) was added dropwise to a solution of intermediate 34 (4 mmol) in THF (15 ml) at 5° C. under N$_2$. The reaction mixture was stirred at room temperature for 30 minutes. NH$_4$Cl 10% aqueous solution was added carefully at 5° C. EtOAc was added and the reaction mixture was extracted. The organic layer was separated, dried over MgSO$_4$, filtered and evaporated. The residue (1.3 g) was purified by column chromatography (eluent: 70/30 cyclohexane/EtOAc). The pure fractions were collected and the solvent was evaporated, yielding 0.8 g of intermediate 35.

f) Preparation of Intermediate 36

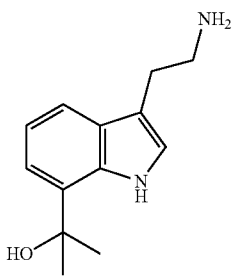 [SMILES: CC(C)(O)c1cccc2c(CCN)c[nH]c12]

A mixture of intermediate 35 (2.8 mmol), Raney Nickel (0.6 g) in CH$_3$OH/NH$_3$ (10 ml) was hydrogenated under a 3 bar pressure at room temperature for 2 hours. The residue was filtered over celite, washed with CH$_2$Cl$_2$ and the solvent was evaporated, yielding 0.7 g of intermediate 36.

g) Preparation of Intermediate 37

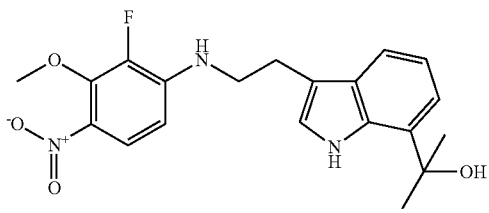

A mixture of intermediate 36 (1.60 mmol), 2,3-difluoro-6-nitroanisole (1.76 mmol), carbonic acid sodium salt (1.92 mmol) in DMSO (5 ml) was heated at 60° C. overnight. The mixture was cooled to room temperature. Ice water was added, CH$_2$Cl$_2$ was added. The reaction mixture was extracted, the organic layer was separated, dried over MgSO$_4$, filtered and concentrated.

The residue (0.8 g) was purified by high-performance liquid chromatography (Irregular SiOH 15-40 μm 300 g MERCK/Mobile phase:cyclohexane 70% EtOAc 30%). The pure fractions were collected and the solvent was evaporated, yielding 450 mg of intermediate 37.

h) Preparation of Intermediate 8

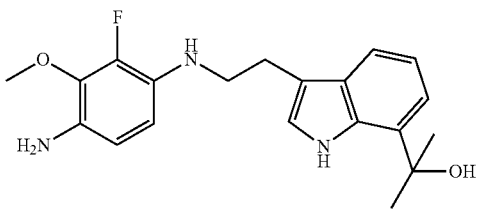 [SMILES: COc1c(N)ccc(NCCc2c[nH]c3c(C(C)(C)O)cccc23)c1F]

Intermediate 37 (1.03 mmol), Pt/C 5% (0.1 g), V$_2$O$_5$ (5 mg), thiophene solution 4% in DIPE (30 μL) in THF (20 ml) were hydrogenated at atmospheric pressure for 1 night at room temperature. The reaction mixture was filtered over celite, washed with CH$_2$Cl$_2$ and the filtrate was evaporated, yielding 0.33 g of intermediate 38.

B. Preparation of the Final Compounds

Example B1

Preparation of Compound 11

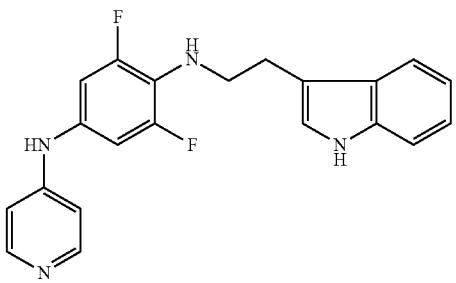 [SMILES: Fc1cc(Nc2ccncc2)cc(F)c1NCCc1c[nH]c2ccccc12]

A mixture of intermediate 2 (0.0012 mol), 4-bromopyridine, hydrochloride (1:1) (0.0012 mol) and DIPEA (0.001 mol) in CH$_3$CN (10 ml) was stirred at 65° C. for 18 hours, then cooled to room temperature, poured out into K$_2$CO$_3$ 10% aqueous solution and extracted with CH$_2$Cl$_2$/CH$_3$OH (few). The organic layer was separated, dried (MgSO$_4$), filtered and the solvent was evaporated till dryness. The residue (0.47 g) was purified by column chromatography over kromasil (eluent: CH$_2$Cl$_2$/CH$_3$OH/NH$_4$OH 97/3/0.3 to 91/9/0.9; 3.5 μm). The pure fractions were collected and the solvent was evaporated. The residue was crystallized from CH$_3$CN. The precipitate was filtered off and dried, yielding 0.163 g (36%) of compound 11 (M.P.: 164° C.).

Compounds No. 12, 13 and 65 were made according to example B1.

Example B2 a) Preparation of Compound 3

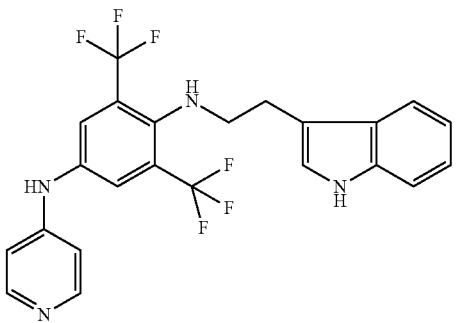 [SMILES: FC(F)(F)c1cc(Nc2ccncc2)cc(C(F)(F)F)c1NCCc1c[nH]c2ccccc12]

A mixture of intermediate 4 (0.0002 mol), 4-bromopyridine, hydrochloride (1:1) (0.0002 mol) and DIPEA (0.0002 mol) in CH$_3$CN (1 ml) and EtOH (0.5 ml) was stirred at 65° C. for 18 hours. HCl (0.2 eq) and dioxane 4N (14 μl) were added. The mixture was stirred at 65° C. for 18 hours, then cooled to room temperature, diluted in CH$_2$Cl$_2$ and washed with K$_2$CO$_3$ 10% aqueous solution. The organic layer was separated, dried (MgSO$_4$), filtered and the solvent was evaporated till dryness. The residue (0.24 g) was purified by column chromatography over Sunfire (eluent: CH$_2$Cl$_2$/CH$_3$OH/NH$_4$OH 100/0/0 to 93/7/0.7; 5 μm). The pure fractions were collected and the solvent was evaporated. The residue (0.073 g, 57%) was crystallized from CH₃CN. The precipitate was filtered off and dried, yielding 0.039 g (30%) of compound 3 (M.P.: 187° C.).

Compound No. 4 was made according to example B2a).

b) Preparation of Compound 5

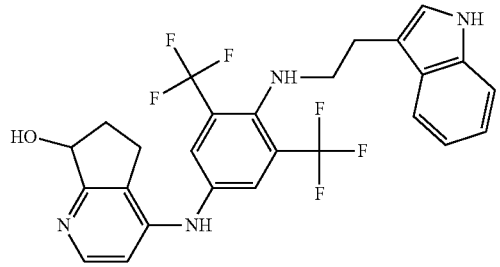 [SMILES: OC1CCc2c(Nc3cc(C(F)(F)F)c(NCCc4c[nH]c5ccccc45)c(C(F)(F)F)c3)ccnc21]

A mixture of intermediate 4 (0.0002 mol) and 4-chloro-6,7-dihydro-5H-cyclopenta[b]pyridin-7-ol (0.0002 mol) in HCl/dioxane 4N (14 µl), CH₃CN (1 ml) and EtOH (0.5 ml) was stirred at 65° C. for 18 hours. HCl (0.2 eq) and dioxane 4N (14 µl) were added. The mixture was stirred at 65° C. for 18 hours, then cooled to room temperature, diluted in CH₂Cl₂ and washed with K₂CO₃ 10% aqueous solution. The organic layer was separated, dried (MgSO₄), filtered and the solvent was evaporated till dryness. The residue (0.14 g) was purified by column chromatography over Sunfire (eluent: CH₂Cl₂/CH₃OH/NH₄OH 100/0/0 to 92/8/0.8; 5 µm). The pure fractions were collected and the solvent was evaporated. The residue (0.072 g, 50%) was crystallized from CH₃CN. The precipitate was filtered off and dried, yielding 0.049 g (30%) of compound 5 (M.P.: 178° C.).

Example B3

Preparation of Compound 14

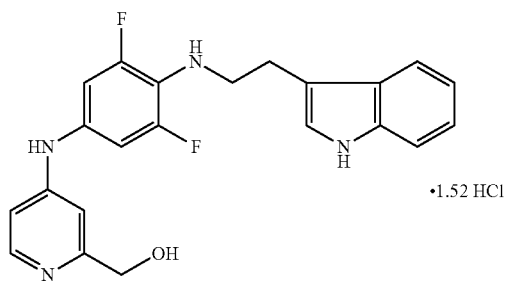 [SMILES: OCc1cc(Nc2cc(F)c(NCCc3c[nH]c4ccccc34)c(F)c2)ccn1]

A mixture of intermediate 2 (0.0012 mol), 4-chloro-2-pyridinemethanol (0.0012 mol) and HCl/dioxane 4N (0.0002 mol) in CH₃CN (10 ml) was stirred at 65° C. for 18 hours, then cooled to room temperature, poured out into K₂CO₃ 10% aqueous solution and extracted with CH₂Cl₂/CH₃OH (few). The organic layer was separated, dried (MgSO₄), filtered and the solvent was evaporated till dryness. The residue (0.52 g) was purified by column chromatography over kromasil (eluent: CH₂Cl₂/CH₃OH/NH₄OH 97/3/0.3 to 91/9/0.9; 3-5 µm). The pure fractions were collected and the solvent was evaporated. The residue (0.3 g, 60%) was crystallized from CH₃CN. The precipitate was filtered off and dried, yielding 0.292 g (51%) of compound 14 as a hydrochloric acid salt (0.1.52HCl, M.P.: 110° C.).

Compounds No. 15, 16 and 60 were made according to example B3. please confirm

Example B4 a) Preparation of Compound 24

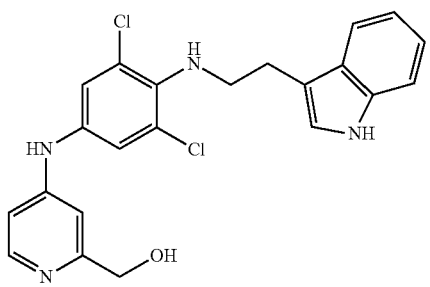 [SMILES: OCc1cc(Nc2cc(Cl)c(NCCc3c[nH]c4ccccc34)c(Cl)c2)ccn1]

A mixture of intermediate 6a (0.0007 mol) and 4-chloro-2-pyridinemethanol (0.0007 mol) in HCl/dioxane 4N (0.0001 mol), CH₃CN (2.5 ml) and EtOH (1 ml) was stirred at 65° C. for 18 hours. The mixture was cooled at room temperature, diluted with CH₂Cl₂ and washed with K₂CO₃ 10% aqueous solution. The organic layer was decanted, dried (MgSO₄), filtered and the solvent was evaporated till 15 ml. The residue was filtered off and dried, yielding 0.168 g (64%) of compound 24 (M.P.: 115° C.).

b) Preparation of Compound 25

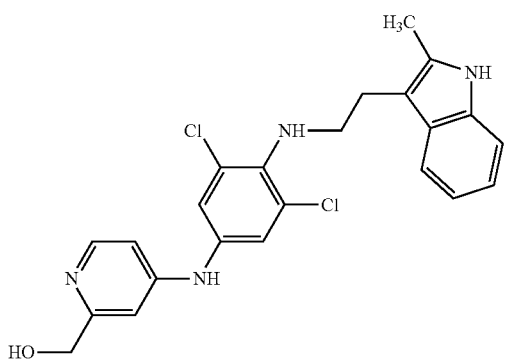 [SMILES: Cc1[nH]c2ccccc2c1CCNc1c(Cl)cc(Nc2ccnc(CO)c2)cc1Cl]

A mixture of intermediate 6b (0.0007 mol) and 4-chloro-2-pyridinemethanol (0.0007 mol) in HCl/dioxane 4N (0.0001 mol), CH₃CN (2 ml) and EtOH (0.8 ml) was stirred at 65° C. for 18 hours. The mixture was cooled at room temperature, poured into K₂CO₃ 10% aqueous solution and extracted with CH₂Cl₂. The precipitate was filtered, washed with CH₃CN and dried, yielding 0.155 g (53%) of compound 25 (M.P.: 186° C.).

Compounds No. 26, 27 and 28 were made according to example B4b).

c) Preparation of Compound 31

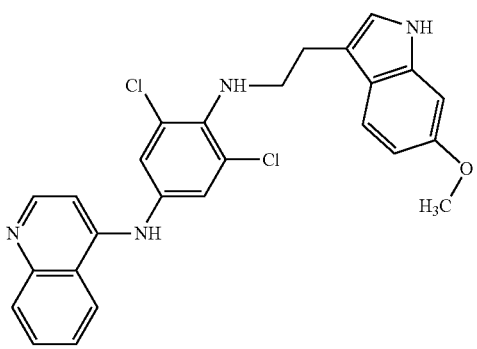 [SMILES: COc1ccc2c(CCNc3c(Cl)cc(Nc4ccnc5ccccc45)cc3Cl)c[nH]c2c1]

A mixture of intermediate 6c (0.0008 mol) and 4-chloroquinoline (0.0009 mol) in HCl/dioxane 4N (0.0001 mol), CH$_3$CN (2.5 ml) and EtOH (1 ml) was stirred at 65° C. for 48 hours. The mixture was cooled at room temperature, poured into K$_2$CO$_3$ 10% aqueous solution and extracted with CH$_2$Cl$_2$. The precipitate was filtered, washed with CH$_3$CN and dried, yielding 0.266 g (71%) of compound 31 (M.P.: 175° C.).

Compounds No. 29, 30 and 32 were made according to example B4c).

Example B5

Preparation of Compound 17

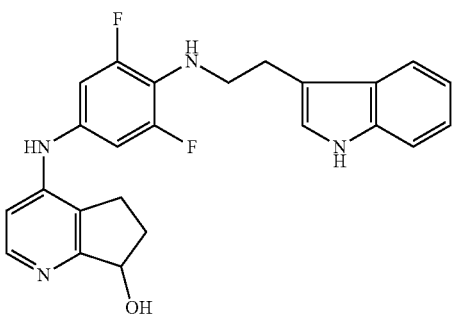 [SMILES: OC1CCc2c(Nc3cc(F)c(NCCc4c[nH]c5ccccc45)c(F)c3)ccnc21]

A mixture of intermediate 2 (0.0012 mol), 4-chloro-6,7-dihydro-5H-cyclopenta[b]pyridin-7-ol (0.0012 mol) and HCl/dioxane 4N (0.0025 mol) in CH$_3$CN (10 ml) was stirred at 65° C. for 18 hours, then cooled to room temperature, poured out into K$_2$CO$_3$ 10% aqueous solution and extracted with CH$_2$Cl$_2$/CH$_3$OH (few). The organic layer was separated, dried (MgSO$_4$), filtered and the solvent was evaporated till dryness. The residue (0.54 g) was purified by column chromatography over kromasil (eluent: CH$_2$Cl$_2$/CH$_3$OH/NH$_4$OH 97/3/0.3 to 88/12/1.2; 3-5 µm). The pure fractions were collected and the solvent was evaporated. The residue (0.14 g, 26%) was crystallized from CH$_3$CN. The precipitate was filtered off and dried, yielding 0.113 g (21%) of compound 17 (M.P.: 147° C.).

Compounds No. 18, 19, 20, 21, 22, 23, 33, 34, 35, 36, 37 and 61 were made according to example B5.

Example B6 a) Preparation of Compound 9

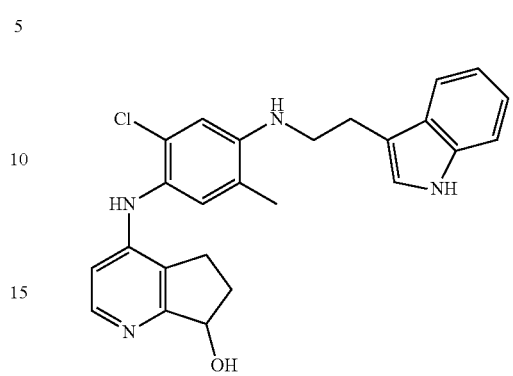

A mixture of intermediate 8a (0.0006 mol) and 4-chloro-6,7-dihydro-5H-cyclopenta[b]pyridin-7-ol (0.006 mol) in HCl/dioxane 4N (0.0001 mol), CH$_3$CN (2 ml) and CH$_3$OH (0.8 ml) was stirred at 65° C. for 18 hours then cooled at room temperature. 3N HCl (0.0025 mol) was added. The mixture was stirred at 65° C. for 18 hours, cooled at room temperature, diluted with CH$_2$Cl$_2$ and washed with K$_2$CO$_3$ 10% aqueous solution. The organic layer was decanted, dried (MgSO$_4$), filtered and the solvent was evaporated till dryness. The residue (0.36 g) was purified by column chromatography over kromasil (eluent: CH$_2$Cl$_2$/CH$_3$OH/NH$_4$OH 98/2/0.2 to 90/10/1; 3.5 µm). The pure fractions (0.14 g) were crystallized from CH$_3$CN. The precipitate was filtered off and dried, yielding 0.120 g (47%) of compound 9 (M.P.: 207° C.).

Compounds No. 7 and 8 were made according to example B6a).

b) Preparation of Compound 10

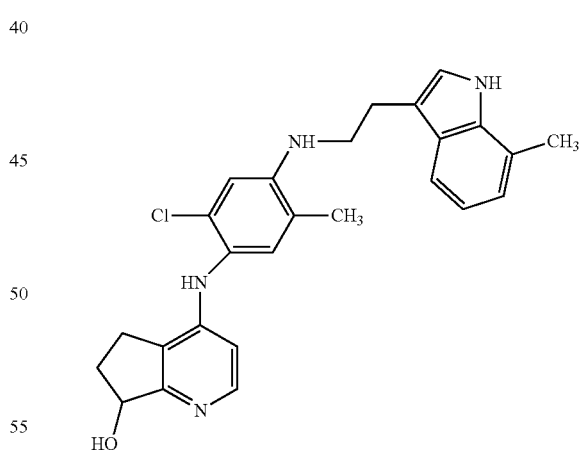

A mixture of intermediate 8b (0.0007 mol) and 4-chloro-6,7-dihydro-5H-cyclopenta[b]pyridin-7-ol (0.0008 mol) in HCl/dioxane 4N (0.0001 mol), CH$_3$CN (2 ml) and CH$_3$OH (0.8 ml) was stirred at 65° C. for 48 hours then cooled to room temperature, poured out to into K$_2$CO$_3$ 10% aqueous solution and extracted with CH$_2$Cl$_2$. The organic layer was separated, dried (MgSO$_4$), filtered and the solvent was evaporated. The residue was purified by column chromatography over kromasil (eluent: CH$_2$Cl$_2$/CH$_3$OH/NH$_4$OH 98/2/0.2 to 90/10/1; 3.5 µm). The pure fractions were Example B7

Preparation of Compound 53

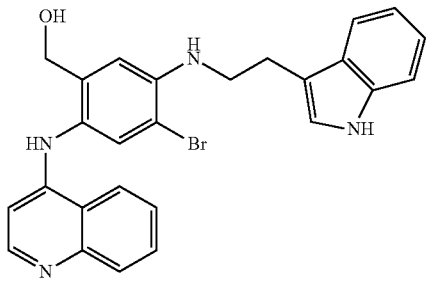 [SMILES: OCc1cc(NCCc2c[nH]c3ccccc23)c(Br)cc1Nc1ccnc2ccccc12]

A mixture of intermediate 11 (0.0011 mol), 4-chloroquinoline (0.0012 mol) and HCl/dioxane 4N (0.0002 mol) in CH$_3$CN (2.5 ml) and EtOH (1 ml) was stirred at 65° C. for 18 hours, then cooled to room temperature, poured out into K$_2$CO$_3$ 10% aqueous solution and extracted with CH$_2$Cl$_2$. The organic layer was separated, dried (MgSO$_4$), filtered and the solvent was evaporated. The precipitate was filtered off and dried, yielding 0.366 g (66%) of compound 53 (M.P.: 192° C.).

Compounds No. 51, 52, 53 and 54 were made according to example B7.

Example B8

Preparation of Compound 59

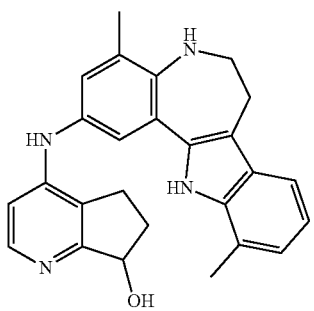 [SMILES: Cc1cc(Nc2ccnc3c2CCC3O)cc2c1NCCc1c-2[nH]c2c(C)cccc12]

A solution of intermediate 14 (0.0005 mol) in 3N HCl (5 ml) and THF (1 ml) was stirred at 100° C. for 10 days. K$_2$CO$_3$ 10% aqueous solution and CH$_2$Cl$_2$ were added. The mixture was extracted. The organic layer was separated, dried (MgSO$_4$), filtered off and concentrated. The residue (0.2 g) was purified by column chromatography (eluent: CH$_2$Cl$_2$/CH$_3$OH/NH$_4$OH 93/7/0.1). The residue (0.010 g, 5%) was purified by column chromatography (eluent: CH$_2$Cl$_2$/CH$_3$OH/NH$_4$OH 93/7/0.7). The pure fractions were collected and the solvent was evaporated, yielding 0.003 g (1.5%) of compound 59.

collected and the solvent was evaporated till dryness. The residue was crystallized from CH$_3$CN. The precipitate was filtered off and dried, yielding 0.055 g (17%) of compound 10 (M.P.: 237° C.).

Example B9 a) Preparation of Compound 1

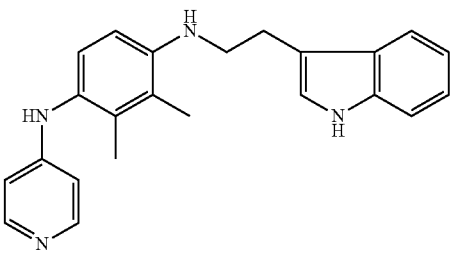 [SMILES: Cc1c(NCCc2c[nH]c3ccccc23)ccc(Nc2ccncc2)c1C]

A mixture of intermediate 16 (0.0005 mol), 4-bromopyridine, hydrochloride (1:1) (0.0005 mol) and DIPEA (0.0004 mol) in CH$_3$CN (1.5 ml) and EtOH (0.5 ml) was stirred at 65° C. for 18 hours. HCl (0.2 eq) and dioxane 4N (29 µl) were added. The mixture was stirred at 65° C. for 18 hours, then cooled to room temperature, poured out into K$_2$CO$_3$ 10% aqueous solution and extracted with EtOAc. The organic layer was separated, dried (MgSO$_4$), filtered and the solvent was evaporated till dryness. The residue (0.24 g) was purified by column chromatography over kromasil (eluent: CH$_2$Cl$_2$/CH$_3$OH/NH$_4$OH 93/7/0.5; 10 µm). The pure fractions were collected and the solvent was evaporated, yielding 0.039 g (19%) of compound 1 (M.P.: 186° C.).

b) Preparation of Compound 2

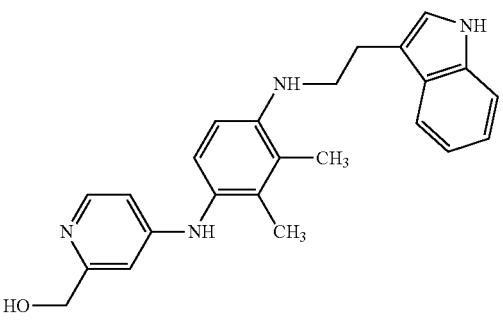 [SMILES: Cc1c(NCCc2c[nH]c3ccccc23)ccc(Nc2ccnc(CO)c2)c1C]

A mixture of intermediate 16 (0.0005 mol), 4-chloro-2-pyridinemethanol (0.0005 mol) and HCl/dioxane 4N (0.0001 mol) in CH$_3$CN (1.5 ml) and EtOH (0.5 ml) was stirred at 65° C. for 18 hours. HCl (0.2 eq) and dioxane 4N (29 µl) were added. The mixture was stirred at 65° C. for 18 hours, then cooled to room temperature, poured out into K$_2$CO$_3$ 10% aqueous solution and extracted with EtOAc. The organic layer was separated, dried (MgSO$_4$), filtered and the solvent was evaporated till dryness. The residue (0.18 g) was purified by column chromatography over silica gel (eluent: CH$_2$Cl$_2$/CH$_3$OH/NH$_4$OH 93/7/0.5; 10 µm). The pure fractions were collected and the solvent was evaporated. The residue (0.03 g, 14%) was crystallized from CH$_3$CN/DIPE. The precipitate was filtered off and dried, yielding 0.03 g (9%) of compound 2 (M.P.: 163° C.).

Example B10

Preparation of Compound 55

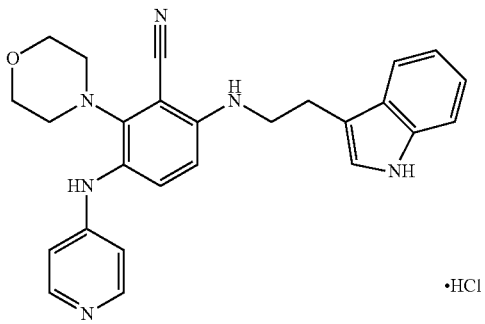 [SMILES: N#Cc1c(NCCc2c[nH]c3ccccc23)ccc(Nc2ccncc2)c1N1CCOCC1 ; Cl]

•HCl

A mixture of intermediate 18 (0.0008 mol) and 4-bromopyridine, hydrochloride (1:1) (0.0008 mol) in DIPEA (0.0006 mol), CH$_3$CN (2.5 ml) and EtOH (1 ml) was stirred at 65° C. for 18 hours then cooled at room temperature, poured out into K$_2$CO$_3$ 10% aqueous solution and extracted with CH$_2$Cl$_2$. The organic layer was decanted, dried (MgSO$_4$), filtered and the solvent was evaporated till dryness. The residue (0.357 g) was purified by column chromatography over silica gel (eluent: CH$_2$Cl$_2$/CH$_3$OH/NH$_4$OH 95/5/0.5; 15-40 µm). The solvent of pure fractions was evaporated till dryness. The residue (0.135 g) was crystallized from CH$_3$CN/EtOH/DIPE, yielding 0.126 g (35%) of compound 55 as a hydrochloric acid salt (0.0.99HCl, M.P.: 245° C.).

Compounds No. 56, 57 and 58 were made according to example B10.

Example B11

Preparation of Compound 50

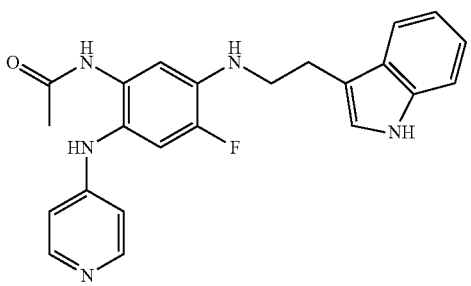 [SMILES: CC(=O)Nc1cc(NCCc2c[nH]c3ccccc23)c(F)cc1Nc1ccncc1]

A mixture of intermediate 20 (0.001 mol), 4-bromopyridine, hydrochloride (1:1) (0.001 mol) and DIPEA (0.0008 mol) in CH$_3$CN (2.5 ml) and EtOH (1 ml) was stirred at 65° C. for 18 hours, then cooled to room temperature, poured out into K$_2$CO$_3$ 10% aqueous solution and extracted with CH$_2$Cl$_2$. The organic layer was separated, dried (MgSO$_4$), filtered and the solvent was evaporated till dryness. The residue (0.37 g) was purified by column chromatography over kromasil (eluent: CH$_2$Cl$_2$/CH$_3$OH/NH$_4$OH 98/2/0.2 to 88/12/1.2; 3.5 µm). The pure fractions were collected and the solvent was evaporated till dryness. The residue was crystallized from CH$_3$CN. The precipitate was filtered off and dried, yielding 0.095 g (23%) of compound 50 (M.P.: 241° C.).

Example B12

Preparation of Compound 49

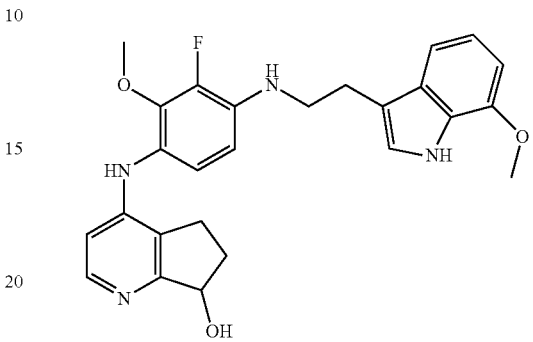

A mixture of intermediate 22 (0.0015 mol) and 4-chloro-6,7-dihydro-5H-cyclopenta[b]pyridin-7-ol (0.0016 mol) in HCl/dioxane 4N (0.0003 mol), CH$_3$CN (3 ml) and EtOH (1.2 ml) was stirred at 65° C. for 18 hours then cooled at room temperature, poured out into K$_2$CO$_3$ 10% aqueous solution and extracted with CH$_2$Cl$_2$. The organic layer was decanted, dried (MgSO$_4$), filtered and the solvent was evaporated till dryness. The residue (0.74 g) was purified by column chromatography over kromasil (eluent: CH$_2$Cl$_2$/CH$_3$OH/NH$_4$OH 100 to 93/7/0.7; 5 µm). The solvent was evaporated till dryness. The residue (0.445 g) was crystallized from EtOH. The residue was filtered off and dried, yielding 0.244 g (36%) of compound 49 (M.P.: 123° C.).

Compounds No. 38, 39, 40, 41, 42, 43, 44, 45, 46, 47 and 48 were made according to example B12.

Example B13

Preparation of Compound 6

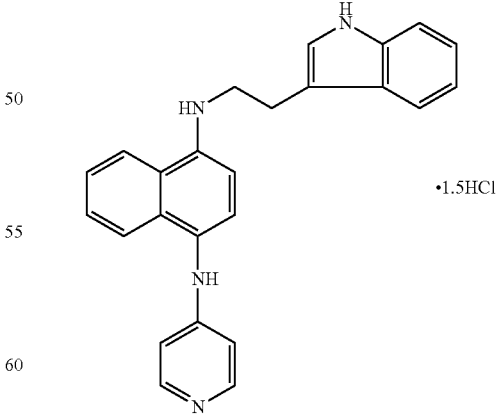

•1.5HCl

A mixture of intermediate 24 (0.0008 mol) and 4-bromopyridine, hydrochloride (1:1) (0.0008 mol) in DMF (3 ml) was stirred at 105° C. for 1 hour and 30 minutes, then cooled to room temperature and poured out into K$_2$CO$_3$ 10% aqueous solution. The precipitate was filtered, washed with water several times and taken up in CH₂Cl₂/CH₃OH (few). The organic layer was separated, dried (MgSO₄), filtered and the solvent was evaporated till dryness. The residue (0.38 g) was purified by column chromatography over kromasil (eluent: CH₂Cl₂/CH₃OH/NH₄OH 96/4/0.4 to 88/12/1.2; 5 μm). The pure fractions were collected and the solvent was evaporated. The crude oil (0.09 g, 23%) was dissolved in isopropanol and cooled in a bath of ice. HCl/isopropanol 5N (2 eq) was added. The precipitate was filtered off and dried, yielding 0.063 g (16%) of compound 6 (melting point: 166° C.).

Example B14

Preparation of Compound 62

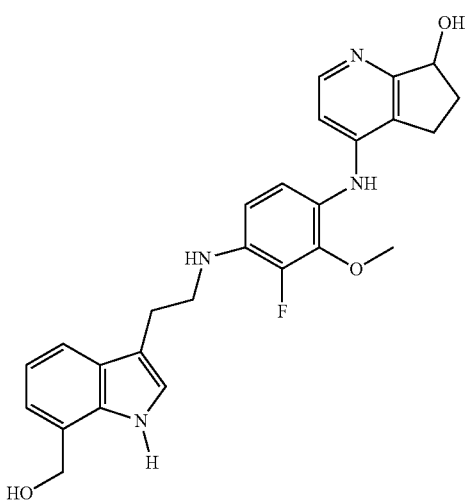 [SMILES: COc1c(Nc2ccnc3c2CCC3O)ccc(NCCc2c[nH]c3c(CO)cccc23)c1F]

Lithium aluminium hybrid in 1M THF (0.398 mmol) was added portionwise to a solution of intermediate 30 in THF at 5° C. The mixture was stirred for 2 hours at room temperature. Water was added carefully at 5° C. EtOAc was added. The reaction mixture was filtered over celite and extracted. The organic layer was separated, dried over MgSO₄, filtered and concentrated. The crude (0.12 g) was purified by column chromatography over silica gel (eluent: CH₂Cl₂/CH₃OH/NH₄OH 95/5/0.5; 30 g 15-40 μm). The pure fractions were collected and the solvent was evaporated, yielding 0.042 g of compound 62.

Example B15

Preparation of Compounds 63 and 64

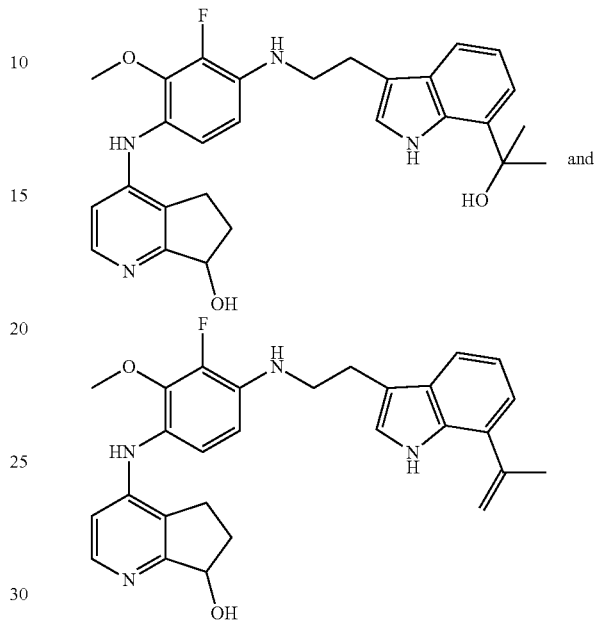

compound 63 and compound 64

A solution of intermediate 38 (0.92 mmol), 4-chloro-6,7-dihydro-5H-cyclopenta[b]pyridin-7-ol (1 mmol), hydrogen chloride in dioxane 4M (46 μl) in CH₃CN (10 ml) was heated at 65° C. for 5 hours. K₂CO₃ 10% aqueous solution and EtOAc were added. The reaction mixture was extracted, the organic layer was separated, dried over MgSO₄, filtered and evaporated. The residue (0.4 g) was purified by high-performance liquid chromatography (Stability Silica 5 μm 150×30.0 mm). Mobile phase (NH₄OH 0.2%; gradient CH₂Cl₂/CH₃OH from 98/2 to 88/12), yielding 49 mg compound 63 and 114 mg of compound 64.

C. Pharmacological Example

A2780 cells are human ovarian carcinoma cells with wild type p53.

The capacity of the compounds to preserve p53 in A2780 cells was measured with the p53 enzyme linked immunosorbent assay (ELISA). The p53 assay is a "sandwich" enzyme immunoassay employing two polyclonal antibodies. A polyclonal antibody, specific for the p53 protein, has been immobilized onto the surface of the plastic wells. Any p53 present in the sample to be assayed will bind to the capture antibody. The biotinylated detector polyclonal antibody also recognizes p53 protein, and will bind to any p53, which has been retained by the capture antibody. The detector antibody, in turn, is bound by horseradish peroxidase-conjugated streptavidin. The horseradish peroxidase catalyses the conversion of the chromogenic substrate o-phenylene diamine, the intensity of which is proportional to the amount of p53 protein bound to the plate. The coloured reaction product is quantified using a spectrophotometer. Quantitation is achieved by the construction of a standard curve using known concentrations of purified recombinant HIS tagged p53 protein (see example C.1).

Cellular activity of the compounds of formula (I) was determined on A2780 tumour cells using a colorimetric assay for cell toxicity or survival (see example C.2).

C.1 P53 ELISA

A2780 cells (ATCC) were cultivated in RPMI 1640 supplemented with 10% fetal calf serum (FCS), 2 mM L-glutamine and gentamycin at 37° C. in a humidified incubator with 5% $CO_2$.

A2780 cells were seeded at 20.000 cells per well in a 96 well plate, cultured for 24 hours and treated with compound for 16 hours at 37° C. in a humidified incubator. After incubation, the cells were washed once with phosphate-buffered saline and 30 µl, per well, low salt RIPA buffer (20 mM tris, pH7.0, 0.5 mM EDTA, 1% Nonidet P40, 0.5% DOC, 0.05% SDS, 1 mM PMSF, 1 µg/ml aprotinin and 0.5 µ/ml leupeptin) was added. Plates were placed on ice for 30 minutes to complete the lysis. p53 protein was detected in de lysates by using the sandwich ELISA, described below.

High binding polystyrene EIA/RIA 96 well plates (Costar 9018) were coated with the capture antibody pAb1801 (Abcam ab28-100) at a concentration of 1 µg/ml in coating buffer (0.1 M $NaHCO_3$ pH8.2), 50 µl per well. The antibody was allowed to adhere overnight at 4° C. Coated plates were washed once with phosphate-buffered saline (PBS)/0.05% Tween 20 and 300 µl of blocking buffer (PBS, 1% bovine serum albumins (BSA)) was added, for an incubation period of 2 hours at room temperature. Dilutions of purified recombinant HIS tagged p53 protein, ranging from 3-200 ng/ml, were made in blocking buffer and used as standards.

Plates were washed twice with PBS/0.05% Tween 20 and blocking buffer or standards were added at 80 µl/well. To the standards, 20 µl of lysis buffer was added. The samples were added to the other wells at 20 µl lysate/well. After an overnight incubation at 4° C., plates were washed twice with PBS/0.05% Tween 20. Aliquots of 100 µl secondary polyclonal antibody p53(FL-393) (Tebubio, sc-6243) at a concentration of 1 µg/ml in blocking buffer were added to each well and allowed to adhere for 2 hours at room temperature. Plates were washed three times with PBS/0.05% Tween 20. Detection antibody anti-rabbit HRP (sc-2004, Tebubio) at 0.04 µg/ml in PBS/1% BSA was added and incubated for 1 hour at room temperature. Plates were washed three times with PBS/0.05% Tween 20 and 100 µl of substrate buffer was added (substrate buffer was prepared shortly before use by adding 1 tablet of 10 mg o-phenylene diamine (OPD) from Sigma and 125 µl 3% $H_2O_2$ to 25 ml OPD buffer: 35 mM citric acid, 66 mM $Na_2HPO_4$, pH5.6). After 5 to 10 minutes, colour reaction was stopped by adding 50 µl stop buffer (1 M $H_2SO_4$) per well. The absorbance at dual wavelengths of 490/655 nm was measured using a Biorad micro plate reader and the results were then analyzed.

For each experiment, controls (containing no drug) and a blank incubation (containing no cells or drugs) were run in parallel. The blank value was subtracted from all control and sample values. For each sample, the value of p53 (in absorbance units) was expressed as the percentage of the value for p53 present in the control. Percentage preservation higher than 140% was defined as significant. Herein the effects of test compounds are expressed as the lowest dose giving at least 140% of the value for p53 present in the control (LAD) (see Table 3 below).

In some of the experiments the assay was adapted for and used in 384-well culture plates

TABLE 3

Results of the compounds that were tested in the above p53 ELISA protocol (A2780 cells)

| Comp. No. | p53-elisa LAD [microM] |
|---|---|
| 1 | >10.0 |
| 2 | 3.0 |
| 3 | >10.0 |
| 4 | >10.0 |
| 5 | 0.3 |
| 6 | 1.0 |
| 7 | >10.0 |
| 8 | >10.0 |
| 9 | >10.0 |
| 10 | 1.0 |
| 11 | >10.0 |
| 12 | 10.0 |
| 13 | >10.0 |
| 14 | >10.0 |
| 15 | >10.0 |
| 16 | >10.0 |
| 17 | 1.0 |
| 18 | >10.0 |
| 19 | >10.0 |
| 20 | >10.0 |
| 21 | >10.0 |
| 22 | >10.0 |
| 23 | >10.0 |
| 24 | >10.0 |
| 25 | 3.0 |
| 26 | >10.0 |
| 27 | >10.0 |
| 28 | >10.0 |
| 29 | 1.0 |
| 30 | 1.0 |
| 31 | 1.0 |
| 32 | >10.0 |
| 33 | 3.0 |
| 34 | 1.0 |
| 35 | 1.0 |
| 36 | 10.0 |
| 37 | 3.0 |
| 38 | 3.0 |
| 39 | 0.1 |
| 40 | 1.0 |
| 41 | 0.3 |
| 42 | 0.1 |
| 43 | 0.3 |
| 44 | 1.0 |
| 45 | 1.0 |
| 46 | 1.0 |
| 47 | 0.1 |
| 48 | 1.0 |
| 49 | 1.0 |
| 50 | >10.0 |
| 51 | >10.0 |
| 52 | >10.0 |
| 53 | >10.0 |
| 54 | >10.0 |
| 55 | >10.0 |
| 56 | >10.0 |
| 57 | >10.0 |
| 58 | >10.0 |
| 59 | — |
| 60 | >10.0 |
| 61 | 0.3 |
| 62 | 3.0 |
| 63 | 1.0 |
| 64 | 0.3 |
| 65 | >10.0 |

C.2 Proliferation Assay

The human U87MG glioma cells were cultured in DMEM medium supplemented with 2 mM L-Glutamine, 1 mM Sodium Pyruvate, 1.5 g/L Sodium Bicarbonate, 50 µg/ml gentamicin and 10% heat inactivated fetal calf serum. (U87MG cells are human glioblastoma cells with wild type p53. In this cell line MDM2 tightly controls p53 expression).

The human A2780 ovarian cancer cells were a kind gift from Dr. T. C. Hamilton (Fox Chase Cancer Centre, Pennsylvania, U.S.A.). The cells were cultured in RPMI 1640 medium supplemented with 2 mM L-Glutamine, 50 µg/ml gentamicin and 10% fetal calf serum.

Reagents Used in the Alamar Blue Assay

Resazurin was purchased from Aldrich (Prod. No. 199303). Potassium ferrocyanide, potassium ferricyanide, $KH_2PO_4$ and $K_2HPO_4$ were purchased from Sigma (Prod. Nos. P9387, P8131, P5655 and P8281, respectively).

Potassium Phosphate Buffer 0.1 M (PPB) was made as follows: 2.72 gram $KH_2PO_4$ and 13.86 gram $K_2HPO_4$ were dissolved in 500 ml milli-Q $H_2O$, the pH was adjusted to pH 7.4 and the volume was brought to 1 litre with milli-Q $H_2O$; the buffer was filter sterilised and stored at room temperature. Resazurin stock solution (PPB-A) was prepared fresh by dissolving 45 mg resazurin in 15 ml PBS. 30 mM potassium ferricyanide (PPB-B) was prepared by dissolving 0.987 gram potassium ferricyanide in 100 ml PPB. 30 mM potassium ferrocyanide (PPB-C) was prepared by dissolving 1.266 gram potassium ferrocyanide in 100 ml PPB.

Mixture of PPB-A, PPB-B and PPB-C was prepared by mixing equal volumes of the respective solutions. Resazurin work solution (herein termed "Alamar Blue" solution) was prepared by diluting said mixture 20×(vol/vol) in PPB and filter sterilising; the Alamar Blue solution could be kept at 4° C. for a maximum of 2 weeks.

Procedure of the Alamar Blue Assay

For experiments in 384 wells plates the cells were seeded at a density of $5 \times 10^3$ cells/ml in Falcon 384-well culture plates (Life Technologies, Merelbeke, Belgium), black with clear bottom, in 45 µl culture medium. Cells were allowed to adhere to plastic for 24 hr. The tested compound was pre-diluted (1/50 in culture medium) and 5 µl pre-diluted compound was added to the wells. Following 4-day incubation, 10 µl of the Alamar Blue solution was added to each well and the cells were further incubated for 5 hrs (A2780) or 6 hrs (U87MG) at 37° C. The fluorescence intensity was measured for each well with a Fluorescence plate reader (Fluorskan, Labsystems, 540 nm excitation and 590 nm emission)

The antiproliferative activity was calculated as percentage of remaining viable cells in treated versus control (untreated cells) conditions. Within an experiment, the result for each experimental condition is the mean of 3 replicate wells. When appropriate, the experiments were repeated to establish full concentration-response curves. When appropriate, $IC_{50}$-values (concentration of the drug, needed to reduce cell growth to 50% of the control) were computed using probit analysis for graded data (Finney, D. J., Probit Analyses, $2^{nd}$ Ed. Chapter 10, Graded Responses, Cambridge University Press, Cambridge 1962). Herein the effects of test compounds are expressed as $pIC_{50}$ (the negative log value of the $IC_{50}$-value) (see Table 4).

TABLE 4

Results of the compounds that were tested in the above cell proliferation protocol

| Comp. No. | A2780 cell proliferation inhibition $pIC_{50}$ | U87MG cell proliferation inhibition $pIC_{50}$ |
|---|---|---|
| 1 | <5 | <5 |
| 2 | <5 | 5.11 |
| 3 | <5 | <5 |
| 4 | <5 | <5 |
| 5 | <5 | <5 |
| 6 | <5 | 5.80 |
| 7 | 5.08 | <5 |
| 8 | <5 | 5.41 |
| 9 | 5.38 | <5 |
| 10 | 5.45 | 5.55 |
| 11 | <5 | 5.31 |
| 12 | <5 | 5.62 |
| 13 | <5 | 5.18 |
| 14 | <5 | <5 |
| 15 | <5 | ~5.23 |
| 16 | <5 | <5 |
| 17 | 5.08 | 5.16 |
| 18 | <5 | 5.17 |
| 19 | <5 | 5.15 |
| 20 | <5 | <5 |
| 21 | <5 | <5 |
| 22 | <5 | 5.29 |
| 23 | <5 | <5 |
| 24 | <5 | <5 |
| 25 | <5 | <5 |
| 26 | <5 | <5 |
| 27 | <5 | <5 |
| 28 | <5 | <5 |
| 29 | 5.58 | <5 |
| 30 | 5.08 | 5.06 |
| 31 | ~5.59 | 5.88 |
| 32 | <5 | 5.48 |
| 33 | <5 | <5 |
| 34 | 5.67 | 5.14 |
| 35 | <5 | <5 |
| 36 | <5 | 5.08 |
| 37 | <5 | <5 |
| 38 | ~5.23 | 6.06 |
| 39 | ~5.59 | 6.07 |
| 40 | ~5.19 | 5.86 |
| 41 | 5.38 | 5.83 |
| 42 | 6.15 | 6.75 |
| 43 | 5.56 | 5.81 |
| 44 | ~5.96 | 6.56 |
| 45 | 6.39 | 6.14 |
| 46 | ~5.46 | 6.08 |
| 47 | ~5.74 | 6.35 |
| 48 | <5 | 5.26 |
| 49 | 6.30 | 6.19 |
| 50 | <5 | <5 |
| 51 | <5 | 5.20 |
| 52 | <5 | 5.33 |
| 53 | <5 | 5.40 |
| 54 | <5 | — |
| 55 | <5 | <5 |
| 56 | <5 | — |
| 57 | <5 | <5 |
| 58 | <5 | <5 |
| 59 | — | — |
| 60 | <5 | 5.18 |
| 61 | <5 | 5.23 |
| 62 | 6.04 | 5.89 |
| 63 | 7.13 | 6.33 |
| 64 | 7.07 | 6.47 |
| 65 | <5 | 5.26 |

~means approximate

D. Analytical Data

Liquid Chromatography (LC) General Procedure

The LC measurement was performed using a UPLC (Ultra Performance Liquid Chromatography) Acquity (Waters) system comprising a binary pump with degasser, an autosampler, a diode-array detector (DAD) and a column as specified in the respective methods below, the column is hold at a temperature of 40° C. Flow from the column was brought to a MS detector. The MS detector was configured with an electrospray ionization source. The capillary needle voltage was 3 kV and the source temperature was maintained at 130° C. on the Quattro (triple quadrupole mass spectrometer from Waters). Nitrogen was used as the nebulizer gas. Data acquisition was performed with a Waters-Micromass MassLynx-Openlynx data system.

In addition to the above general procedure: Reversed phase UPLC was carried out on a Waters Acquity BEH (bridged ethylsiloxane/silica hybrid) C18 column (1.7 µm, 2.1×100 mm) with a flow rate of 0.35 ml/min. Two mobile phases (mobile phase A: 95% 7 mM ammonium acetate/5% acetonitrile; mobile phase B: 100% acetonitrile) were employed to run a gradient condition from 90% A and 10% B (hold for 0.5 minutes) to 8% A and 92% B in 3.5 minutes, hold for 2 min and back to the initial conditions in 0.5 min, hold for 1.5 minutes. An injection volume of 2 was used. Cone voltage was 20 V for positive and negative ionization mode. Mass spectra were acquired by scanning from 100 to 1000 in 0.2 seconds using an interscan delay of 0.1 seconds.

TABLE 5

Analytical LCMS data: $R_t$ is retention time in minutes; [MH]$^+$ means the protonated mass of the compound;

| Compound No. | $R_t$ | [MH]$^+$ |
|---|---|---|
| 59 | 9.28 | 411 |
| 62 | 2.91 | 463 |
| 63 | 3.23 | 491 |
| 64 | 3.72 | 473 |

E. Composition Example: Film-Coated Tablets

Preparation of Tablet Core

A mixture of 100 g of a compound of formula (I), 570 g lactose and 200 g starch is mixed well and thereafter humidified with a solution of 5 g sodium dodecyl sulphate and 10 g polyvinyl-pyrrolidone in about 200 ml of water. The wet powder mixture is sieved, dried and sieved again. Then there is added 100 g microcrystalline cellulose and 15 g hydrogenated vegetable oil. The whole is mixed well and compressed into tablets, giving 10.000 tablets, each comprising 10 mg of a compound of formula (I).

Coating

To a solution of 10 g methyl cellulose in 75 ml of denaturated ethanol there is added a solution of 5 g of ethyl cellulose in 150 ml of dichloromethane. Then there are added 75 ml of dichloromethane and 2.5 ml 1,2,3-propanetriol. 10 g of polyethylene glycol is molten and dissolved in 75 ml of dichloromethane. The latter solution is added to the former and then there are added 2.5 g of magnesium octadecanoate, 5 g of polyvinyl-pyrrolidone and 30 ml of concentrated colour suspension and the whole is homogenated. The tablet cores are coated with the thus obtained mixture in a coating apparatus.

Preferably, where one of $R^2$ or $R^{20}$ together with $R^9$ form a direct bond, said direct bond may connect to a carbon of the central phenyl ring adjacent (i.e., o-position) to the carbon of the central phenyl ring to which the —(CH$_2$)$_m$— group is bound.

As can be appreciated, in compounds of formula (I), and in particular in compounds of any one of the above groups "G1" to "G17", the substituents $R^2$ and $R^{20}$ may be in ortho (o-), meta (m-) or para (p-) positions relative to one another on the central phenyl ring.

When $R^2$ and $R^{20}$ together form a bivalent radical of the formula —(CH$_2$)$_b$— wherein b is 3, 4 or 5, optionally substituted as above, then bonds of said bivalent radical are preferably attached in ortho (o-) positions relative to one another on the central phenyl ring.

As can be appreciated, in compounds of formula (I), and in particular in compounds of any one of the above groups "G1" to "G17", the four substituents on the central phenyl ring may be in various positions relative to one another. For example and without limitation, in compounds where substituents on the central phenyl ring other than $R^2$ and $R^{20}$ are in the para position, i.e., 1-, 4-, the $R^2$ and $R^{20}$ substituents may be in positions 2- and 3-, or in positions 2- and 5-, or in positions 2- and 6-, etc.

Table 2 lists preferred albeit non-limiting examples of compounds of formula (I) that were prepared in the present invention. The following abbreviations were used in the table: .HCl stands for hydrochloric acid salt, mp. stands for melting point.

The invention claimed is:

1. A method of treating a disorder mediated by a p53-MDM2 interaction comprising administering to a patient in need thereof a compound of Formula (I):

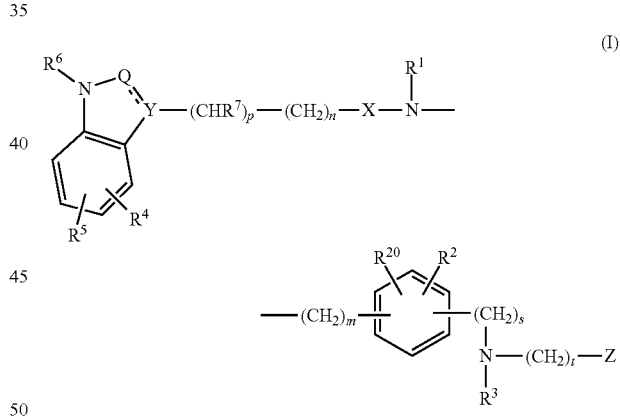

including any stereochemically isomeric form thereof, wherein m is 0, 1 or 2 and when m is 0 then a direct bond is intended;

n is 0, 1, 2 or 3 and when n is 0 then a direct bond is intended;

p is 0 or 1 and when p is 0 then a direct bond is intended;

s is 0 or 1 and when s is 0 then a direct bond is intended;

t is 0 or 1 and when t is 0 then a direct bond is intended;

X is C(=O) or CHR$^8$, wherein $R^8$ is hydrogen; C$_{1-6}$alkyl; C$_{3-7}$cycloalkyl; —C(=O)—NR$^{17}$R$^{18}$; carboxyl; arylC$_{1-6}$alkyloxycarbonyl; heteroaryl; heteroarylcarbonyl; heteroarylC$_{1-6}$alkyloxycarbonyl; piperazinylcarbonyl; pyrrolidinyl; piperidinylcarbonyl;

$C_{1-6}$alkyloxycarbonyl; $C_{1-6}$alkyl substituted with a substituent that is hydroxy, amino, aryl, or heteroaryl; $C_{3-7}$cycloalkyl substituted with a substituent that is hydroxy, amino, aryl or heteroaryl; piperazinylcarbonyl substituted with a substituent that is hydroxy, hydroxy$C_{1-6}$alkyl or hydroxy $C_{1-6}$alkyloxy$C_{1-6}$alkyl; pyrrolidinyl substituted with hydroxy$C_{1-6}$alkyl; or piperidinylcarbonyl substituted with one or two substituents that are hydroxy, $C_{1-6}$alkyl, hydroxy$C_{1-6}$alkyl, $C_{1-6}$alkyloxy$C_{1-6}$alkyl, $C_{1-6}$alkyl(dihydroxy)$C_{1-6}$alkyl or $C_{1-6}$alkyloxy(hydroxy)$C_{1-6}$alkyl;

$R^{17}$ and $R^{18}$ are each independently hydrogen, $C_{1-6}$alkyl, di($C_{1-6}$alkyl)amino$C_{1-6}$alkyl, aryl$C_{1-6}$alkyl, $C_{1-6}$alkyloxy$C_{1-6}$alkyl, hydroxy $C_{1-6}$alkyl, hydroxy$C_{1-6}$alkyl($C_{1-6}$alkyl), or hydroxy$C_{1-6}$alkyl(aryl$C_{1-6}$alkyl);

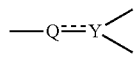

is —CR$^9$=C< and then the dotted line is a bond, —C(=O)—CH<, —C(=O)—N<, —CHR$^9$—CH<, or —CHR$^9$—N<, wherein each $R^9$ is independently hydrogen or $C_{1-6}$alkyl, or wherein $R^9$ together with one of $R^2$ or $R^{20}$ form a direct bond;

$R^1$ is hydrogen; aryl; heteroaryl; $C_{1-6}$alkyloxycarbonyl; $C_{1-12}$alkyl; or $C_{1-12}$alkyl substituted with one or two substituents that are hydroxy, aryl, heteroaryl, amino, $C_{1-6}$alkyloxy, mono- or di($C_{1-6}$alkyl)amino, morpholinyl, piperidinyl, pyrrolidinyl, piperazinyl, $C_{1-6}$alkylpiperazinyl, aryl$C_{1-6}$alkylpiperazinyl, heteroaryl$C_{1-6}$alkylpiperazinyl, $C_{3-7}$cycloalkyl-piperazinyl, or $C_{3-7}$cycloalkyl$C_{1-6}$alkylpiperazinyl;

$R^2$ and $R^{20}$ are each independently halo, hydroxy, cyano, nitro, carboxyl; polyhalo$C_{1-6}$alkyl, polyhalo$C_{1-6}$alkyloxy; $C_{1-6}$alkyl, $C_{3-7}$cycloalkyl, $C_{2-6}$alkenyl, aryl, heteroaryl, aryl$C_{1-6}$alkyl, heteroaryl-$C_{1-6}$alkyl, $C_{3-7}$cycloalkyl$C_{1-6}$alkyl, morpholinyl, piperidinyl, pyrrolidinyl, piperazinyl, $C_{1-6}$alkyloxy, aryloxy, heteroaryloxy, $C_{1-6}$alkylthio, arylthio, heteroarylthio, $C_{1-6}$alkylcarbonyl, $C_{3-7}$cycloalkylcarbonyl, arylcarbonyl, heteroarylcarbonyl, $C_{1-6}$alkyloxycarbonyl, $C_{3-7}$cycloalkyloxycarbonyl, aryloxycarbonyl, heteroaryloxycarbonyl, $C_{1-6}$alkylcarbonyloxy, $C_{3-7}$cycloalkylcarbonyloxy, arylcarbonyloxy or heteroarylcarbonyloxy, any of said groups being optionally and independently substituted with one or more substituents that are halo, hydroxy, cyano, nitro, carboxyl, amino, mono- or di($C_{1-6}$alkyl)amino, $C_{1-6}$alkyl, polyhalo$C_{1-6}$alkyl, aryl, heteroaryl, $C_{1-6}$alkyloxy, $C_{1-6}$alkylcarbonyl, $C_{1-6}$alkyloxycarbonyl and $C_{1-6}$alkylcarbonyloxy; or —(CH$_2$)$_w$—(C(=O))$_y$NR$^{21}$R$^{22}$ wherein w is 0, 1, 2, 3, 4, 5 or 6 and when w is 0 then a direct bond is intended;

y is 0 or 1 and when y is 0 then a direct bond is intended;

$R^{21}$ and $R^{22}$ are each independently hydrogen, $C_{1-6}$alkyl, $C_{3-7}$cycloalkyl, $C_{1-6}$alkylcarbonyl or aryl$C_{1-6}$alkylcarbonyl, any of said groups being optionally and independently substituted with one or more substituents that are halo, hydroxy, amino, mono- or di($C_{1-6}$alkyl)amino, $C_{1-6}$alkyl, polyhalo$C_{1-6}$alkyl, $C_{1-6}$alkyloxy, aryl or heteroaryl;

or $R^{21}$ and $R^{22}$ together with the nitrogen to which they are attached form morpholinyl, piperidinyl, pyrrolidinyl or piperazinyl, any of said groups being optionally and independently substituted with one or more substituents that are $C_{1-6}$alkyl, polyhalo$C_{1-6}$alkyl, $C_{1-6}$alkyloxy, $C_{3-7}$cycloalkyl, $C_{3-7}$cycloalkyl$C_{1-6}$alkyl, aryl$C_{1-6}$alkyl, or heteroaryl$C_{1-6}$alkyl;

or $R^2$ and $R^{20}$ together with the phenyl ring to which they are attached form a naphthalenyl group, optionally substituted with one or more substituents each independently halo, hydroxy, amino, mono- or di($C_{1-6}$alkyl)amino, $C_{1-6}$alkyl, polyhalo$C_{1-6}$alkyl, $C_{1-6}$alkyloxy, aryl, or heteroaryl;

or $R^2$ and $R^{20}$ together form a bivalent radical of the formula —(CH$_2$)$_b$— wherein b is 3, 4 or 5, optionally substituted with one or more substituents that are halo, hydroxy, amino, mono- or di($C_{1-6}$alkyl)amino, $C_{1-6}$alkyl, polyhalo$C_{1-6}$alkyl, $C_{1-6}$alkyloxy, aryl, or heteroaryl;

or one of $R^2$ or $R^{20}$ is as defined above and the other one of $R^2$ or $R^{20}$ together with $R^9$ form a direct bond;

$R^3$ is hydrogen; $C_{1-6}$alkyl; heteroaryl; $C_{3-7}$cycloalkyl; $C_{1-6}$alkyl substituted with a substituent that is hydroxy, amino, aryl, or heteroaryl; or $C_{3-7}$cycloalkyl substituted with a substituent that is hydroxy, amino, aryl, or heteroaryl;

$R^4$ and $R^5$ are each independently hydrogen, halo, $C_{1-6}$alkyl, hydroxy$C_{1-6}$alkyl, polyhalo-$C_{1-6}$alkyl, cyano, cyano$C_{1-6}$alkyl, hydroxy, amino, $C_{2-6}$alkenyl or $C_{1-6}$alkyloxy; or $R^4$ and $R^5$ together form a bivalent radical that is methylenedioxy or ethylenedioxy;

$R^6$ is hydrogen, $C_{1-6}$alkyloxycarbonyl, or $C_{1-6}$alkyl;

when p is 1 then $R^7$ is hydrogen, aryl$C_{1-6}$alkyl, hydroxy, or heteroaryl$C_{1-6}$alkyl;

Z is a radical that is:

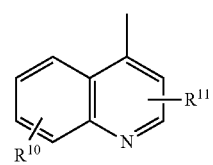

(a-1)

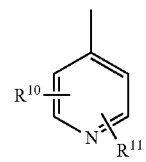

(a-2)

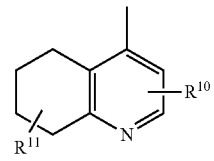

(a-3)

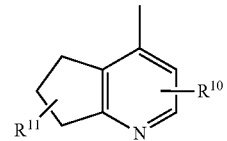

(a-4)

-continued (a-5)

(a-6)

(a-7)

(a-8)

(a-9)

wherein
R$^{10}$ or R$^{11}$ are each independently hydrogen, halo, hydroxy, amino, C$_{1-6}$alkyl, nitro, polyhaloC$_{1-6}$alkyl, cyano, cyanoC$_{1-6}$alkyl, tetrazoloC$_{1-6}$alkyl, aryl, heteroaryl, arylC$_{1-6}$alkyl, heteroarylC$_{1-6}$alkyl, aryl(hydroxy)C$_{1-6}$alkyl, heteroaryl(hydroxy)C$_{1-6}$alkyl, arylcarbonyl, heteroarylcarbonyl, C$_{1-6}$alkylcarbonyl, arylC$_{1-6}$alkylcarbonyl, heteroarylC$_{1-6}$alkylcarbonyl, C$_{1-6}$alkyloxy, C$_{3-7}$cycloalkylcarbonyl, C$_{3-7}$cycloalkyl(hydroxy)C$_{1-6}$alkyl, arylC$_{1-6}$alkyloxyC$_{1-6}$alkyl, C$_{1-6}$alkyloxyC$_{1-6}$alkyloxyC$_{1-6}$alkyl, C$_{1-6}$alkylcarbonyloxyC$_{1-6}$alkyl, C$_{1-6}$alkyloxycarbonylC$_{1-6}$alkyloxyC$_{1-6}$alkyl, hydroxyC$_{1-6}$alkyloxyC$_{1-6}$alkyl, C$_{1-6}$alkyloxycarbonylC$_{2-6}$alkenyl, C$_{1-6}$alkyloxyC$_{1-6}$alkyl, C$_{1-6}$alkyloxycarbonyl, C$_{1-6}$alkylcarbonyloxy, aminocarbonyl, hydroxyC$_{1-6}$alkyl, aminoC$_{1-6}$alkyl, hydroxycarbonyl, hydroxycarbonylC$_{1-6}$alkyl, or —(CH$_2$)$_v$—(C(=O))$_r$—(CHR$^{19}$)$_u$—NR$^{13}$R$^{14}$, wherein
v is 0, 1, 2, 3, 4, 5, or 6 and when v is 0 then a direct bond is intended;
r is 0 or 1 and when r is 0 then a direct bond is intended;
u is 0, 1, 2, 3, 4, 5, or 6 and when u is 0 then a direct bond is intended;
R$^{19}$ is hydrogen or C$_{1-6}$alkyl;
R$^{13}$ and R$^{14}$ are each independently hydrogen; C$_{1-12}$alkyl; C$_{1-6}$alkylcarbonyl; C$_{1-6}$alkylsulfonyl; arylC$_{1-6}$alkylcarbonyl; C$_{3-7}$cycloalkyl; C$_{3-7}$cycloalkylcarbonyl; —(CH$_2$)$_k$—NR$^{15}$R$^{16}$; C$_{1-12}$alkyl substituted with a substituent that is hydroxy, hydroxycarbonyl, cyano, C$_{1-6}$alkyloxycarbonyl, C$_{1-6}$alkyloxy, aryl or heteroaryl; or C$_{3-7}$cycloalkyl substituted with a substituent that is hydroxy, C$_{1-6}$alkyloxy, aryl, amino, arylC$_{1-6}$alkyl, heteroaryl or heteroarylC$_{1-6}$alkyl; or
R$^{13}$ and R$^{14}$ together with the nitrogen to which they are attached form morpholinyl, piperidinyl, pyrrolidinyl, piperazinyl, or piperazinyl substituted with a substituent that is C$_{1-6}$alkyl, arylC$_{1-6}$alkyl, arylC$_{1-6}$alkyloxycarbonyl, heteroarylC$_{1-6}$alkyl, C$_{3-7}$cycloalkyl, or C$_{3-7}$cycloalkylC$_{1-6}$alkyl;
wherein
k is 0, 1, 2, 3, 4, 5, or 6 and when k is 0 then a direct bond is intended;
R$^{15}$ and R$^{16}$ are each independently hydrogen; C$_{1-12}$alkyl; arylC$_{1-6}$alkyloxycarbonyl; C$_{3-7}$cycloalkyl; C$_{1-12}$alkyl substituted with a substituent that is hydroxy, C$_{1-6}$alkyloxy, aryl, or heteroaryl; or C$_{3-7}$cycloalkyl substituted with a substituent that is hydroxy, C$_{1-6}$alkyloxy, aryl, arylC$_{1-6}$alkyl, heteroaryl, or heteroarylC$_{1-6}$alkyl; or
R$^{15}$ and R$^{16}$ together with the nitrogen to which they are attached form morpholinyl, piperazinyl, or piperazinyl substituted with C$_{1-6}$alkyloxycarbonyl;
R$^{12}$ is hydrogen; C$_{1-6}$alkyl; C$_{3-7}$cycloalkyl; C$_{1-6}$alkyl substituted with a substituent that is hydroxy, amino, C$_{1-6}$alkyloxy, or aryl; or C$_{3-7}$cycloalkyl substituted with a substituent that is hydroxy, amino, aryl, or C$_{1-6}$alkyloxy;
aryl is phenyl or naphthalenyl;
each phenyl or naphthalenyl can optionally be substituted with one, two or three substituents each independently halo, hydroxy, C$_{1-6}$alkyl, amino, polyhaloC$_{1-6}$alkyl or C$_{1-6}$alkyloxy; and
each phenyl or naphthalenyl can optionally be substituted with a bivalent radical that is methylenedioxy or ethylenedioxy;
heteroaryl is pyridinyl, indolyl, quinolinyl, imidazolyl, furanyl, thienyl, oxadiazolyl, tetrazolyl, benzofuranyl or tetrahydrofuranyl;
each pyridinyl, indolyl, quinolinyl, imidazolyl, furanyl, thienyl, oxadiazolyl, tetrazolyl, benzofuranyl, or tetrahydrofuranyl can optionally be substituted with one, two or three substituents each independently halo, hydroxy, C$_{1-6}$alkyl, amino, polyhaloC$_{1-6}$alkyl, aryl, arylC$_{1-6}$alkyl or C$_{1-6}$alkyloxy; or
each pyridinyl, indolyl, quinolinyl, imidazolyl, furanyl, thienyl, benzofuranyl, or tetrahydrofuranyl can optionally be substituted with a bivalent radical that is methylenedioxy or ethylenedioxy;
wherein when R$^2$ or R$^{20}$ is C$_{1-6}$alkyl or C$_{1-6}$alkyloxy, then R$^2$ or R$^{20}$ is not fluorine;
an N-oxide form thereof, an addition salt thereof or a solvate thereof.

2. The method according to claim 1, wherein
R$^4$ and R$^5$ are each independently hydrogen, halo, C$_{1-6}$alkyl, polyhaloC$_{1-6}$alkyl, cyano, cyanoC$_{1-6}$alkyl, hydroxy, amino, or C$_{1-6}$alkyloxy, or
R$^4$ and R$^5$ together form a bivalent radical that is methylenedioxy or ethylenedioxy;
R$^{15}$ and R$^{16}$ are each independently hydrogen, C$_{1-6}$alkyl, arylC$_{1-6}$alkyloxycarbonyl, C$_{3-7}$cycloalkyl, C$_{1-12}$alkyl substituted with a substituent that is from hydroxy, C$_{1-6}$alkyloxy, aryl, or heteroaryl, or C$_{3-7}$cycloalkyl substituted with a substituent selected from hydroxy, $C_{1-6}$alkyloxy, aryl, aryl$C_{1-6}$alkyl, heteroaryl, or heteroaryl$C_{1-6}$alkyl, or $R^{15}$ and $R^{16}$ together with the nitrogen to which they are attached form morpholinyl, piperazinyl, or piperazinyl substituted with $C_{1-6}$alkyloxycarbonyl.

3. The method according to claim 1, wherein

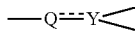

is —$CR^9$=C< and then the dotted line is a bond, —C(=O)—CH<, —CHR$^9$—CH<, or —CHR$^9$—N<, wherein each $R^9$ is independently hydrogen or $C_{1-6}$alkyl, or wherein $R^9$ together with one of $R^2$ or $R^{20}$ form a direct bond.

4. The method according to claim 3 wherein

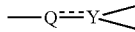

is —$CR^9$=C< and then the dotted line is a bond, —CHR$^9$—CH<, or —CHR$^9$—N<.

5. The method according to claim 4 wherein

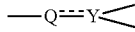

is —$CR^9$=C< and then the dotted line is a bond.

6. The method according to claim 1, wherein
X is C(=O) or CHR$^8$ and R$^8$ is hydrogen; —C(=O)—NR$^{17}$R$^{18}$; aryl$C_{1-6}$alkyloxycarbonyl; $C_{1-6}$alkyl substituted with hydroxyl; piperazinylcarbonyl substituted with hydroxyl; hydroxy$C_{1-6}$alkyl; hydroxy$C_{1-6}$alkyloxy$C_{1-6}$alkyl; pyrrolidinyl substituted with hydroxyl-$C_{1-6}$alkyl; or piperidinylcarbonyl substituted with one or two substituents that are hydroxy, $C_{1-6}$alkyl, hydroxy$C_{1-6}$alkyl, $C_{1-6}$alkyloxy$C_{1-6}$alkyl, $C_{1-6}$alkyl(dihydroxy)$C_{1-6}$alkyl or $C_{1-6}$alkyloxy(hydroxy)$C_{1-6}$alkyl;
R$^{17}$ and R$^8$ are each independently hydrogen, $C_{1-6}$alkyl, di($C_{1-6}$alkyl)amino$C_{1-6}$alkyl, aryl$C_{1-6}$alkyl, $C_{1-6}$alkyloxy$C_{1-6}$alkyl or hydroxy$C_{1-6}$alkyl;

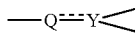

is —$CR^9$=C<, —CHR$^9$—CH< or —CHR$^9$—N<;
R$^1$ is hydrogen, heteroaryl, $C_{1-6}$alkyloxycarbonyl, $C_{1-12}$alkyl or $C_{1-12}$alkyl substituted with heteroaryl;
R$^3$ is hydrogen, $C_{1-6}$alkyl or heteroaryl;
R$^4$ and R$^5$ are each independently hydrogen, halo, $C_{1-6}$alkyl, cyano, cyano$C_{1-6}$alkyl, hydroxy or $C_{1-6}$alkyloxy;
when p is 1 then R$^7$ is aryl$C_{1-6}$alkyl or hydroxy;
Z is a (a-1), (a-2), (a-3), (a-4), (a-5), (a-6), (a-7), (a-8) or (a-9);
R$^{10}$ or R$^{11}$ are each independently hydrogen, halo, hydroxy, amino, $C_{1-6}$alkyl, nitro, polyhalo$C_{1-6}$alkyl, cyano, cyano$C_{1-6}$alkyl, tetrazolo$C_{1-6}$alkyl, aryl, heteroaryl, heteroaryl$C_{1-6}$alkyl, aryl(hydroxy)$C_{1-6}$alkyl, arylcarbonyl, $C_{1-6}$alkylcarbonyl, $C_{3-7}$cycloalkylcarbonyl, $C_{3-7}$cycloalkyl(hydroxy)$C_{1-6}$alkyl, aryl$C_{1-6}$alkyloxy$C_{1-6}$alkyl, $C_{1-6}$alkyloxy$C_{1-6}$alkyloxy$C_{1-6}$alkyl, $C_{1-6}$alkylcarbonyloxy$C_{1-6}$alkyl, $C_{1-6}$alkyloxycarbonyl$C_{1-6}$alkyloxy$C_{1-6}$alkyl, hydroxy$C_{1-6}$alkyloxy$C_{1-6}$alkyl, $C_{1-6}$alkyloxycarbonyl$C_{2-6}$alkenyl, $C_{1-6}$alkyloxy$C_{1-6}$alkyl, $C_{1-6}$alkyloxycarbonyl, aminocarbonyl, hydroxy$C_{1-6}$alkyl, amino$C_{1-6}$alkyl, hydroxycarbonyl, hydroxycarbonyl$C_{1-6}$alkyl or —(CH$_2$)$_v$—(C(=O))$_r$—(CHR$^{19}$)$_u$—NR$^{13}$R$^{14}$;
v is 0 or 1;
u is 0 or 1;
R$^{12}$ is hydrogen or $C_{1-6}$alkyl;
R$^{13}$ and R$^{14}$ are each independently hydrogen; $C_{1-12}$alkyl; $C_{1-6}$alkylcarbonyl; $C_{1-6}$alkylsulfonyl; aryl$C_{1-6}$alkylcarbonyl; $C_{3-7}$cycloalkylcarbonyl; —(CH$_2$)$_k$—NR$^{15}$R$^{16}$; $C_{1-12}$alkyl substituted with a substituent that is hydroxy, hydroxycarbonyl, cyano, $C_{1-6}$alkyloxycarbonyl or aryl; or
R$^{13}$ and R$^{14}$ together with the nitrogen to which they are attached form morpholinyl, pyrrolidinyl, piperazinyl or piperazinyl substituted with a substituent that is $C_{1-6}$alkyl or aryl$C_{1-6}$alkyloxycarbonyl;
k is 2;
R$^{15}$ and R$^{16}$ are each independently hydrogen, $C_{1-6}$alkyl or aryl$C_{1-6}$alkyloxycarbonyl; or
R$^{15}$ and R$^{16}$ together with the nitrogen to which they are attached form morpholinyl or piperazinyl, or piperazinyl substituted with $C_{1-6}$alkyloxycarbonyl;
aryl is phenyl or phenyl substituted with halo; and
heteroaryl is pyridinyl, indolyl, oxadiazolyl or tetrazolyl; and each pyridinyl, indolyl, oxadiazolyl or tetrazolyl can optionally be substituted with one substituent that is $C_{1-6}$alkyl, aryl or aryl$C_{1-6}$alkyl.

7. The method of claim 1, wherein
s is 0;
t is 0;
m is 0;
p is 0;
n is 1 or 2;
R$^1$ is hydrogen;
R$^3$ is hydrogen;
R$^4$ and R$^5$ are each independently hydrogen, $C_{1-6}$alkyl, $C_{1-6}$alkyloxy, hydroxy$C_{1-6}$alkyl, $C_{2-6}$alkenyl;
R$^6$ is hydrogen;

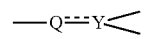

is —$CR^9$=C< and then the dotted line is a bond;
R$^9$ is hydrogen or $C_{1-6}$alkyl;
X is CH$_2$;
Z is a (a-1), (a-2) or (a-4);
R$^{10}$ and R$^{11}$ are each independently hydrogen, hydroxy or hydroxy$C_{1-6}$alkyl.

8. The method of claim 1, wherein
R$^2$ and R$^{20}$ are each independently halo, cyano, polyhalo$C_{1-6}$alkyl, $C_{1-6}$alkyl, morpholinyl, $C_{1-6}$alkyloxy, hydroxy$C_{1-6}$alkyl, or —NR$^{21}$R$^{22}$ wherein R$^{21}$ is hydrogen and R$^{22}$ is $C_{1-6}$alkylcarbonyl;
or R$^2$ and R$^{20}$ together with the phenyl ring to which they are attached form a naphthalenyl group,
or one of R$^2$ or R$^{20}$ is as defined above and the other one of R$^2$ or R$^{20}$ together with R$^9$ form a direct bond.

9. A method of treating a disorder mediated by a p53-MDM2 interaction comprising administering to a patient in need thereof a compound that is:

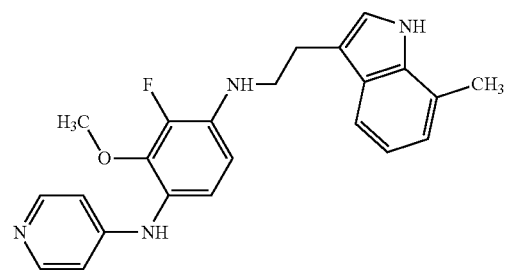

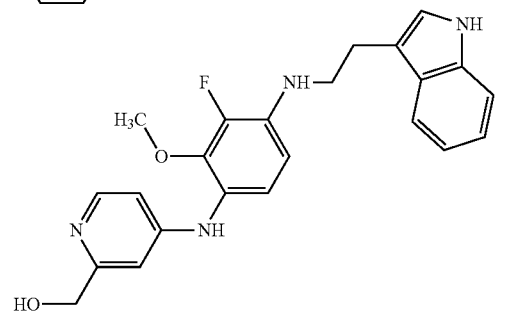

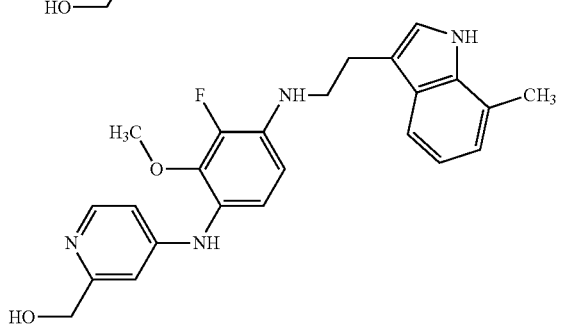

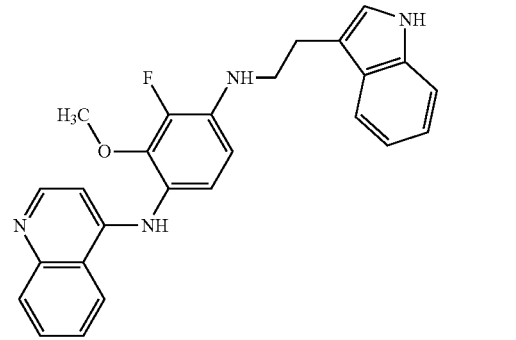

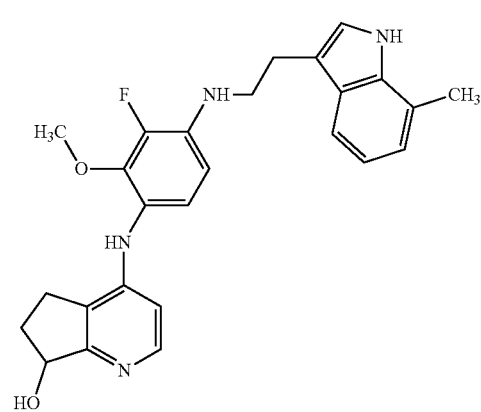

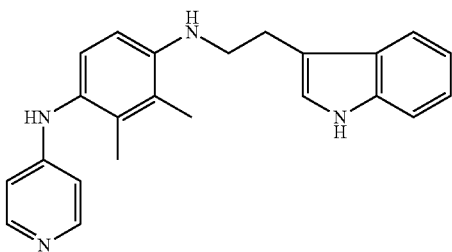 [SMILES: Cc1c(NCCc2c[nH]c3ccccc23)ccc(Nc2ccncc2)c1C]

a stereochemically isomeric form thereof;

an N-oxide form thereof, an addition salt thereof or a solvate thereof.

10. A method of treating a cancer that is mediated through a p53-MDM2 interaction, comprising administering to a patient in need thereof a compound of Formula (I):

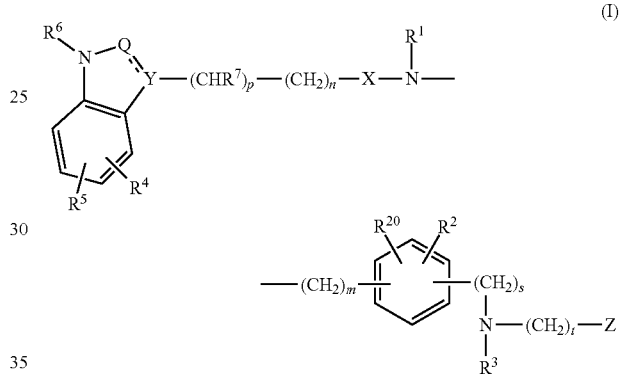

including any stereochemically isomeric form thereof, wherein m is 0, 1 or 2 and when m is 0 then a direct bond is intended;

n is 0, 1, 2 or 3 and when n is 0 then a direct bond is intended;

p is 0 or 1 and when p is 0 then a direct bond is intended;

s is 0 or 1 and when s is 0 then a direct bond is intended;

t is 0 or 1 and when t is 0 then a direct bond is intended;

X is C(=O) or CHR$^8$, wherein

R$^8$ is hydrogen; $C_{1-6}$alkyl; $C_{3-7}$cycloalkyl; —C(=O)—NR$^{17}$R$^{18}$; carboxyl; aryl$C_{1-6}$alkyloxycarbonyl; heteroaryl; heteroarylcarbonyl; heteroaryl$C_{1-6}$alkyloxycarbonyl; piperazinylcarbonyl; pyrrolidinyl; piperidinylcarbonyl; $C_{1-6}$alkyloxycarbonyl; $C_{1-6}$ alkyl substituted with a substituent that is hydroxy, amino, aryl, or heteroaryl; $C_{3-7}$cycloalkyl substituted with a substituent that is hydroxy, amino, aryl, or heteroaryl; piperazinylcarbonyl substituted with a substituent that is hydroxy, hydroxy$C_{1-6}$alkyl, or hydroxy $C_{1-6}$alkyloxy$C_{1-6}$alkyl; pyrrolidinyl substituted with hydroxy$C_{1-6}$alkyl; or piperidinylcarbonyl substituted with one or two substituents that are hydroxy, $C_{1-6}$alkyl, hydroxy$C_{1-6}$alkyl, $C_{1-6}$alkyloxy$C_{1-6}$alkyl, $C_{1-6}$alkyl(dihydroxy)$C_{1-6}$alkyl, or $C_{1-6}$alkyloxy(hydroxy)$C_{1-6}$alkyl;

R$^{17}$ and R$^{18}$ are each independently hydrogen, C$_{1-6}$alkyl, di(C$_{1-6}$alkyl)aminoC$_{1-6}$alkyl, arylC$_{1-6}$alkyl, C$_{1-6}$alkyloxyC$_{1-6}$alkyl, hydroxyC$_{1-6}$alkyl, hydroxyC$_{1-6}$alkyl(C$_{1-6}$alkyl), or hydroxyC$_{1-6}$alkyl(arylC$_{1-6}$alkyl);

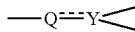

is —CR$^9$=C< and then the dotted line is a bond, —C(=O)—CH<, —C(=O)—N<, —CHR$^9$—CH<, or —CHR$^9$—N<, wherein each R$^9$ is independently hydrogen or C$_{1-6}$alkyl, or wherein R$^9$ together with one of R$^2$ or R$^{20}$ form a direct bond;

R$^1$ is hydrogen; aryl; heteroaryl; C$_{1-6}$alkyloxycarbonyl; C$_{1-12}$alkyl; or C$_{1-12}$alkyl substituted with one or two substituents independently that are hydroxy, aryl, heteroaryl, amino, C$_{1-6}$alkyloxy, mono- or di(C$_{1-6}$alkyl)amino, morpholinyl, piperidinyl, pyrrolidinyl, piperazinyl, C$_{1-6}$alkylpiperazinyl, arylC$_{1-6}$alkylpiperazinyl, heteroarylC$_{1-6}$alkylpiperazinyl, C$_{3-7}$cycloalkyl-piperazinyl, or C$_{3-7}$cycloalkylC$_{1-6}$alkylpiperazinyl;

R$^2$ and R$^{20}$ are each independently halo, hydroxy, cyano, nitro, carboxyl; polyhaloC$_{1-6}$alkyl, polyhaloC$_{1-6}$alkyloxy; C$_{1-6}$alkyl, C$_{3-7}$cycloalkyl, C$_{2-6}$alkenyl, aryl, heteroaryl, arylC$_{1-6}$alkyl, heteroarylC$_{1-6}$alkyl, C$_{3-7}$cycloalkylC$_{1-6}$alkyl, morpholinyl, piperidinyl, pyrrolidinyl, piperazinyl, C$_{1-6}$alkyloxy, aryloxy, heteroaryloxy, C$_{1-6}$alkylthio, arylthio, heteroarylthio, C$_{1-6}$alkylcarbonyl, C$_{3-7}$cycloalkylcarbonyl, arylcarbonyl, heteroarylcarbonyl, C$_{1-6}$alkyloxycarbonyl, C$_{3-7}$cycloalkyloxycarbonyl, aryloxycarbonyl, heteroaryloxycarbonyl, C$_{1-6}$alkylcarbonyloxy, C$_{3-7}$cycloalkylcarbonyloxy, arylcarbonyloxy or heteroarylcarbonyloxy, any of said groups being optionally and independently substituted with one or more substituents that are halo, hydroxy, cyano, nitro, carboxyl, amino, mono- or di(C$_{1-6}$alkyl)amino, C$_{1-6}$alkyl, polyhaloC$_{1-6}$alkyl, aryl, heteroaryl, C$_{1-6}$alkyloxy, C$_{1-6}$alkylcarbonyl, C$_{1-6}$alkyloxycarbonyl or C$_{1-6}$alkylcarbonyloxy; or —(CH$_2$)$_w$—(C(=O))$_y$NR$^{21}$R$^{22}$ wherein w is 0, 1, 2, 3, 4, 5 or 6 and when w is 0 then a direct bond is intended;

y is 0 or 1 and when y is 0 then a direct bond is intended;

R$^{21}$ and R$^{22}$ are each independently hydrogen, C$_{1-6}$alkyl, C$_{3-7}$cycloalkyl, C$_{1-6}$alkylcarbonyl, or arylC$_{1-6}$alkylcarbonyl, any of said groups being optionally and independently substituted with one or more substituents that are halo, hydroxy, amino, mono- or di(C$_{1-6}$alkyl)amino, C$_{1-6}$alkyl, polyhaloC$_{1-6}$alkyl, C$_{1-6}$alkyloxy, aryl, or heteroaryl;

or R$^{21}$ and R$^{22}$ together with the nitrogen to which they are attached form morpholinyl, piperidinyl, pyrrolidinyl or piperazinyl, any of said groups being optionally and independently substituted with one or more one or two, substituents that are C$_{1-6}$alkyl, polyhaloC$_{1-6}$alkyl, C$_{1-6}$alkyloxy, C$_{3-7}$cycloalkyl, C3-7cycloalkylC$_{1-6}$alkyl, arylC$_{1-6}$alkyl, or heteroarylC$_{1-6}$alkyl;

or R$^2$ and R$^{20}$ together with the phenyl ring to which they are attached form a naphthalenyl group, optionally substituted with one or more substituents each independently that are halo, hydroxy, amino, mono- or di(C$_{1-6}$alkyl)amino, C$_{1-6}$alkyl, polyhaloC$_{1-6}$alkyl, C$_{1-6}$alkyloxy, aryl, or heteroaryl;

or R$^2$ and R$^{20}$ together form a bivalent radical of the formula —(CH$_2$)$_b$—, wherein b is 3, 4 or 5, optionally substituted with one or more substituents that are halo, hydroxy, amino, mono- or di(C$_{1-6}$alkyl)amino, C$_{1-6}$alkyl, polyhaloC$_{1-6}$alkyl, C$_{1-6}$alkyloxy, aryl, or heteroaryl;

or one of R$^2$ or R$^{20}$ is as defined above and the other one of R$^2$ or R$^{20}$ together with R$^9$ form a direct bond;

R$^3$ is hydrogen; C$_{1-6}$alkyl; heteroaryl; C$_{3-7}$cycloalkyl; C$_{1-6}$alkyl substituted with a substituent that is hydroxy, amino, aryl, or heteroaryl; or C$_{3-7}$cycloalkyl substituted with a substituent that is hydroxy, amino, aryl, or heteroaryl;

R$^4$ and R$^5$ are each independently hydrogen, halo, C$_{1-6}$alkyl, hydroxyC$_{1-6}$alkyl, polyhalo-C$_{1-6}$alkyl, cyano, cyanoC$_{1-6}$alkyl, hydroxy, amino, C$_{2-6}$alkenyl or C$_{1-6}$alkyloxy; or R$^4$ and R$^5$ together form a bivalent radical that is methylenedioxy or ethylenedioxy;

R$^6$ is hydrogen, C$_{1-6}$alkyloxycarbonyl, or C$_{1-6}$alkyl;

when p is 1 then R$^7$ is hydrogen, arylC$_{1-6}$alkyl, hydroxy, or heteroarylC$_{1-6}$alkyl;

Z is a radical that is:

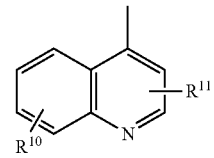

(a-1)

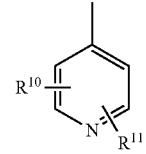

(a-2)

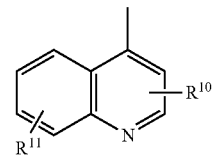

(a-3)

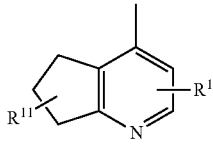

(a-4)

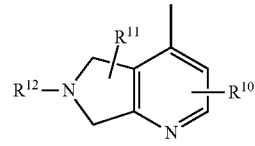

(a-5)

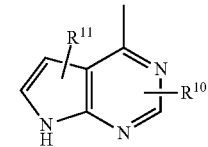

(a-6)

-continued (a-7)

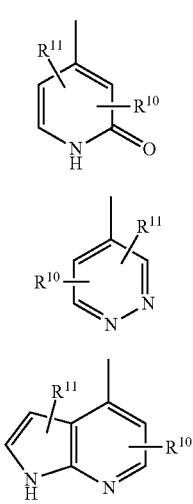

(a-8)

(a-9)

wherein
R$^{10}$ or R$^{11}$ are each independently hydrogen, halo, hydroxy, amino, C$_{1-6}$alkyl, nitro, polyhaloC$_{1-6}$alkyl, cyano, cyanoC$_{1-6}$alkyl, tetrazoloC$_{1-6}$alkyl, aryl, heteroaryl, arylC$_{1-6}$alkyl, heteroarylC$_{1-6}$alkyl, aryl(hydroxy)C$_{1-6}$alkyl, heteroaryl(hydroxy)C$_{1-6}$alkyl, arylcarbonyl, heteroarylcarbonyl, C$_{1-6}$alkylcarbonyl, arylC$_{1-6}$alkylcarbonyl, heteroarylC$_{1-6}$alkylcarbonyl, C$_{1-6}$alkyloxy, C$_{3-7}$cycloalkylcarbonyl, C$_{3-7}$cycloalkyl(hydroxy)C$_{1-6}$alkyl, arylC$_{1-6}$alkyloxyC$_{1-6}$alkyl, C$_{1-6}$alkyloxyC$_{1-6}$alkyloxyC$_{1-6}$alkyl, C$_{1-6}$alkylcarbonyloxyC$_{1-6}$alkyl, C$_{1-6}$alkyloxycarbonylC$_{1-6}$alkyloxyC$_{1-6}$alkyl, hydroxyC$_{1-6}$alkyloxyC$_{1-6}$alkyl, C$_{1-6}$alkyloxycarbonylC$_{2-6}$alkenyl, C$_{1-6}$alkyloxyC$_{1-6}$alkyl, C$_{1-6}$alkyloxycarbonyl, C$_{1-6}$alkylcarbonyloxy, aminocarbonyl, hydroxyC$_{1-6}$alkyl, aminoC$_{1-6}$alkyl, hydroxycarbonyl, hydroxycarbonylC$_{1-6}$alkyl or —(CH$_2$)$_v$—(C(=O))$_r$—(CHR$^{19}$)$_u$—NR$^{13}$R$^{14}$, wherein
v is 0, 1, 2, 3, 4, 5, or 6 and when v is 0 then a direct bond is intended;
r is 0 or 1 and when r is 0 then a direct bond is intended;
u is 0, 1, 2, 3, 4, 5, or 6 and when u is 0 then a direct bond is intended;
R$^{19}$ is hydrogen or C$_{1-6}$alkyl;
R$^{13}$ and R$^{14}$ are each independently hydrogen; C$_{1-12}$alkyl; C$_{1-6}$alkylcarbonyl; C$_{1-6}$alkylsulfonyl; arylC$_{1-6}$alkylcarbonyl; C$_{3-7}$cycloalkyl; C$_{3-7}$cycloalkylcarbonyl; —(CH$_2$)$_k$—NR$^{15}$R$^{16}$; C$_{1-12}$alkyl substituted with a substituent that is hydroxy, hydroxycarbonyl, cyano, C$_{1-6}$alkyloxycarbonyl, C$_{1-6}$alkyloxy, aryl or heteroaryl; or C$_{3-7}$cycloalkyl substituted with a substituent that is hydroxy, C$_{1-6}$alkyloxy, aryl, amino, arylC$_{1-6}$alkyl, heteroaryl or heteroarylC$_{1-6}$alkyl; or
R$^{13}$ and R$^{14}$ together with the nitrogen to which they are attached form morpholinyl, piperidinyl, pyrrolidinyl, piperazinyl, or piperazinyl substituted with a substituent that is C$_{1-6}$alkyl, arylC$_{1-6}$alkyl, arylC$_{1-6}$alkyloxycarbonyl, heteroarylC$_{1-6}$alkyl, C$_{3-7}$cycloalkyl, or C$_{3-7}$cycloalkylC$_{1-6}$alkyl; wherein
k is 0, 1, 2, 3, 4, 5, or 6 and when k is 0 then a direct bond is intended;
R$^{15}$ and R$^{16}$ are each independently hydrogen; C$_{1-12}$alkyl; arylC$_{1-6}$alkyloxycarbonyl; C$_{3-7}$cycloalkyl; C$_{1-12}$alkyl substituted with a substituent that is hydroxy, C$_{1-6}$alkyloxy, aryl, or heteroaryl; or C$_{3-7}$cycloalkyl substituted with a substituent that is hydroxy, C$_{1-6}$alkyloxy, aryl, arylC$_{1-6}$alkyl, heteroaryl, or heteroarylC$_{1-6}$alkyl; or
R$^{15}$ and R$^{16}$ together with the nitrogen to which they are attached form morpholinyl, piperazinyl, or piperazinyl substituted with C$_{1-6}$alkyloxycarbonyl;
R$^{12}$ is hydrogen; C$_{1-6}$alkyl; C$_{3-7}$cycloalkyl; C$_{1-6}$alkyl substituted with a substituent that is hydroxy, amino, C$_{1-6}$alkyloxy, or aryl; or C$_{3-7}$cycloalkyl substituted with a substituent that is hydroxy, amino, aryl, or C$_{1-6}$alkyloxy;
aryl is phenyl or naphthalenyl;
each phenyl or naphthalenyl can optionally be substituted with one, two or three substituents each independently halo, hydroxy, C$_{1-6}$alkyl, amino, polyhaloC$_{1-6}$alkyl or C$_{1-6}$alkyloxy; and
each phenyl or naphthalenyl can optionally be substituted with a bivalent radical that is methylenedioxy or ethylenedioxy;
heteroaryl is pyridinyl, indolyl, quinolinyl, imidazolyl, furanyl, thienyl, oxadiazolyl, tetrazolyl, benzofuranyl or tetrahydrofuranyl;
each pyridinyl, indolyl, quinolinyl, imidazolyl, furanyl, thienyl, oxadiazolyl, tetrazolyl, benzofuranyl, or tetrahydrofuranyl can optionally be substituted with one, two or three substituents each independently halo, hydroxy, C$_{1-6}$alkyl, amino, polyhaloC$_{1-6}$alkyl, aryl, arylC$_{1-6}$alkyl or C$_{1-6}$alkyloxy; or
each pyridinyl, indolyl, quinolinyl, imidazolyl, furanyl, thienyl, benzofuranyl, or tetrahydrofuranyl can optionally be substituted with a bivalent radical that is methylenedioxy or ethylenedioxy;
wherein when R$^2$ or R$^{20}$ is C$_{1-6}$alkyl or C$_{1-6}$alkyloxy, then R$^2$ or R$^{20}$ is not fluorine;
an N-oxide form thereof, an addition salt thereof or a solvate thereof.

11. The method of claim 1, where R$^2$ or R$^{20}$ are substituted with one or two substituents.

12. The method of claim 1, where R$^{21}$ or R$^{22}$ are substituted with one or two substituents.

13. The method of claim 1, wherein R$^{21}$ and R$^{22}$ together with the nitrogen to which they are attached form morpholinyl, piperidinyl, pyrrolidinyl or piperazinyl, any of said groups are independently substituted with one or two substituents that are C$_{1-6}$alkyl, polyhaloC$_{1-6}$alkyl, C$_{1-6}$alkyloxy, C$_{3-7}$cycloalkyl, C$_{3-7}$cycloalkylC$_{1-6}$alkyl, arylC$_{1-6}$alkyl, or heteroarylC$_{1-6}$alkyl.

14. The method of claim 1, wherein R$^2$ and R$^{20}$ together with the phenyl ring to which they are attached form a naphthalenyl group, substituted with one or two substituents each independently halo, hydroxy, amino, mono- or di(C$_{1-6}$alkyl)amino, C$_{1-6}$alkyl, polyhaloC$_{1-6}$alkyl, C$_{1-6}$alkyloxy, aryl, or heteroaryl.

15. The method of claim 1, wherein R$^2$ and R$^{20}$ together form a bivalent radical of the formula —(CH$_2$)$_b$— wherein b is 3, 4 or 5, substituted with one or two substituents that are halo, hydroxy, amino, mono- or di(C$_{1-6}$alkyl)amino, C$_{1-6}$alkyl, polyhaloC$_{1-6}$alkyl, C$_{1-6}$alkyloxy, aryl, or heteroaryl.

16. The method of claim 10, where $R^2$ or $R^{20}$ are substituted with one or two substituents.

17. The method of claim 10, where $R^{21}$ or $R^{22}$ are substituted with one or two substituents.

18. The method of claim 10, wherein $R^{21}$ and $R^{22}$ together with the nitrogen to which they are attached form morpholinyl, piperidinyl, pyrrolidinyl or piperazinyl, any of said groups are independently substituted with one or two substituents that are $C_{1-6}$alkyl, polyhalo$C_{1-6}$alkyl, $C_{1-6}$alkyloxy, $C_{3-7}$cycloalkyl, $C_{3-7}$cycloalkyl$C_{1-6}$alkyl, aryl$C_{1-6}$alkyl, or heteroaryl$C_{1-6}$alkyl.

19. The method of claim 10, wherein $R^2$ and $R^{20}$ together with the phenyl ring to which they are attached form a naphthalenyl group, substituted with one or two substituents each independently halo, hydroxy, amino, mono- or di($C_{1-6}$alkyl)amino, $C_{1-6}$alkyl, polyhalo$C_{1-6}$alkyl, $C_{1-6}$alkyloxy, aryl, or heteroaryl.

20. The method of claim 10, wherein $R^2$ and $R^{20}$ together form a bivalent radical of the formula —$(CH_2)_b$— wherein b is 3, 4 or 5, substituted with one or two substituents that are halo, hydroxy, amino, mono- or di($C_{1-6}$alkyl)amino, $C_{1-6}$alkyl, polyhalo$C_{1-6}$alkyl, $C_{1-6}$alkyloxy, aryl, or heteroaryl.

21. The method of claim 10, wherein the cancer is breast cancer, colorectal cancer, ovarian cancer, non-small cell lung cancer or acute myelogenous cancer.

\* \* \* \* \*